United States Patent
Yeung et al.

(10) Patent No.: US 10,882,844 B2
(45) Date of Patent: Jan. 5, 2021

(54) COMPOUNDS USEFUL AS IMMUNOMODULATORS

(71) Applicant: Bristol-Myers Squibb Company, Princeton, NJ (US)

(72) Inventors: Kap-Sun Yeung, Madison, CT (US); Katharine A. Grant-Young, Madison, CT (US); Li-Qiang Sun, Princeton, NJ (US); David R. Langley, Meriden, CT (US); Denis R. St. Laurent, Newington, CT (US); Paul M. Scola, Glastonbury, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 16/471,531

(22) PCT Filed: Dec. 19, 2017

(86) PCT No.: PCT/US2017/067198
§ 371 (c)(1),
(2) Date: Jun. 19, 2019

(87) PCT Pub. No.: WO2018/118848
PCT Pub. Date: Jun. 28, 2018

(65) Prior Publication Data
US 2019/0352280 A1    Nov. 21, 2019

Related U.S. Application Data

(60) Provisional application No. 62/436,674, filed on Dec. 20, 2016.

(51) Int. Cl.
C07D 401/12    (2006.01)
C07D 413/12    (2006.01)
C07D 413/14    (2006.01)
C07D 401/14    (2006.01)
C07D 471/08    (2006.01)

(52) U.S. Cl.
CPC ........ *C07D 401/14* (2013.01); *C07D 401/12* (2013.01); *C07D 413/12* (2013.01); *C07D 413/14* (2013.01); *C07D 471/08* (2013.01)

(58) Field of Classification Search
CPC ... C07D 413/12; C07D 413/14; C07D 401/12
See application file for complete search history.

(56) References Cited

U.S. PATENT DOCUMENTS

| | | | |
|---|---|---|---|
| 9,850,225 B2 | 12/2017 | Chupak et al. | |
| 9,872,852 B2 | 1/2018 | Chupak et al. | |
| 10,144,706 B2 | 12/2018 | Chupak et al. | |
| 2015/0291549 A1 | 10/2015 | Chupak et al. | |

FOREIGN PATENT DOCUMENTS

| | | | | |
|---|---|---|---|---|
| EP | 2011788 A1 | 1/2009 | | |
| WO | WO 2015/034820 A1 | 3/2015 | | |
| WO | WO-2016051186 A1 * | 4/2016 | ........... | C07D 403/12 |
| WO | WO 2017/066227 A1 | 4/2017 | | |
| WO | WO 2018/009505 A1 | 1/2018 | | |
| WO | WO 2018/044963 A1 | 3/2018 | | |
| WO | WO 2018/183171 A1 | 10/2018 | | |

OTHER PUBLICATIONS

Guzik; K., et al., "Small-Molecule Inhibitors of the Programmed Cell Death-1/Programmed Death-Ligand 1 9PD-1/PD-L1) Interaction via Transiently Induced Protein States and Dimerization of PD-L1," Journal of Medicinal Chemistry, 2017, vol. 60, No. 13, pp. 5857-5867.

* cited by examiner

*Primary Examiner* — Laura L Stockton
(74) *Attorney, Agent, or Firm* — Sterne, Kessler, Goldstein & Fox P.L.L.C.

(57) ABSTRACT

The present disclosure generally relates to compounds useful as immunomodulators. Provided herein are compounds, compositions comprising such compounds, and methods of their use. The disclosure further pertains to pharmaceutical compositions comprising at least one compound according to the disclosure that are useful for the treatment of various diseases, including cancer and infectious diseases.

11 Claims, No Drawings

Specification includes a Sequence Listing.

SEQUENCE LISTING

<160> NUMBER OF SEQ ID NOS: 2

<210> SEQ ID NO 1

```
<211> LENGTH: 384
<212> TYPE: PRT
<213> ORGANISM: Homo sapiens

<400> SEQUENCE: 1
```

| | | | | | | | | | | | | | | |
|---|---|---|---|---|---|---|---|---|---|---|---|---|---|---|
| Leu | Asp | Ser | Pro | Asp | Arg | Pro | Trp | Asn | Pro | Thr | Phe | Ser | Pro | Ala |
| 1 | | | | 5 | | | | | 10 | | | | | 15 |
| Leu | Leu | Val | Val | Thr | Glu | Gly | Asp | Asn | Ala | Thr | Phe | Thr | Cys | Ser | Phe |
| | | | 20 | | | | | 25 | | | | | 30 | | |
| Ser | Asn | Thr | Ser | Glu | Ser | Phe | Val | Leu | Asn | Trp | Tyr | Arg | Met | Ser | Pro |
| | | 35 | | | | | 40 | | | | | 45 | | | |
| Ser | Asn | Gln | Thr | Asp | Lys | Leu | Ala | Ala | Phe | Pro | Glu | Asp | Arg | Ser | Gln |
| 50 | | | | | 55 | | | | | 60 | | | | | |
| Pro | Gly | Gln | Asp | Cys | Arg | Phe | Arg | Val | Thr | Gln | Leu | Pro | Asn | Gly | Arg |
| 65 | | | | 70 | | | | | 75 | | | | | 80 | |
| Asp | Phe | His | Met | Ser | Val | Val | Arg | Ala | Arg | Arg | Asn | Asp | Ser | Gly | Thr |
| | | | 85 | | | | | 90 | | | | | 95 | | |
| Tyr | Leu | Cys | Gly | Ala | Ile | Ser | Leu | Ala | Pro | Lys | Ala | Gln | Ile | Lys | Glu |
| | | | 100 | | | | | 105 | | | | | 110 | | |
| Ser | Leu | Arg | Ala | Glu | Leu | Arg | Val | Thr | Glu | Arg | Arg | Ala | Glu | Val | Pro |
| | | 115 | | | | | 120 | | | | | 125 | | | |
| Thr | Ala | His | Pro | Ser | Pro | Ser | Pro | Arg | Pro | Ala | Gly | Gln | Phe | Gln | Gly |
| 130 | | | | | 135 | | | | | 140 | | | | | |
| Ser | Pro | Gly | Gly | Gly | Gly | Arg | Glu | Pro | Lys | Ser | Ser | Asp | Lys | Thr |
| 145 | | | | 150 | | | | | 155 | | | | | 160 |
| His | Thr | Ser | Pro | Ser | Pro | Ala | Pro | Glu | Leu | Leu | Gly | Gly | Ser | Ser |
| | | | 165 | | | | | 170 | | | | | 175 | |
| Val | Phe | Leu | Phe | Pro | Pro | Lys | Pro | Lys | Asp | Thr | Leu | Met | Ile | Ser | Arg |
| | | | 180 | | | | | 185 | | | | | 190 | | |
| Thr | Pro | Glu | Val | Thr | Cys | Val | Val | Asp | Val | Ser | His | Glu | Asp | Pro |
| | | | 195 | | | | | 200 | | | | | 205 | | |
| Glu | Val | Lys | Phe | Asn | Trp | Tyr | Val | Asp | Gly | Val | Glu | Val | His | Asn | Ala |
| | 210 | | | | | 215 | | | | | 220 | | | | |
| Lys | Thr | Lys | Pro | Arg | Glu | Glu | Gln | Tyr | Asn | Ser | Thr | Tyr | Arg | Val | Val |
| 225 | | | | | 230 | | | | | 235 | | | | | 240 |
| Ser | Val | Leu | Thr | Val | Leu | His | Gln | Asp | Trp | Leu | Asn | Gly | Lys | Glu | Tyr |
| | | | 245 | | | | | 250 | | | | | 255 | | |
| Lys | Cys | Lys | Val | Ser | Asn | Lys | Ala | Leu | Pro | Ala | Pro | Ile | Glu | Lys | Thr |
| | | | 260 | | | | | 265 | | | | | 270 | | |
| Ile | Ser | Lys | Ala | Lys | Gly | Gln | Pro | Arg | Glu | Pro | Gln | Val | Tyr | Thr | Leu |
| | | 275 | | | | | 280 | | | | | 285 | | | |
| Pro | Pro | Ser | Arg | Asp | Glu | Leu | Thr | Lys | Asn | Gln | Val | Ser | Leu | Thr | Cys |
| 290 | | | | | 295 | | | | | 300 | | | | | |
| Leu | Val | Lys | Gly | Phe | Tyr | Pro | Ser | Asp | Ile | Ala | Val | Glu | Trp | Glu | Ser |
| 305 | | | | 310 | | | | | 315 | | | | | 320 | |
| Asn | Gly | Gln | Pro | Glu | Asn | Asn | Tyr | Lys | Thr | Thr | Pro | Pro | Val | Leu | Asp |
| | | | | 325 | | | | | 330 | | | | | 335 | |
| Ser | Asp | Gly | Ser | Phe | Phe | Leu | Tyr | Ser | Lys | Leu | Thr | Val | Asp | Lys | Ser |
| | | | 340 | | | | | 345 | | | | | 350 | | |
| Arg | Trp | Gln | Gln | Gly | Asn | Val | Phe | Ser | Cys | Ser | Val | Met | His | Glu | Ala |
| | | | 355 | | | | | 360 | | | | | 365 | | |
| Leu | His | Asn | His | Tyr | Thr | Gln | Lys | Ser | Leu | Ser | Leu | Ser | Pro | Gly | Lys |
| | 370 | | | | | 375 | | | | | 380 | | | | |

```
<210> SEQ ID NO 2
<211> LENGTH: 238
<212> TYPE: PRT
<213> ORGANISM: Homo sapiens

<400> SEQUENCE: 2

Ala Phe Thr Val Thr Val Pro Lys Asp Leu Tyr Val Val Glu Tyr Gly
1               5                   10                  15

Ser Asn Met Thr Ile Glu Cys Lys Phe Pro Val Glu Lys Gln Leu Asp
            20                  25                  30

Leu Ala Ala Leu Ile Val Tyr Trp Glu Met Glu Asp Lys Asn Ile Ile
        35                  40                  45

Gln Phe Val His Gly Glu Glu Asp Leu Lys Val Gln His Ser Ser Tyr
    50                  55                  60

Arg Gln Arg Ala Arg Leu Leu Lys Asp Gln Leu Ser Leu Gly Asn Ala
65                  70                  75                  80

Ala Leu Gln Ile Thr Asp Val Lys Leu Gln Asp Ala Gly Val Tyr Arg
                85                  90                  95

Cys Met Ile Ser Tyr Gly Gly Ala Asp Tyr Lys Arg Ile Thr Val Lys
            100                 105                 110

Val Asn Ala Pro Tyr Asn Lys Ile Asn Gln Arg Ile Leu Val Val Asp
        115                 120                 125

Pro Val Thr Ser Glu His Glu Leu Thr Cys Gln Ala Glu Gly Tyr Pro
    130                 135                 140

Lys Ala Glu Val Ile Trp Thr Ser Ser Asp His Gln Val Leu Ser Gly
145                 150                 155                 160

Lys Thr Thr Thr Thr Asn Ser Lys Arg Glu Glu Lys Leu Phe Asn Val
                165                 170                 175

Thr Ser Thr Leu Arg Ile Asn Thr Thr Thr Asn Glu Ile Phe Tyr Cys
            180                 185                 190

Thr Phe Arg Arg Leu Asp Pro Glu Glu Asn His Thr Ala Glu Leu Val
        195                 200                 205

Ile Pro Glu Leu Pro Leu Ala His Pro Pro Asn Glu Arg Thr Gly Ser
    210                 215                 220

Ser Glu Thr Val Arg Phe Gln Gly His His His His His His
225                 230                 235
```

COMPOUNDS USEFUL AS IMMUNOMODULATORS

CROSS REFERENCE TO RELATED APPLICATION

This application claims the priority of U.S. provisional Ser. No. 62/436,674 filed Dec. 20, 2016 which is herein incorporated by reference.

The present disclosure generally relates to compounds useful as inhibitors of the PD-1/PD-L1 protein/protein and CD80/PD-L1 protein/protein interactions. Provided herein are compounds, compositions comprising such compounds, and methods of their use. The disclosure further pertains to pharmaceutical compositions comprising at least one compound according to the disclosure that are useful for the treatment of various diseases, including cancer and infectious diseases.

Programmed death-1 (CD279) is a receptor on T cells that has been shown to suppress activating signals from the T cell receptor when bound by either of its ligands, Programmed death-ligand 1 (PD-L1, CD274, B7-H1) or PD-L2 (CD273, B7-DC) (Sharpe et al., Nat. Imm. 2007). When PD-1 expressing T cells contact cells expressing its ligands, functional activities in response to antigenic stimuli, including proliferation, cytokine secretion, and cytolytic activity are reduced. PD-1/PD-Ligand interactions down regulate immune responses during resolution of an infection or tumor, or during the development of self tolerance (Keir Me, Butte M J, Freeman G J, et al. Annu. Rev. Immunol. 2008; 26: Epub). Chronic antigen stimulation, such as that which occurs during tumor disease or chronic infections, results in T cells that express elevated levels of PD-1 and are dysfunctional with respect to activity towards the chronic antigen (reviewed in Kim and Ahmed, Curr Opin Imm, 2010). This is termed "T cell exhaustion". B cells also display PD-1/PD-ligand suppression and "exhaustion".

PD-L1 has also been shown to interact with CD80 (Butte M J et al., Immunity 27:111-122 (2007)). The interaction of PD-L1/CD80 on expressing immune cells has been shown to be an inhibitory one. Blockade of this interaction has been shown to abrogate this inhibitory interaction (Paterson A M, et al., J Immunol., 187:1097-1105 (2011); Yang J, et al. J Immunol. August 1; 187(3):1113-9 (2011)).

Blockade of the PD-1/PD-L1 interaction using antibodies to PD-L1 has been shown to restore and augment T cell activation in many systems. Patients with advanced cancer benefit from therapy with a monoclonal antibody to PD-L1 (Brahmer et al., New Engl J Med 2012). Preclinical animal models of tumors have shown that blockade of the PD-1/PD-L1 pathway by monoclonal antibodies can enhance the immune response and result in the immune response to a number of histologically distinct tumors (Dong H, Chen L. J Mol Med. 2003; 81(5):281-287; Dong H, Strome S E, Salamoa D R, et al. Nat Med. 2002; 8(8):793-800).

Interference with the PD-1/PD-L1 interaction has also shown enhanced T cell activity in chronic infection systems. Chronic lymphocytic chorio meningitis virus infection of mice also exhibits improved virus clearance and restored immunity with blockade of PD-L1 (Barber D L, Wherry E J, Masopust D, et al. Nature 2006; 439(7077):682-687). Humanized mice infected with HIV-1 show enhanced protection against viremia and reduced viral depletion of CD4+ T cells (Palmer et al., J. Immunol. 2013). Blockade of PD-1/PD-L1 through monoclonal antibodies to PD-L1 can restore in vitro antigen-specific functionality to T cells from HIV patients (Day, Nature 2006; Petrovas, J. Exp. Med. 2006; Trautman, Nature Med. 2006; D'Souza, J. Immunol. 2007; Zhang, Blood 2007; Kaufmann, Nature Imm. 2007; Kasu, J. Immunol. 2010; Porichis, Blood 2011), HCV patients [Golden-Mason, J. Virol. 2007; Jeung, J. Leuk. Biol. 2007; Urbani, J. Hepatol. 2008; Nakamoto, PLoS Path. 2009; Nakamoto, Gastroenterology 2008] or HBV patients (Boni, J. Virol. 2007; Fisicaro, Gastro. 2010; Fisicaro et al., Gastroenterology, 2012; Boni et al., Gastro., 2012; Penna et al., J Hep, 2012; Raziorrough, Hepatology 2009; Liang, World J Gastro. 2010; Zhang, Gastro. 2008).

Blockade of the PD-L1/CD80 interaction has also been shown to stimulate immunity (Yang J., et al., J Immunol. August 1; 187(3):1113-9 (2011)). The immune stimulation resulting from blockade of the PD-L1/CD80 interaction has been shown to be enhanced through combination with blockade of further PD-1/PD-L1 or PD-1/PD-L2 interactions.

Alterations in immune cell phenotypes are hypothesized to be an important factor in septic shock (Hotchkiss, et al., Nat Rev Immunol (2013)). These include increased levels of PD-1 and PD-L1 and T ceoll apoptosis (Guignant, et al, Crit. Care (2011)). Antibodies directed to PD-L1 can reduce the level of Immune cell apoptosis (Zhang et al, Crit. Care (2011)). Furthermore, mice lacking PD-1 expression are more resistant to septic shock symptoms than wildtype mice (Yang J., et al. J Immunol. August 1; 187(3):1113-9 (2011)). Studies have revealed that blockade of the interactions of PD-L1 using antibodies can suppress inappropriate immune responses and ameliorate disease symptoms.

In addition to enhancing immunologic responses to chronic antigens, blockade of the PD-1/PD-L1 pathway has also been shown to enhance responses to vaccination, including therapeutic vaccination in the context of chronic infection (S. J. Ha, S. N. Mueller, E. J. Wherry et al., The Journal of Experimental Medicine, vol. 205, no. 3, pp. 543-555, 2008; A. C. Finnefrock, A. Tang, F. Li et al., The Journal of Immunology, vol. 182, no. 2, pp. 980-987, 2009; M. -Y. Song, S. -H. Park, H. J. Nam, D. -H. Choi, and Y.-C. Sung, The Journal of Immunotherapy, vol. 34, no. 3, pp. 297-306, 2011).

The PD-1 pathway is a key inhibitory molecule in T cell exhaustion that arises from chronic antigen stimulation during chronic infections and tumor disease. Blockade of the PD-1/PD-L1 interaction through targeting the PD-L1 protein has been shown to restore antigen-specific T cell immune functions in vitro and in vivo, including enhanced responses to vaccination in the setting of tumor or chronic infection. Accordingly, agents that block the interaction of PD-L1 with either PD-1 or CD80 are desired.

Applicants found potent compounds that have activity as inhibitors of the interaction of PD-L1 with PD-1 and CD80, and thus may be useful for therapeutic administration to enhance immunity in cancer or infections, including therapeutic vaccine. These compounds are provided to be useful as pharmaceuticals with desirable stability, bioavailability, therapeutic index, and toxicity values that are important to their drugability.

In a first aspect the present disclosure provides a compound of formula (I)

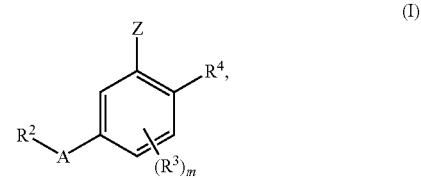

or a pharmaceutically acceptable salt thereof, wherein:

m is 0, 1, or 2;

Z is selected from —OCH₃ and —O(CH₂)ₙAr; wherein n is 1, 2, 3, or 4;

Ar is selected from phenyl and pyridinyl, wherein each ring is optionally substituted with 1, 2, 3, or 4 substituents independently selected from $C_1$-$C_4$alkoxy, $C_1$-$C_4$alkyl, amido, carboxy, cyano, formyl, halo, halo$C_1$-$C_4$alkyl, halo$C_1$-$C_4$alkoxy, and nitro;

A is selected from —CH₂O—, —OCH₂—, —(CH₂)₂—, —CH=CH—, —C(O)NH—, and —NHC(O)—, wherein each group is drawn with its left side attached to $R^2$ and its right side attached to the phenyl ring;

$R^2$ is selected from

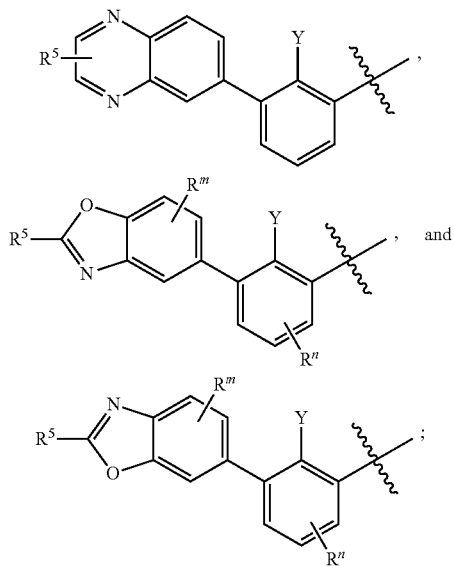

wherein $R^m$ and $R^n$ are independently selected from hydrogen, $C_1$-$C_3$alkyl, and halo;

Y is selected from hydrogen, $C_1$-$C_3$alkoxy, $C_1$-$C_3$alkyl, cyano, and halo;

$R^5$ is a three- to ten-membered monocyclic or bicyclic ring optionally containing one or two heteroatoms independently selected from nitrogen and oxygen and containing zero, one, two, or three double bonds, wherein said ring is optionally substituted with one, two, or three groups independently selected from $C_1$-$C_3$alkoxy, $C_1$-$C_3$alkoxy$C_1$-$C_4$alkyl, $C_1$-$C_4$alkoxycarbonyl, $C_1$-$C_4$alkyl, di($C_1$-$C_4$)alkylamino, amino, amino$C_1$-$C_4$alkyl, carboxy, carboxy$C_1$-$C_4$alkyl, $C_3$-$C_4$cycloalkyl, and phenyl;

each $R^3$ is independently selected from $C_1$-$C_4$alkyl, cyano, halo, and halo$C_1$-$C_4$alkyl;

$R^4$ is selected from —CH₂OH, —CHO and —(CH₂)ₙNR$^q$R$^8$; wherein n is 1, 2, 3, or 4;

$R^q$ is selected from hydrogen and $C_1$-$C_4$alkyl;

$R^8$ is selected from hydrogen, $C_1$-$C_4$alkyl, —(CH₂)ₙN(CH₃)₂,

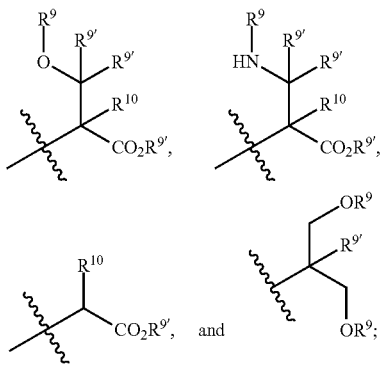

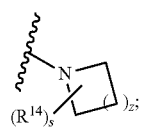

$R^9$ is selected from hydrogen and $C_1$alkyl;

each $R^{9'}$ is independently selected from hydrogen and $C_1$-$C_3$alkyl; and $R^{10}$ is selected from hydrogen and $C_1$-$C_4$alkyl; or $R^8$ and $R^q$, together with the nitrogen atom to which they are attached, form a ring which is

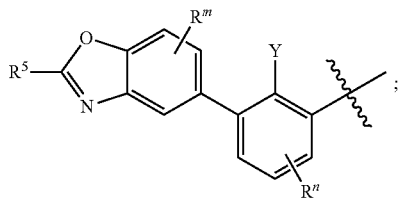

wherein s is 0, 1, or 2;

z is 1, 2, or 3; and each $R^{14}$ is independently selected from $C_1$-$C_4$alkoxycarbonyl, $C_1$-$C_6$alkyl, carboxy, halo, hydroxy, and hydroxy$C_1$-$C_4$alkyl.

In a first embodiment of the first aspect the present disclosure provides a compound of formula (I), or a pharmaceutically acceptable salt thereof, wherein m is 1 and $R^3$ is halo. In a second embodiment of the first aspect Z is —OCH₂Ar wherein Ar is pyridinyl substituted with a cyano group. In a third embodiment, A is —CH₂O—.

In a fourth embodiment of the first aspect the present disclosure provides a compound of formula (I), or a pharmaceutically acceptable salt thereof, wherein m is 1;

$R^3$ is halo

Z is OCH₂Ar wherein Ar is pyridinyl substituted with a cyano group;

A is —CH₂O—;

$R^2$ is

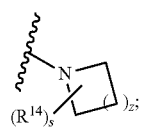

Y is selected from hydrogen and $C_1$alkyl;

$R^n$ is selected from hydrogen and $C_1$alkyl; and $R^5$ is a six- to eight-membered monocyclic or bicyclic ring containing one nitrogen atom and zero double bonds, wherein the ring is optionally substituted with one substituent selected from C$_1$alkyl, di(C$_1$-C$_4$)alkylamino, amino, carboxyC$_1$-C$_4$alkyl, and C$_3$-C$_4$cycloalkyl.

In a fifth embodiment of the first aspect the present disclosure provides a compound of formula (I), or a pharmaceutically acceptable salt thereof, wherein m is 1;
R$^3$ is halo
Z is OCH$_2$Ar wherein Ar is pyridinyl substituted with a cyano group;
A is —CH$_2$O—;
R$^2$ is

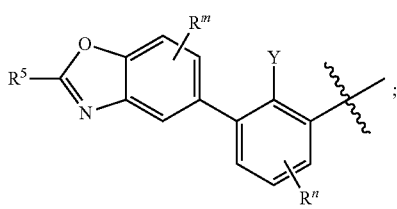

Y is selected from hydrogen and C$_1$alkyl;
R″ is selected from hydrogen and C$_1$alkyl;
R$^5$ is a six- to eight-membered monocyclic or bicyclic ring containing one nitrogen atom and zero double bonds, wherein the ring is optionally substituted with one substituent selected from C$_1$alkyl, di(C$_1$-C$_4$)alkylamino, amino, carboxyC$_1$-C$_4$alkyl, and C$_3$-C$_4$cycloalkyl; and
R$^4$ is —(CH$_2$)NR$^q$R$^8$; wherein
R$^q$ is selected from hydrogen and C$_1$alkyl;

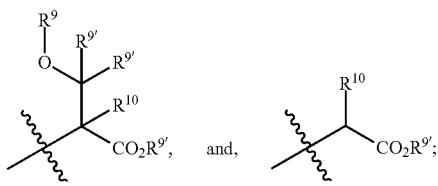

R$^8$ is selected from
R$^9$ is selected from hydrogen and C$_1$alkyl;
each R$^{9'}$ is independently selected from hydrogen and C$_1$alkyl; and
R$^{10}$ is selected from hydrogen and C$_1$-C$_4$alkyl; or
R$^8$ and R$^q$, together with the nitrogen atom to which they are attached, form a ring which is

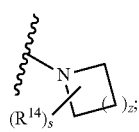

wherein
s is 1;
z is 3; and
R$^{14}$ is carboxy.

In a sixth embodiment of the first aspect the present disclosure provides a compound of formula (I), or a pharmaceutically acceptable salt thereof, wherein m is 1;
Z is —O(CH$_2$)$_n$Ar;
n is 1;
Ar is pyridinyl substituted with one cyano group;
A is —CH$_2$O—;
R$^2$ is selected from

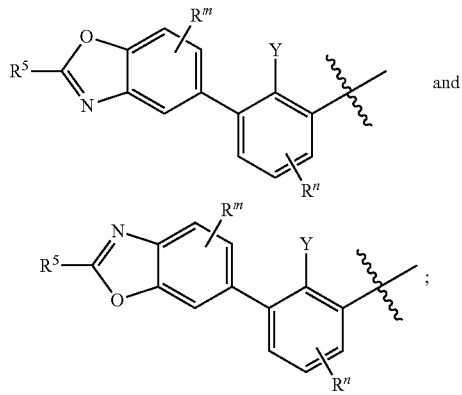

wherein
R$^m$ and R$^n$ are independently selected from hydrogen and C$_1$-C$_3$alkyl;
Y is selected from hydrogen and C$_1$-C$_3$alkyl;
R$^5$ is a five- to eight-membered monocyclic or bicyclic ring optionally containing one or two heteroatoms independently selected from nitrogen and oxygen and containing zero, one, two, or three double bonds, wherein said ring is optionally substituted with one group selected from C$_1$-C$_4$alkyl, di(C$_1$-C$_4$)alkylamino, amino, carboxyC$_1$-C$_4$alkyl, and C$_3$-C$_4$cycloalkyl;
R$^3$ is halo;
R$^4$ is selected from —CH$_2$OH, —CHO and —(CH$_2$)$_n$NR$^q$R$^8$; wherein
n is 1;
R$^q$ is selected from hydrogen and C$_1$-C$_4$alkyl;
R$^8$ is selected from

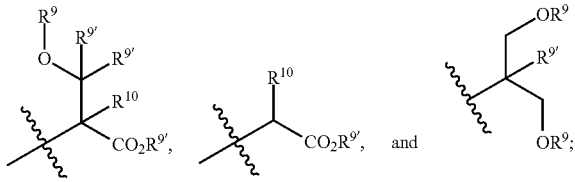

R$^9$ is selected from hydrogen and C$_1$alkyl;
each R$^{9'}$ is independently selected from hydrogen and C$_1$-C$_3$alkyl; and
R$^{10}$ is selected from hydrogen and C$_1$-C$_4$alkyl; or
R$^8$ and R$^q$, together with the nitrogen atom to which they are attached, form a ring which is

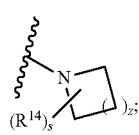

wherein
s is 1;
z is 3; and
R$^{14}$ is carboxy.

In a second aspect the present disclosure provides a pharmaceutical composition comprising a compound of formula (I), or a pharmaceutically acceptable salt thereof, and a pharmaceutically acceptable carrier.

In a third aspect the present disclosure provides a method of enhancing, stimulating, modulating and/or increasing the immune response in a subject in need thereof, said method comprising administering to the subject a therapeutically effective amount of a compound of formula (I), or a pharmaceutically acceptable salt thereof. In a first embodiment of the third aspect the method further comprises administering an additional agent prior to, after, or simultaneously with the compound of formula (I), or the pharmaceutically acceptable salt thereof. In a second embodiment the additional agent is an antimicrobial agent, an antiviral agent, a cytotoxic agent, a gene expression modulatory agent, and/or an immune response modifier.

In a fourth aspect the present disclosure provides a method of inhibiting growth, proliferation, or metastasis of cancer cells in a subject in need thereof, said method comprising administering to the subject a therapeutically effective amount of a compound of formula (I), or a pharmaceutically acceptable salt. In a first embodiment the cancer is selected from melanoma, renal cell carcinoma, squamous non-small cell lung cancer (NSCLC), non-squamous NSCLC, colorectal cancer, castration-resistant prostate cancer, ovarian cancer, gastric cancer, hepatocellular carcinoma, pancreatic carcinoma, squamous cell carcinoma of the head and neck, carcinomas of the esophagus, gastro-intestinal tract and breast, and a hematological malignancy.

In a fifth aspect the present disclosure provides a method of treating an infectious disease in a subject in need thereof, the method comprising administering to the subject a therapeutically effective amount of a compound of formula (I), or a pharmaceutically acceptable salt thereof. In a first embodiment of the fifth aspect the infectious disease is caused by a virus. In a second embodiment the virus is selected from HIV, Hepatitis A, Hepatitis B, Hepatitis C, Hepatitis D, herpes viruses, papillomaviruses, and influenza.

In a sixth aspect the present disclosure provides a method of treating septic shock in a subject in need thereof, the method comprising administering to the subject a therapeutically effective amount of a compound of formula (I), or a pharmaceutically acceptable salt thereof.

In a seventh aspect the present disclosure provides a compound of formula (I) or a pharmaceutically acceptable salt thereof for use as a medicament.

In another aspect the present disclosure provides a compound of formula (II),

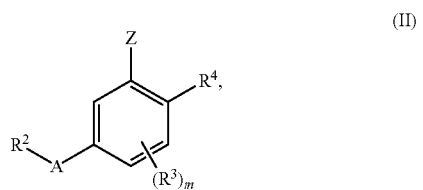

(II)

or a pharmaceutically acceptable salt thereof, wherein:
m is 0, 1, or 2;
Z is —O(CH$_2$)$_n$Ar;
n is 1, 2, 3, or 4;
Ar is selected from phenyl and pyridinyl, wherein each ring is optionally substituted with 1, 2, 3, or 4 substituents independently selected from C$_1$-C$_4$alkoxy, C$_1$-C$_4$alkyl, amido, carboxy, cyano, formyl, halo, haloC$_1$-C$_4$alkyl, haloC$_1$-C$_4$alkoxy, and nitro;

A is selected from —CH$_2$O—, —OCH$_2$—, —(CH$_2$)$_2$—, —CH=CH—, —C(O)NH—, and —NHC(O)—, wherein each group is drawn with its left side attached to R$^2$ and its right side attached to the phenyl ring;

R$^2$ is selected from

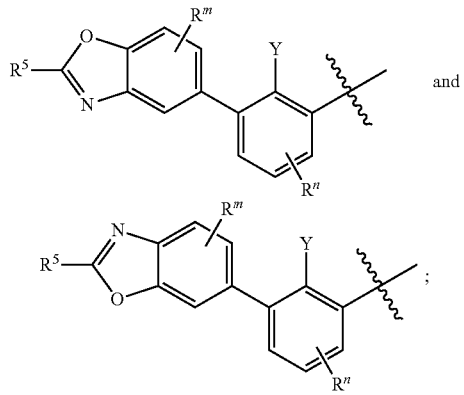

wherein
R$^m$ and R$^n$ are independently selected from hydrogen, C$_1$-C$_3$alkyl, and halo;
Y is selected from hydrogen, C$_1$-C$_3$alkoxy, C$_1$-C$_3$alkyl, cyano, and halo;
R$^5$ is a three- to ten-membered monocyclic or bicyclic ring optionally containing one or two heteroatoms independently selected from nitrogen and oxygen and containing zero, one, two, or three double bonds, wherein said ring is optionally substituted with one, two, or three groups independently selected from C$_1$-C$_3$alkoxy, C$_1$-C$_3$alkoxyC$_1$-C$_4$alkyl, C$_1$-C$_4$alkyl, di(C$_1$-C$_4$)alkylamino, amino, aminoC$_1$-C$_4$alkyl, carboxy, carboxyC$_1$-C$_4$alkyl, and C$_3$-C$_4$cycloalkyl;
each R$^3$ is independently selected from C$_1$-C$_4$alkyl, cyano, halo, and haloC$_1$-C$_4$alkyl;
R$^4$ is selected from —CH$_2$OH, —CHO and —(CH$_2$)$_n$NR$^q$R$^8$; wherein
n is 1, 2, 3, or 4;
R$^q$ is selected from hydrogen and C$_1$-C$_4$alkyl;
R$^8$ is selected from hydrogen, C$_1$-C$_4$alkyl, —(CH$_2$)$_n$N(CH$_3$)$_2$,

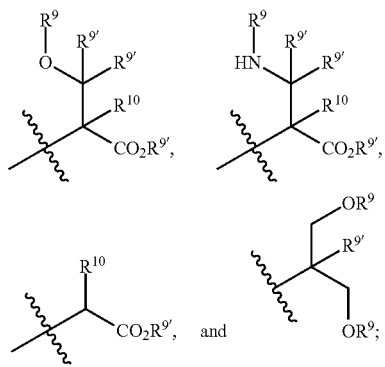

$R^9$ is selected from hydrogen and $C_1$alkyl;

each $R^{9'}$ is independently selected from hydrogen and $C_1$-$C_3$alkyl;

$R^{10}$ is selected from hydrogen and $C_1$-$C_4$alkyl; or $R^8$ and $R^q$, together with the nitrogen atom to which they are attached, form a ring which is

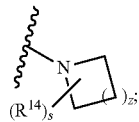

wherein s is 0, 1, or 2;

z is 1, 2, or 3; and each $R^{14}$ is independently selected from $C_1$-$C_4$alkoxycarbonyl, $C_1$-$C_4$alkyl, carboxy, halo, hydroxy, and hydroxy$C_1$-$C_4$alkyl.

Unless specifically stated otherwise herein, references made in the singular may also include the plural. For example, "a" and "an" may refer to either one, or one or more.

As used herein, the phase "compound(s) or pharmaceutically acceptable salts thereof" refers to at least one compound, at least one salt of the compounds, or a combination thereof. For example, compounds of formula (I) or pharmaceutically acceptable salts thereof includes a compound of formula (I); two compounds of formula (I); a salt of a compound of formula (I); a compound of formula (I) and one or more salts of the compound of formula (I); and two or more salts of a compound of formula (I).

Unless otherwise indicated, any atom with unsatisfied valences is assumed to have hydrogen atoms sufficient to satisfy the valences.

Throughout the specification, groups and substituents thereof may be chosen by one skilled in the field to provide stable moieties and compounds.

Listed below are definitions of various terms used to describe the present disclosure. These definitions apply to the terms as they are used throughout the specification (unless they are otherwise limited in specific instances) either individually or as part of a larger group. The definitions set forth herein take precedence over definitions set forth in any patent, patent application, and/or patent application publication incorporated herein by reference.

As used herein, the singular forms "a", "an", and "the" include plural reference unless the context clearly dictates otherwise.

The bicyclic rings of the present disclosure may be monocyclic or fused, spirocyclic, or bridged bicyclic structures.

The term "$C_1$-$C_3$alkoxy," as used herein, refers to a $C_1$-$C_3$alkyl group attached to the parent molecular moiety through an oxygen atom.

The term "$C_1$-$C_3$alkoxy$C_1$-$C_4$alkyl," as used herein, refers to a $C_1$-$C_3$alkoxy group attached to the parent molecular moiety through a $C_1$-$C_4$alkyl group.

The term "$C_1$-$C_4$alkoxy," as used herein, refers to a $C_1$-$C_4$alkyl group attached to the parent molecular moiety through an oxygen atom.

The term "$C_1$-$C_4$alkoxycarbonyl," as used herein, refers to a $C_1$-$C_4$alkoxy group attached to the parent molecular group through a carbonyl group.

The term "$C_1$-$C_3$alkyl," as used herein, refers to a group derived from a straight or branched chain saturated hydrocarbon containing from one to three carbon atoms.

The term "$C_1$-$C_4$alkyl," as used herein, refers to a group derived from a straight or branched chain saturated hydrocarbon containing from one to four carbon atoms.

The term "$C_1$-$C_6$alkyl," as used herein, refers to a group derived from a straight or branched chain saturated hydrocarbon containing from one to six carbon atoms.

The term "$C_1$-$C_4$alkylamino," as used herein, refers —NHR, wherein R is a $C_1$-$C_4$alkyl group.

The term "amido," as used herein, refers to —C(O)NH$_2$.

The term "amino$C_1$-$C_4$alkyl," as used herein, refers to an amino group attached to the parent molecular moiety through a $C_1$-$C_4$alkyl group.

The term "carbonyl," as used herein, refers to —C(O)—.

The term "carboxy," as used herein, refers to —CO$_2$H.

The term "carboxy$C_1$-$C_4$alkyl," as used herein, refers to a carboxy group attached to the parent molecular moiety through a $C_1$-$C_4$alkyl group.

The term "cyano," as used herein, refers to —CN.

The term "$C_3$-$C_6$cycloalkyl," as used herein, refers to a saturated monocyclic hydrocarbon ring system having three or four carbon atoms and zero heteroatoms.

The term "di($C_1$-$C_4$alkyl)amino," as used herein, refers to —NR$_2$, wherein each R is a $C_1$-$C_4$alkyl group. The R groups may be the same or different.

The term "formyl," as used herein, refers to —C(O)H.

The terms "halo" and "halogen," as used herein, refer to F, Cl, Br, or I.

The term "halo$C_1$-$C_4$alkoxy," as used herein, refers to a halo$C_1$-$C_4$alkyl group attached to the parent molecular moiety through an oxygen atom.

The term "halo$C_1$-$C_4$alkyl," as used herein, refers to a $C_1$-$C_4$alkyl group substituted with one, two, or three halogen atoms.

The term "hydroxy," as used herein, refers to —OH.

The term "hydroxy$C_1$-$C_4$alkyl," as used herein, refers to a hydroxy group attached to the parent molecular moiety through a $C_1$-$C_4$alkyl group.

The term "nitro," as used herein, refers to —NO$_2$.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of formula (I) can form salts which are also within the scope of this disclosure. Unless otherwise indicated, reference to an inventive compound is understood to include reference to one or more salts thereof. The term "salt(s)" denotes acidic and/or basic salts formed with inorganic and/or organic acids and bases. In addition, the term "salt(s) may include zwitterions (inner salts), e.g., when a compound of formula (I) contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the disclosure. Salts of the compounds of the formula (I) may be formed, for example, by reacting a compound of the formula (I) with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, maleates (formed with maleic acid), 2-hydroxyethanesulfonates, lactates, methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate salts.

Various forms of prodrugs are well known in the art and are described in:
a) *The Practice of Medicinal Chemistry*, Camille G. Wermuth et al., Ch 31, (Academic Press, 1996);
b) *Design of Prodrugs*, edited by H. Bundgaard, (Elsevier, 1985);
c) *A Textbook of Drug Design and Development*, P. Krogsgaard-Larson and H. Bundgaard, eds. Ch 5, pgs 113-191 (Harwood Academic Publishers, 1991); and
d) *Hydrolysis in Drug and Prodrug Metabolism*, Bernard Testa and Joachim M. Mayer, (Wiley-VCH, 2003).

In addition, compounds of formula (I), subsequent to their preparation, can be isolated and purified to obtain a composition containing an amount by weight equal to or greater than 99% of a compound of formula (I) ("substantially pure"), which is then used or formulated as described herein. Such "substantially pure" compounds of formula (I) are also contemplated herein as part of the present disclosure.

"Stable compound" and "stable structure" are meant to indicate a compound that is sufficiently robust to survive isolation to a useful degree of purity from a reaction mixture, and formulation into an efficacious therapeutic agent. The present disclosure is intended to embody stable compounds.

"Therapeutically effective amount" is intended to include an amount of a compound of the present disclosure alone or an amount of the combination of compounds claimed or an amount of a compound of the present disclosure in combination with other active ingredients effective to inhibit PD-1/PD-L1 protein/protein and/or CD80/PD-L1 protein/protein interactions, or effective to treat or prevent cancer or infectious disease, such as septic shock, HIV or Hepatitis B, Hepatitis C, and Hepatitis D.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The compounds of the present disclosure are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}$C and $^{14}$C. Isotopically-labeled compounds of the disclosure can generally be prepared by conventional techniques known to those skilled in the art or by processes analogous to those described herein, using an appropriate isotopically-labeled reagent in place of the non-labeled reagent otherwise employed. For example, methyl (—CH$_3$) also includes deuterated methyl groups such as —CD$_3$.

Compounds in accordance with formula (I) and/or pharmaceutically acceptable salts thereof can be administered by any means suitable for the condition to be treated, which can depend on the need for site-specific treatment or quantity of formula (I) compound to be delivered. Also embraced within this disclosure is a class of pharmaceutical compositions comprising a compound of formula (I) and/or pharmaceutically acceptable salts thereof; and one or more non-toxic, pharmaceutically-acceptable carriers and/or diluents and/or adjuvants (collectively referred to herein as "carrier" materials) and, if desired, other active ingredients. The compounds of formula (I) may be administered by any suitable route, preferably in the form of a pharmaceutical composition adapted to such a route, and in a dose effective for the treatment intended. The compounds and compositions of the present disclosure may, for example, be administered orally, mucosally, rectally, or parentally including intravascularly, intravenously, intraperitoneally, subcutaneously, intramuscularly, and intrasternally in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g. magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 0.1 to 1000 mg, preferably from about 0.25 to 250 mg, and more preferably from about 0.5 to 100 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, liquid capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the disclosure can contain at least one agent selected from sweetening agents, flavoring agents, coloring agents, demulcents, antioxidants, and preserving agents.

A tablet can, for example, be prepared by admixing at least one compound of formula (I) and/or at least one pharmaceutically acceptable salt thereof with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium crosscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of formula (I) and/or at least one salt thereof with at least one inert solid diluent, such as, for example, calcium carbonate; calcium phosphate; and kaolin.

Soft gelatin capsules can, for example, be prepared by mixing at least one compound of formula (I) and/or at least one pharmaceutically acceptable salt thereof with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of formula (I) and/or at least one pharmaceutically acceptable salt thereof with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of formula (I) and/or at least one pharmaceutically acceptable salt thereof in either a vegetable oil, such as, for example, arachis oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an anti-oxidant, such as, for example, butylated hydroxyanisol, and alpha-tocopherol.

Dispersible powders and granules can, for example, be prepared by admixing at least one compound of formula (I) and/or at least one pharmaceutically acceptable salt thereof with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of formula (I) and/or at least one pharmaceutically acceptable salt thereof can, for example, be prepared as an oil-in-water emulsion. The oily phase of the emulsions comprising compounds of formula (I) may be constituted from known ingredients in a known manner. The oil phase can be provided by, but is not limited to, for example, a vegetable oil, such as, for example, olive oil and arachis oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present disclosure include Tween 60, Span 80, cetostearyl alcohol, myristyl alcohol, glyceryl monostearate, sodium lauryl sulfate, glyceryl distearate alone or with a wax, or other materials well known in the art.

The compounds of formula (I) and/or at least one pharmaceutically acceptable salt thereof can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (i.e. propylene glycol) or micellar solubilization (i.e. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of formula (I) in an oily phase, such as, for example, a mixture of soybean oil and lecithin; 2) combining the formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this disclosure include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutically active compounds of this disclosure can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The amounts of compounds that are administered and the dosage regimen for treating a disease condition with the compounds and/or compositions of this disclosure depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.0025 and about 50 mg/kg body weight and most preferably between about 0.005 to 10 mg/kg body weight, may be appropriate. The daily dose can be administered in one to four doses per day. Other dosing schedules include one dose per week and one dose per two day cycle.

For therapeutic purposes, the active compounds of this disclosure are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this disclosure comprise at least one compound of formula (I) and/or at least one pharmaceutically acceptable salt thereof, and optionally an additional agent selected from any pharmaceutically acceptable carrier, adjuvant, and vehicle. Alternate compositions of this disclosure comprise a compound of the formula (I) described herein, or a prodrug thereof, and a pharmaceutically acceptable carrier, adjuvant, or vehicle.

The compounds of the disclosure inhibit the PD-1/PD-L1 protein/protein resulting in a PD-L1 blockade. The blockade of PD-L1 can enhance the immune response to cancerous cells and infectious diseases in mammals, including humans.

In one aspect, the present disclosure relates to treatment of a subject in vivo using a compound of formula (I) or a salt thereof such that growth of cancerous tumors is inhibited. A compound of formula (I) or a salt thereof may be used alone to inhibit the growth of cancerous tumors. Alternatively, a compound of formula (I) or a salt thereof may be used in conjunction with other immunogenic agents or standard cancer treatments, as described below.

In one embodiment, the disclosure provides a method of inhibiting growth of tumor cells in a subject, comprising administering to the subject a therapeutically effective amount of a compound of formula (I) or a salt thereof.

In one embodiment, a method is provided for treating cancer comprising administering to a patient in need thereof, a therapeutically effective amount of a compound of formula (I) or a salt thereof. Examples of cancers include those whose growth may be inhibited using compounds of the disclosure include cancers typically responsive to immunotherapy. Non-limiting examples of preferred cancers for treatment include melanoma (e.g., metastatic malignant melanoma), renal cancer (e.g. clear cell carcinoma), prostate cancer (e.g. hormone refractory prostate adenocarcinoma), breast cancer, colon cancer and lung cancer (e.g. non-small cell lung cancer). Additionally, the disclosure includes refractory or recurrent malignancies whose growth may be inhibited using the compounds of the disclosure.

Examples of other cancers that may be treated using the methods of the disclosure include bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or urethra, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The present disclosure is also useful for treatment of metastatic cancers, especially metastatic cancers that express PD-L1 (Iwai et al. (2005) *Int. Immunol.* 17:133-144).

Optionally, the compounds of formula (I) or salts thereof can be combined with another immunogenic agent, such as cancerous cells, purified tumor antigens (including recombinant proteins, peptides, and carbohydrate molecules), cells, and cells transfected with genes encoding immune stimulating cytokines (He et al (2004) *J. Immunol.* 173: 4919-28). Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF.

In humans, some tumors have been shown to be immunogenic such as melanomas. It is anticipated that by raising the threshold of T cell activation by PD-L1 blockade, tumor responses are expected to be activated in the host.

The PD-L1 blockade can be combined with a vaccination protocol. Many experimental strategies for vaccination against tumors have been devised (see Rosenberg, S., 2000, Development of Cancer Vaccines, ASCO Educational Book Spring: 60-62; Logothetis, C., 2000, ASCO Educational Book Spring: 300-302; Khayat, D. 2000, ASCO Educational Book Spring: 414-428; Foon, K. 2000, ASCO Educational Book Spring: 730-738; see also Restifo, N. and Sznol, M., Cancer Vaccines, Ch. 61, pp. 3023-3043 in DeVita, V. et al. (eds.), 1997, Cancer: Principles and Practice of Oncology. Fifth Edition). In one of these strategies, a vaccine is prepared using autologous or allogenenic tumor cells. These cellular vaccines have been shown to be most effective when the tumor cells are transduced to express GM-CSF. GM-CSF has been shown to be a potent activator of antigen presentation for tumor vaccination (Dranoff et al. (1993) Proc. Natl. Acad. Sci. U.S.A. 90: 3539-43).

The study of gene expression and large scale gene expression patterns in various tumors has led to the definition of so called tumor specific antigens (Rosenberg, S A (1999) Immunity 10: 281-7). In many cases, these tumor specific antigens are differentiation antigens expressed in the tumors and in the cell from which the tumor arose, for example melanocyte antigens gp100, MAGE antigens, and Trp-2. More importantly, many of these antigens can be shown to be the targets of tumor specific T cells found in the host. PD-L1 blockade may be used in conjunction with a collection of recombinant proteins and/or peptides expressed in a tumor in order to generate an immune response to these proteins. These proteins are normally viewed by the immune system as self antigens and are therefore tolerant to them. The tumor antigen may also include the protein telomerase, which is required for the synthesis of telomeres of chromosomes and which is expressed in more than 85% of human cancers and in only a limited number of somatic tissues (Kim, N et al. (1994) Science 266: 2011-2013). (These somatic tissues may be protected from immune attack by various means). Tumor antigen may also be "neo-antigens" expressed in cancer cells because of somatic mutations that alter protein sequence or create fusion proteins between two unrelated sequences (ie. bcr-abl in the Philadelphia chromosome), or idiotype from B cell tumors.

Other tumor vaccines may include the proteins from viruses implicated in human cancers such a Human Papilloma Viruses (HPV), Hepatitis Viruses (HBV, HDV and HCV) and Kaposi's Herpes Sarcoma Virus (KHSV). Another form of tumor specific antigen which may be used in conjunction with PD-L1 blockade is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot, R & Srivastava, P (1995) Science 269:1585-1588; Tamura, Y. et al. (1997) Science 278:117-120).

Dendritic cells (DC) are potent antigen presenting cells that can be used to prime antigen-specific responses. DC's can be produced ex vivo and loaded with various protein and peptide antigens as well as tumor cell extracts (Nestle, F. et al. (1998) Nature Medicine 4: 328-332). DCs may also be transduced by genetic means to express these tumor antigens as well. DCs have also been fused directly to tumor cells for the purposes of immunization (Kugler, A. et al. (2000) Nature Medicine 6:332-336). As a method of vaccination, DC immunization may be effectively combined with PD-L1 blockade to activate more potent anti-tumor responses.

PD-L1 blockade may also be combined with standard cancer treatments. PD-L1 blockade may be effectively combined with chemotherapeutic regimes. In these instances, it may be possible to reduce the dose of chemotherapeutic reagent administered (Mokyr, M. et al. (1998) *Cancer Research* 58: 5301-5304). An example of such a combination is a compound of this disclosure in combination with dacarbazine for the treatment of melanoma. Another example of such a combination is a compound of this disclosure in combination with interleukin-2 (IL-2) for the treatment of melanoma. The scientific rationale behind the combined use of PD-L1 blockade and chemotherapy is that cell death, that is a consequence of the cytotoxic action of most chemotherapeutic compounds, should result in increased levels of tumor antigen in the antigen presentation pathway. Other combination therapies that may result in synergy with PD-L1 blockade through cell death are radiation, surgery, and hormone deprivation. Each of these protocols creates a source of tumor antigen in the host. Angiogenesis inhibitors may also be combined with PD-L1 blockade. Inhibition of angiogenesis leads to tumor cell death which may feed tumor antigen into host antigen presentation pathways.

The compounds of this disclosure can also be used in combination with bispecific compounds that target Fc alpha or Fc gamma receptor-expressing effectors cells to tumor cells (see, e.g., U.S. Pat. Nos. 5,922,845 and 5,837,243). Bispecific compounds can be used to target two separate antigens. For example anti-Fc receptor/anti tumor antigen (e.g., Her-2/neu) bispecific compounds have been used to target macrophages to sites of tumor. This targeting may more effectively activate tumor specific responses. The T cell arm of these responses would be augmented by the use of PD-L1 blockade. Alternatively, antigen may be delivered directly to DCs by the use of bispecific compounds which bind to tumor antigen and a dendritic cell specific cell surface marker.

Tumors evade host immune surveillance by a large variety of mechanisms. Many of these mechanisms may be overcome by the inactivation of proteins which are expressed by the tumors and which are immunosuppressive. These include among others TGF-beta (Kehrl, J. et al. (1986) *J. Exp. Med.* 163: 1037-1050), IL-10 (Howard, M. & O'Garra, A. (1992) *Immunology Today* 13: 198-200), and Fas ligand (Hahne, M. et al. (1996) *Science* 274: 1363-1365). Inhibitors that bind to and block each of these entities may be used in combination with the compounds of this disclosure to counteract the effects of the immunosuppressive agent and favor tumor immune responses by the host.

Compounds that activate host immune responsiveness can be used in combination with PD-L1 blockade. These include molecules on the surface of dendritic cells which activate DC function and antigen presentation. Anti-CD40 compounds are able to substitute effectively for T cell helper activity (Ridge, J. et al. (1998) *Nature* 393: 474-478) and can be used in conjunction with PD-L1 blockade (Ito, N. et al. (2000) *Immunobiology* 201 (5) 527-40). Activating compounds to T cell costimulatory molecules such as CTLA-4 (e.g., U.S. Pat. No. 5,811,097), OX-40 (Weinberg, A. et al. (2000) *Immunol* 164: 2160-2169), 4-1BB (Melero, I. et al. (1997) *Nature Medicine* 3: 682-685 (1997), and ICOS (Hutloff, A. et al. (1999) *Nature* 397: 262-266) may also provide for increased levels of T cell activation.

Bone marrow transplantation is currently being used to treat a variety of tumors of hematopoietic origin. While graft versus host disease is a consequence of this treatment, therapeutic benefit may be obtained from graft vs. tumor responses. PD-L1 blockade can be used to increase the effectiveness of the donor engrafted tumor specific T cells.

Other methods of the disclosure are used to treat patients who have been exposed to particular toxins or pathogens. Accordingly, another aspect of the disclosure provides a method of treating an infectious disease in a subject comprising administering to the subject a therapeutically effective amount of a compound of formula (I) or salts thereof.

Similar to its application to tumors as discussed above, the compound of formula (I) or salts thereof can be used alone, or as an adjuvant, in combination with vaccines, to stimulate the immune response to pathogens, toxins, and self-antigens. Examples of pathogens for which this therapeutic approach may be particularly useful, include pathogens for which there is currently no effective vaccine, or pathogens for which conventional vaccines are less than completely effective. These include, but are not limited to HIV, Hepatitis (A, B, C or D), Influenza, Herpes, Giardia, Malaria, *Leishmania, Staphylococcus aureus, Pseudomonas Aeruginosa*. PD-L1 blockade is particularly useful against established infections by agents such as HIV that present altered antigens over the course of the infections. These novel epitopes are recognized as foreign at the time of administration, thus provoking a strong T cell response that is not dampened by negative signals through PD-1.

Some examples of pathogenic viruses causing infections treatable by methods of the disclosure include HIV, hepatitis (A, B, C, or D), herpes viruses (e.g., VZV, HSV-1, HAV-6, HHv-7, HHV-8, HSV-2, CMV, and Epstein Barr virus), adenovirus, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Some examples of pathogenic bacteria causing infections treatable by methods of the disclosure include chlamydia, rickettsial bacteria, mycobacteria, staphylococci, streptococci, pneumonococci, meningococci and conococci, klebsiella, proteus, serratia, pseudomonas, legionella, diphtheria, salmonella, bacilli, cholera, tetanus, botulism, anthrax, plague, leptospirosis, and Lymes disease bacteria.

Some examples of pathogenic fungi causing infections treatable by methods of the disclosure include Candida (albicans, krusei, glabrata, tropicalis, etc.), Cryptococcus neoformans, Aspergillus (fumigatus, niger, etc.), Genus Mucorales (mucor, absidia, rhizophus), Sporothrix schenkii, Blastomyces dermatitidis, Paracoccidioides brasiliensis, Coccidioides immitis and Histoplasma capsulatum.

Some examples of pathogenic parasites causing infections treatable by methods of the disclosure include Entamoeba histolytica, Balantidium coli, Naegleriafowleri, Acanthamoeba sp., Giardia lambia, Cryptosporidium sp., Pneumocystis carinii, Plasmodium vivax, Babesia microti, Trypanosoma brucei, Trypanosoma cruzi, Leishmania donovani, Toxoplasma gondi, and Nippostrongylus brasiliensis. In all of the above methods, PD-L1 blockade can be combined with other forms of immunotherapy such as cytokine treatment (e.g., interferons, GM-CSF, G-CSF, IL-2), or bispecific antibody therapy, which provides for enhanced presentation of tumor antigens (see, e.g., Holliger (1993) *Proc. Natl. Acad. Sci. USA* 90:6444-6448; Poljak (1994) *Structure* 2:1121-1123), vaccines, or agents that modify gene expression.

The compounds of this disclosure may provoke and amplify autoimmune responses. Indeed, induction of antitumor responses using tumor cell and peptide vaccines reveals that many anti-tumor responses involve anti-self reactivities (depigmentation observed in anti-CTLA-4+GM-CSF-modified B 16 melanoma in van Elsas et al. supra; depigmentation in Trp-2 vaccinated mice (Overwijk, W. et al. (1999) *Proc. Natl. Acad. Sci. U.S.A.* 96: 2982-2987); autoimmune prostatitis evoked by TRAMP tumor cell vaccines (Hurwitz, A. (2000) supra), melanoma peptide antigen vaccination and vitilago observed in human clinical trials (Rosenberg, S A and White, D E (1996) *J. Immunother Emphasis Tumor Immunol* 19 (1): 81-4).

Therefore, it is possible to consider using anti-PD-L1 blockade in conjunction with various self proteins in order to devise vaccination protocols to efficiently generate immune responses against these self proteins for disease treatment. For example, Alzheimer's disease involves inappropriate accumulation of A.beta.peptide in amyloid deposits in the brain; antibody responses against amyloid are able to clear these amyloid deposits (Schenk et al., (1999) *Nature* 400: 173-177).

Other self proteins may also be used as targets such as IgE for the treatment of allergy and asthma, and TNF.alpha. for rheumatoid arthritis. Finally, antibody responses to various hormones may be induced by the use of a compound of formula (I) or salts thereof. Neutralizing antibody responses to reproductive hormones may be used for contraception. Neutralizing antibody response to hormones and other soluble factors that are required for the growth of particular tumors may also be considered as possible vaccination targets.

Analogous methods as described above for the use of anti-PD-L1 antibody can be used for induction of therapeutic autoimmune responses to treat patients having an inappropriate accumulation of other self-antigens, such as amyloid deposits, including A.beta. in Alzheimer's disease, cytokines such as TNF alpha, and IgE.

The compounds of this disclosure may be used to stimulate antigen-specific immune responses by co-administration of a compound of formula (I) or salts thereof with an antigen of interest (e.g., a vaccine). Accordingly, in another aspect the disclosure provides a method of enhancing an immune response to an antigen in a subject, comprising administering to the subject: (i) the antigen; and (ii) a compound of formula (I) or salts thereof, such that an immune response to the antigen in the subject is enhanced. The antigen can be, for example, a tumor antigen, a viral antigen, a bacterial antigen or an antigen from a pathogen. Non-limiting examples of such antigens include those discussed in the sections above, such as the tumor antigens (or tumor vaccines) discussed above, or antigens from the viruses, bacteria or other pathogens described above.

As previously described, the compounds of the disclosure can be co-administered with one or more other therapeutic agents, e.g., a cytotoxic agent, a radiotoxic agent or an immunosuppressive agent. The compounds of the disclosure can be administered before, after or concurrently with the other therapeutic agent or can be co-administered with other known therapies, e.g., an anti-cancer therapy, e.g., radiation. Such therapeutic agents include, among others, anti-neoplastic agents such as doxorubicin (adriamycin), cisplatin bleomycin sulfate, carmustine, chlorambucil, decarbazine and cyclophosphamide hydroxyurea which, by themselves, are only effective at levels which are toxic or subtoxic to a patient. Cisplatin is intravenously administered as a 100 mg/dose once every four weeks and adriamycin is intravenously administered as a 60-75 mg/mL dose once every 21 days. Co-administration of a compound of formula (I) or salts thereof, with chemotherapeutic agents provides two anti-cancer agents which operate via different mechanisms which yield a cytotoxic effect to human tumor cells. Such co-administration can solve problems due to development of resistance to drugs or a change in the antigenicity of the tumor cells which would render them unreactive with the antibody.

Also within the scope of the present disclosure are kits comprising a compound of formula (I) or salts thereof and instructions for use. The kit can further contain at least one additional reagent. Kits typically include a label indicating the intended use of the contents of the kit. The term label includes any writing, or recorded material supplied on or with the kit, or which otherwise accompanies the kit.

The above other therapeutic agents, when employed in combination with the compounds of the present disclosure, may be used, for example, in those amounts indicated in the Physicians' Desk Reference (PDR) or as otherwise determined by one of ordinary skill in the art. In the methods of the present disclosure, such other therapeutic agent(s) may be administered prior to, simultaneously with, or following the administration of the inventive compounds.

In one embodiment, the compounds of formula (I) inhibit the PD-1/PD-L1 interaction with $IC_{50}$ values of 20 μM or less, for example, from 0.48 to 20 μM, as measured by the PD-1/PD-L1 Homogenous Time-Resolved Fluorescence (HTRF) binding assay.

EXAMPLES

The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth hereinbelow, but rather is defined by the claims appended hereto.

As used in the present specification, the following terms have the meanings indicated: THF for tetrahydrofuran, EtOAc for ethyl acetate, DMF for N,N-dimethylformamide, DCE for 1,2-dichlorethane, DCM for dichloromethane, rt or RT or Rt for room temperature or retention time (context will dictate), EtOH for ethanol, min for minutes, h or hr for hours, and DMSO for dimethylsulfoxide.

Intermediate: 5-chloro-2-hydroxy-4-((2-methyl-3-(4, 4,5,5-tetramethyl-1,3,2-dioxaborolan-2-yl)benzyl) oxy)benzaldehyde

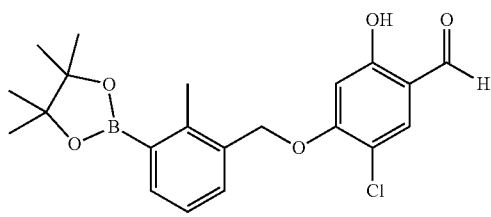 [SMILES: Cc1c(COc2cc(O)c(C=O)cc2Cl)cccc1B1OC(C)(C)C(C)(C)O1]

A solution of diisopropyl azodicarboxylate (1.793 g, 8.87 mmol) in THF (50 mL) was added dropwise to a solution of (2-methyl-3-(4,4,5,5-tetramethyl-1,3,2-dioxaborolan-2-yl) phenyl)methanol (2 g, 8.06 mmol), 5-chloro-2,4-dihydroxybenzaldehyde (1.391 g, 8.06 mmol), and triphenylphosphine (2.326 g, 8.87 mmol) in THF (50 mL) at 0° C. The resulting yellow solution was allowed to warm to room temperature and stirred overnight. The solvent was removed, and the residue was purified by silica gel column chromatography (Biotage 40m, 0 to 20% EtOAc/hexane) to give 1.95 g (57.1%) of 5-chloro-2-hydroxy-4-((2-methyl-3-(4,4,5,5-tetramethyl-1,3,2-dioxaborolan-2-yl)benzyl)oxy)benzaldehyde as a white solid. The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt (Retention time)=2.147 min., m/z 389.2 (M+H). $^1$H NMR (400 MHz, CHLOROFORM-d) δ ppm 11.45 (s, 1H), 9.72 (s, 1H), 7.83-7.79 (m, 1H), 7.57-7.53 (m, 2H), 7.28-7.23 (m, 1H), 6.62 (s, 1H), 5.19 (s, 2H), 2.59 (s, 3H), 1.40-1.37 (m, 12H).

Intermediate: 5-((4-chloro-2-formyl-5-((2-methyl-3-(4,4,5,5-tetramethyl-1,3,2-dioxaborolan-2-yl)benzyl)oxy)phenoxy)methyl)nicotinonitrile

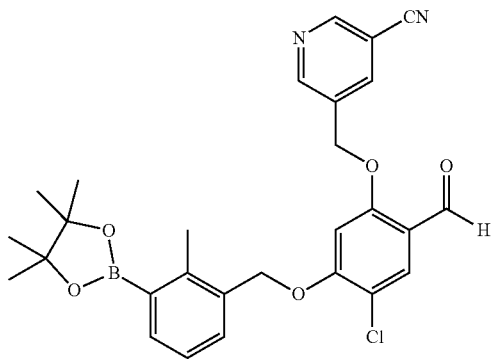 [SMILES: Cc1c(COc2cc(OCc3cncc(C#N)c3)c(C=O)cc2Cl)cccc1B1OC(C)(C)C(C)(C)O1]

A suspension of 5-chloro-2-hydroxy-4-((2-methyl-3-(4,4,5,5-tetramethyl-1,3,2-dioxaborolan-2-yl)benzyl)oxy)benzaldehyde (1.5 g, 3.73 mmol), 5-(chloromethyl)nicotinonitrile (0.739 g, 4.84 mmol), and cesium carbonate (1.760 g, 5.40 mmol) in DMF (15 mL) was stirred at room temperature overnight. The solvent was removed, and the residue was partitioned between dichloromethane and water. The aqueous phase was extracted once with dichloromethane. The organic extract was washed with brine and then dried over sodium sulfate. The drying agent was removed by filtration and the solvent removed in vacuuo. The resulting residue was purified by silica gel column chromatography (Biotage 40m, 0 to 50% EtOAc/hexanes) to give 1.48 g (77%) of 5-((4-chloro-2-formyl-5-((2-methyl-3-(4,4,5,5-tetramethyl-1,3,2-dioxaborolan-2-yl)benzyl)oxy)phenoxy)methyl)nicotinonitrile as a white solid. The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=2.147 min, m/z 505.3 (M+H). $^1$H NMR (500 MHz, CHLOROFORM-d) δ ppm 10.29 (s, 1H), 8.93 (d, J=1.6 Hz, 1H), 8.91 (d, J=1.7 Hz, 1H), 8.08 (s, 1H), 7.94 (s, 1H), 7.81 (d, J=7.3 Hz, 1H), 7.48 (d, J=7.4 Hz, 1H), 7.25 (t, J=7.5 Hz, 1H), 6.58 (s, 1H), 5.25 (s, 2H), 5.19 (s, 2H), 2.61 (s, 3H), 1.40 (s, 12H).

Intermediate: (S)-1-(5-chloro-2-((5-cyanopyridin-3-yl)methoxy)-4-((2-methyl-3-(4,4,5,5-tetramethyl-1,3,2-dioxaborolan-2-yl)benzyl)oxy)benzyl)piperidine-2-carboxylic Acid

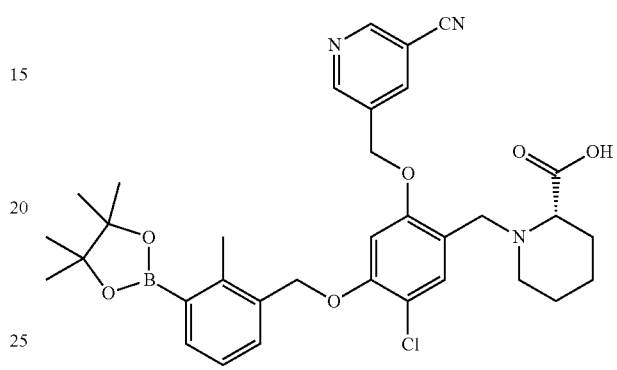

To a vial was added acetic acid (55 μL, 0.964 mmol), DCE (1,2-dichloroethane, 2.0 mL), ethanol (6.0 mL), THF (2.0 mL), 20 mgs of oven dried, ground, 4 Å molecular sieves, (S)-piperidine-2-carboxylic acid (124 mg, 0.964 mmol), 5-((4-chloro-2-formyl-5-((2-methyl-3-(4,4,5,5-tetramethyl-1,3,2-dioxaborolan-2-yl)benzyl)oxy)phenoxy)methyl)nicotinonitrile (250 mg, 0.482 mmol), and sodium cyanoborohydride (60.6 mgs, 0.964 mmol). The vial was capped and the mixture shaken overnight at room temperature. Volatiles were removed, and the resulting mixture diluted with 60 mL of DCM (dichloromethane), washed with water, brine, dried over sodium sulfate, filtered and evaporated to give 301.0 mgs of crude (S)-1-(5-chloro-2-((5-cyanopyridin-3-yl)methoxy)-4-((2-methyl-3-(4,4,5,5-tetramethyl-1,3,2-dioxaborolan-2-yl)benzyl)oxy)benzyl)piperidine-2-carboxylic acid.

For purification, the crude material was taken up in minimal acetonitrile and loaded onto an Isco 100 g C18 gold column, and purified using a Biotage Horizon employing acetonitrile/water/10 mM ammonium acetate where solvent A was 5% acetonitrile/95% water/10 mM ammonium acetate and solvent B was 5% water/95% acetonitrile/10 mM ammonium acetate at a gradient of 10-100% B. The product eluted at 55-60% B was collected. The LC/MS data was obtained on a Shimadzu analytical LCMS (ESI+) at 220 nm using the following set of conditions: Waters Aquity BEH 1.7 μm C18, 2.1×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.185 min., m/z 632.0 (M+H). $^1$H NMR (400 MHz, DMSO-d$_6$) δ 9.00 (m, 2H), 8.44 (m, 1H), 7.63 (d, J=7.3 Hz, 1H), 7.54 (d, J=6.8 Hz, 1H), 7.46-7.37 (m, 1H), 7.20 (m, 1H), 7.08 (m, 1H), 5.32 (br. s., 2H), 5.19 (m, 2H), 3.75 (d, J=13.7 Hz, 1H), 3.57 (d, J=13.7 Hz, 1H), 3.09 (m, 1H), 2.88 (m, 1H), 2.53 (s, 3H), 2.24 (m, 1H), 1.83-1.67 (m, 2H), 1.48 (m, 3H), 1.36 (m, 1H), 1.32 (m, 12H).

Intermediate: 5-bromo-2-(1-methylpiperidin-4-yl)benzo[d]oxazole

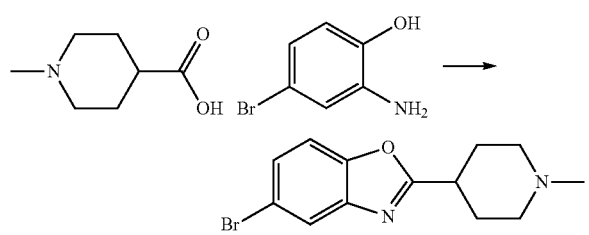

To 2-amino-4-bromophenol (200 mg, 1.064 mmol) and 1-methylpiperidine-4-carboxylic acid (152 mg, 1.064 mmol) in a sealed tube was added polyphosphoric acid (5 g). The vessel was sealed and the mixture heated for 3.5 hours at 190° C. The reaction mixture was cooled. To the mixture at 0° C. was added dropwise 6 mL of water and then aq. 10M NaOH until the pH reached ~8. To the thick purple mixture was added 30 mL of ethyl acetate. The product was filtered through celite, extracted, and washed with water, brine, dried over sodium sulfate, filtered and evaporated to give 244.8 mgs (74% yield) of 5-bromo-2-(1-methylpiperidin-4-yl)benzo[d]oxazole as a tan solid. The LC/MS data was obtained on a Shimadzu analytical LCMS (ESI+) at 220 nm using the following set of conditions: Waters Aquity BEH 1.7 mm C18, 2.1×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt (Retention time)=1.340 min., m/z 295.05, 297.00 (M+H), 95% purity. $^1$H NMR (500 MHz, DMSO-$d_6$) δ 7.95 (d, J=1.9 Hz, 1H), 7.68 (d, J=8.6 Hz, 1H), 7.53 (dd, J=8.6, 1.9 Hz, 1H), 3.02-2.93 (m, 1H), 2.79 (m, 2H), 2.19 (s, 3H), 2.10-2.01 (m, 4H), 1.87-1.77 (m, 2H).

Example 1001: (S)-1-(5-chloro-2-((5-cyanopyridin-3-yl)methoxy)-4-((2-methyl-3-(2-(1-methylpiperidin-4-yl)benzo[d]oxazol-5-yl)benzyl)oxy)benzyl)piperidine-2-carboxylic Acid

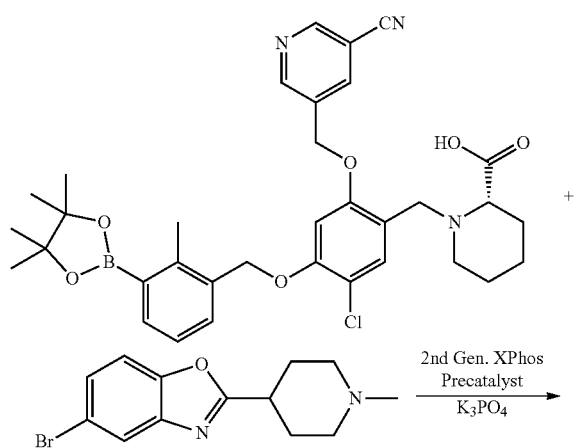

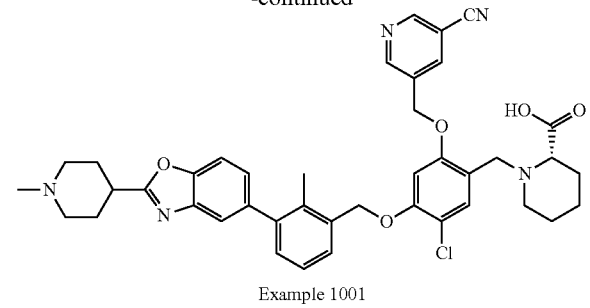

Example 1001

To a small sealed tube was added (S)-1-(5-chloro-2-((5-cyanopyridin-3-yl)methoxy)-4-((2-methyl-3-(4,4,5,5-tetramethyl-1,3,2-dioxaborolan-2-yl)benzyl)oxy)benzyl)piperidine-2-carboxylic acid (40 mg, 0.063 mmol), 5-bromo-2-(1-methylpiperidin-4-yl)benzo[d]oxazole (18.68 mg, 0.063 mmol), THF (3 mL), water (1 mL), potassium phosphate, tribasic (26.9 mg, 0.127 mmol), and finally second generation XPhos precatalyst (2.490 mg, 3.16 μmop. The vessel was sealed, the mixture de-gassed/flushed with nitrogen, and then heated overnight at 70° C. The crude material was purified via preparative LC/MS using the following conditions: Waters XBridge 5 μm C18, 19×200 mm where mobile phase A was 5:95 acetonitrile:water with 10 mM ammonium acetate and mobile phase B was 95:5 acetonitrile:water with 10 mM ammonium acetate at a gradient of 15-55% B over 20 minutes with a 5-minute hold at a flow rate of 20 mL/minute. Fractions containing the desired product were combined and dried via centrifugal evaporation. The yield of the product was 14.8 mg (31% yield), and its estimated purity by LCMS analysis was 96%.

Two analytical LC/MS injections were used to determine the final purity.

Injection 1 conditions: Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Injection 2 conditions: Waters Acquity UPLC BEH 1.7 μm C18, 2.1×50 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 3 minutes with a 0.75-minute hold at 100% B at a flow rate of 1.0 mL/minute at a UV wavelength of 220 nm.

Analysis condition 1: Retention time=1.550 min; ESI-MS (+) m/z=720.0 (M+H)

Analysis condition 2: Retention time=1.394 min; ESI-MS (+) m/z=720.1 (M+H)

$^1$H NMR (500 MHz, DMSO-$d_6$) δ 8.98 (s, 2H), 8.40 (s, 1H), 7.71 (d, J=8.5 Hz, 1H), 7.59 (s, 1H), 7.51 (d, J=7.3 Hz, 1H), 7.41 (s, 1H), 7.33-7.22 (m, 3H), 7.09 (s, 1H), 5.32 (m, 2H), 5.26 (s, 2H), 3.74 (d, J=13.7 Hz, 1H), 3.58 (d, J=13.7 Hz, 1H), 3.14 (d, J=6.1 Hz, 1H), 2.99 (m, 1H), 2.89 (m, 1H), 2.82 (m, 2H), 2.24 (s, 3H), 2.21 (s, 3H), 2.13-2.06 (m, 4H), 1.94-1.86 (m, 3H), 1.77 (m, 2H), 1.49 (m, 3H), 1.41-1.33 (m, 1H).

The following Intermediates and Examples were synthesized in an analogous manner.

Intermediate: 6-bromo-2-(1-methylpiperidin-4-yl)benzo[d]oxazole

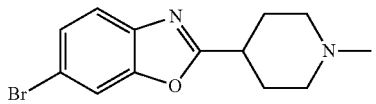 [SMILES: CN1CCC(c2nc3ccc(Br)cc3o2)CC1]

144.8 mgs (33% yield) of 6-bromo-2-(1-methylpiperidin-4-yl)benzo[d]oxazole was obtained as a tan solid. The LC/MS data was obtained on a Shimadzu analytical LCMS (ESI+) at 220 nm using the following set of conditions: Waters Aquity BEH 1.7 mm C18, 2.1×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.005 min., m/z 295.10, 297.10 (M+H), 75% purity. $^1$H NMR (500 MHz, CDCl$_3$) δ 7.66 (d, J=1.7 Hz, 1H), 7.55 (d, J=8.5 Hz, 1H), 7.44 (dd, J=8.5, 1.7 Hz, 1H), 3.02-2.85 (m, 3H), 2.34 (s, 3H), 2.24-2.14 (m, 4H), 2.11-1.97 (m, 2H).

Example 1002: (S)-1-(5-chloro-2-((5-cyanopyridin-3-yl)methoxy)-4-((2-methyl-3-(2-(1-methylpiperidin-4-yl)benzo[d]oxazol-6-yl)benzyl)oxy)benzyl)piperidine-2-carboxylic Acid

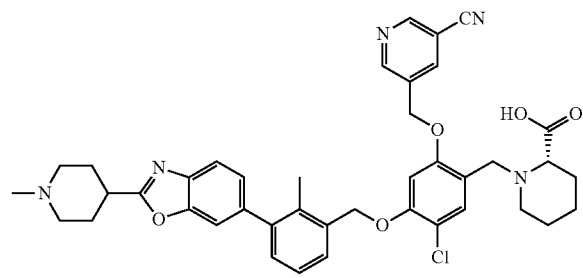 [SMILES: Cc1c(COc2cc(OCc3cncc(C#N)c3)c(CN3CCCC[C@H]3C(=O)O)cc2Cl)cccc1-c1ccc2nc(C3CCN(C)CC3)oc2c1]

The crude material was purified via preparative LC/MS using the following conditions: Waters XBridge 5 μm C18, 19×200 mm where mobile phase A was 5:95 acetonitrile:water with 10 mM ammonium acetate and mobile phase B was 95:5 acetonitrile:water with 10 mM ammonium acetate at a gradient of 30-70% B over 25 minutes with a 5-minute hold at a flow rate of 20 mL/minute. Fractions containing the desired product were combined and dried via centrifugal evaporation. The compound was further purified via preparative LC/MS using the following conditions: Waters XBridge 5 μm C18, 19×200 mm where mobile phase A was 5:95 acetonitrile:water with 10 mM ammonium acetate and mobile phase B was 95:5 acetonitrile:water with 10 mM ammonium acetate at a gradient of 12-52% B over 22 minutes with a 5-minute hold at a flow rate of 20 mL/minute. Fractions containing the desired product were combined and dried via centrifugal evaporation. The yield of the product was 11.7 mg (17% yield), and its estimated purity by LCMS analysis was 94%.

Two analytical LC/MS injections were used to determine the final purity.

Injection 1 conditions: Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Injection 2 conditions: Waters Acquity UPLC BEH 1.7 μm C18, 2.1×50 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 3 minutes with a 0.75-minute hold at 100% B at a flow rate of 1.0 mL/minute at a UV wavelength of 220 nm.

Analysis condition 1: Retention time=1.432 min; ESI-MS (+) m/z=720.1 (M+H)

Analysis condition 2: Retention time=1.462 min; ESI-MS (+) m/z=720.0 (M+H)

$^1$H NMR (500 MHz, DMSO-d$_6$) δ 8.97 (d, J=1.8 Hz, 2H), 8.40 (s, 1H), 7.73 (d, J=7.9 Hz, 1H), 7.59 (s, 1H), 7.50 (d, J=7.3 Hz, 1H), 7.42 (s, 1H), 7.33-7.21 (m, 3H), 7.08 (s, 1H), 5.32 (s, 2H), 5.26 (s, 2H), 3.77 (d, J=13.7 Hz, 1H), 3.60 (d, J=13.7 Hz, 1H), 3.17-3.09 (m, 2H), 3.05-2.95 (m, 1H), 2.92-2.86 (m, 1H), 2.81 (m, 2H), 2.28 (m, 1H), 2.24 (s, 3H), 2.21 (s, 3H), 2.13-2.03 (m, 4H), 1.90 (m, 1H), 1.77 (m, 2H), 1.49 (m, 3H), 1.37 (m, 1H).

Intermediate: (rac)-5-bromo-2-(1-methylpiperidin-3-yl)benzo[d]oxazole

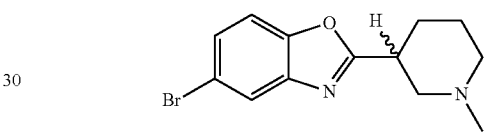

289.4 mgs (55% yield) of (rac)-5-bromo-2-(1-methylpiperidin-3-yl)benzo[d]oxazole was obtained as a red oil. The LC/MS data was obtained on a Shimadzu analytical LCMS (ESI+) at 220 nm using the following set of conditions: Waters Aquity BEH 1.7 mm C18, 2.1×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.032 min., m/z 295.10, 297.10 (M+H), 70% purity. $^1$H NMR (500 MHz, CDCl$_3$) δ 7.81 (d, J=1.9 Hz, 1H), 7.42 (dd, J=1.9, 8.7 Hz, 1H), 7.36 (d, J=8.7 Hz, 1H), 3.23 (m, 2H), 2.82 (m, 1H), 2.35 (s, 3H), 2.25-2.17 (m, 1H), 2.07 (m, 2H), 1.90-1.82 (m, 1H), 1.79-1.63 (m, 3H).

Example 1003: (2S)-1-(5-chloro-2-((5-cyanopyridin-3-yl)methoxy)-4-((2-methyl-3-(2-(1-methylpiperidin-3-yl)benzo[d]oxazol-5-yl)benzyl)oxy)benzyl)piperidine-2-carboxylic Acid

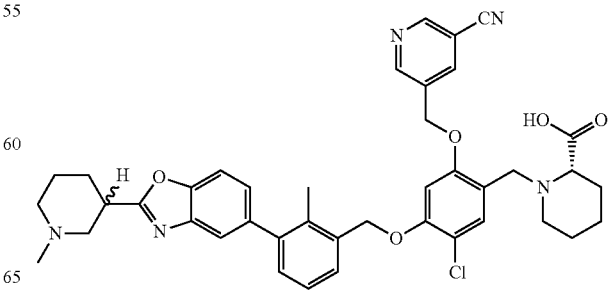

The crude material was purified via preparative LC/MS using the following conditions: Waters XBridge 5 μm C18, 19×200 mm where mobile phase A was 5:95 acetonitrile:water with 10 mM ammonium acetate and mobile phase B was 95:5 acetonitrile:water with 10 mM ammonium acetate at a gradient of 20-60% B over 20 minutes with a 5-minute hold at a flow rate of 20 mL/minute. Fractions containing the desired product were combined and dried via centrifugal evaporation. The yield of the product was 14.3 mg (21% yield), and its estimated purity by LCMS analysis was 97.0%.

Two analytical LC/MS injections were used to determine the final purity.

Injection 1 conditions: Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Injection 2 conditions: Waters Acquity UPLC BEH 1.7 μm C18, 2.1×50 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 3 minutes with a 0.75-minute hold at 100% B at a flow rate of 1.0 mL/minute at a UV wavelength of 220 nm.

Analysis condition 1: Retention time=1.636 min; ESI-MS (+) m/z=720.0 (M+H)

Analysis condition 2: Retention time=1.500 min; ESI-MS (+) m/z=720.0 (M+H)

$^1$H NMR (500 MHz, DMSO-$d_6$) δ 8.98 (s, 2H), 8.40 (s, 1H), 7.72 (d, J=8.2 Hz, 1H), 7.58 (s, 1H), 7.51 (d, J=7.6 Hz, 1H), 7.42 (s, 1H), 7.33-7.23 (m, 3H), 7.09 (s, 1H), 5.33 (d, J=2.7 Hz, 2H), 5.27 (s, 2H), 3.77 (d, J=13.7 Hz, 1H), 3.60 (d, J=13.7 Hz, 1H), 3.17-3.11 (m, 2H), 3.06 (m, 1H), 2.93-2.86 (m, 1H), 2.67 (m, 1H), 2.37 (t, J=10.4 Hz, 1H), 2.27 (m, 1H), 2.24 (br. s., 6H), 2.14-2.01 (m, 2H), 1.78 (m, 3H), 1.69-1.59 (m, 2H), 1.49 (m, 3H), 1.38 (m, 1H).

Intermediate: 5-bromo-2-(piperidin-4-yl)benzo[d]oxazole

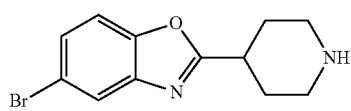

699.7 mgs (70% yield) of 5-bromo-2-(piperidin-4-yl)benzo[d]oxazole was obtained as a tan solid. The LC/MS data was obtained on a Shimadzu analytical LCMS (ESI+) at 220 nm using the following set of conditions: Waters Aquity BEH 1.7 mm C18, 2.1×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.027 min., m/z 281.10, 283.10 (M+H), 90% purity. $^1$H NMR (500 MHz, DMSO-$d_6$) δ 7.95 (d, J=1.9 Hz, 1H), 7.68 (d, J=8.7 Hz, 1H), 7.53 (dd, J=8.7, 1.9 Hz, 1H), 3.09 (s, 1H), 2.99 (dt, J=12.4, 3.6 Hz, 2H), 2.60 (td, J=11.9, 2.5 Hz, 2H), 1.99 (dd, J=12.7, 2.6 Hz, 2H), 1.75-1.61 (m, 2H).

Example 1004: (S)-1-(5-chloro-2-((5-cyanopyridin-3-yl)methoxy)-4-((2-methyl-3-(2-(piperidin-4-yl)benzo[d]oxazol-5-yl)benzyl)oxy)benzyl)piperidine-2-carboxylic Acid

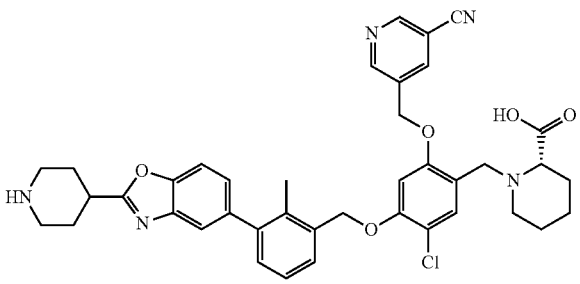 [SMILES: Cc1c(COc2cc(OCc3cncc(C#N)c3)c(CN3CCCC[C@H]3C(=O)O)cc2Cl)cccc1-c1ccc2oc(C3CCNCC3)nc2c1]

The crude material was purified via preparative LC/MS using the following conditions: Waters XBridge 5 μm C18, 19×200 mm where mobile phase A was 5:95 acetonitrile:water with 10 mM ammonium acetate and mobile phase B was 95:5 acetonitrile:water with 10 mM ammonium acetate at a gradient of 15-55% B over 20 minutes with a 5-minute hold at a flow rate of 20 mL/minute. Fractions containing the desired product were combined and dried via centrifugal evaporation. The yield of the product was 11.5 mg (20% yield), and its estimated purity by LCMS analysis was 97.1%.

Two analytical LC/MS injections were used to determine the final purity.

Injection 1 conditions: Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Injection 2 conditions: Waters Acquity UPLC BEH 1.7 μm C18, 2.1×50 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 3 minutes with a 0.75-minute hold at 100% B at a flow rate of 1.0 mL/minute at a UV wavelength of 220 nm.

Analysis condition 1: Retention time=1.348 min; ESI-MS (+) m/z=706.1 (M+H)

Analysis condition 2: Retention time=1.494 min; ESI-MS (+) m/z=706.0 (M+H)

$^1$H NMR (500 MHz, DMSO-$d_6$) δ 8.99 (m, 2H), 8.46 (s, 1H), 7.73 (d, J=8.2 Hz, 1H), 7.60 (d, J=1.2 Hz, 1H), 7.50 (d, J=7.0 Hz, 1H), 7.47 (s, 1H), 7.33-7.21 (m, 3H), 7.10 (s, 1H), 5.33 (s, 2H), 5.26 (s, 2H), 3.84 (d, J=13.4 Hz, 1H), 3.76-3.72 (m, 1H), 3.29-3.21 (m, 1H), 3.19-3.11 (m, 2H), 3.07-3.00 (m, 1H), 2.94-2.85 (m, 1H), 2.81 (m, 2H), 2.22 (m, 4H), 2.13 (m, 2H), 1.87-1.75 (m, 3H), 1.72-1.64 (m, 1H), 1.47 (m, 3H), 1.37-1.26 (m, 1H).

Intermediate: 5-bromo-2-(1-cyclopropylpiperidin-4-yl)benzo[d]oxazole

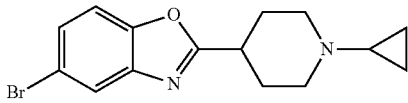 [SMILES: Brc1ccc2oc(C3CCN(C4CC4)CC3)nc2c1]

283.4 mgs (46% yield) of 5-bromo-2-(1-cyclopropylpiperidin-4-yl)benzo[d]oxazole was obtained as a tan solid. The LC/MS data was obtained on a Shimadzu analytical LCMS (ESI+) at 220 nm using the following set of conditions: Waters Aquity BEH 1.7 mm C18, 2.1×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.049 min., m/z 321.15, 323.10 (M+H), 70% purity. $^1$H NMR (500 MHz, DMSO-d$_6$) δ 7.95 (d, J=1.9 Hz, 1H), 7.68 (d, J=8.6 Hz 1H), 7.53 (dd, J=8.6, 1.9 Hz, 1H), 3.08-2.93 (m, 3H), 2.34 (td, J=11.5, 2.4 Hz, 2H), 2.11-2.04 (m, 2H), 1.80-1.59 (m, 3H), 0.47-0.38 (m, 2H), 0.35-0.28 (m, 2H).

Example 1005: (S)-1-(5-chloro-2-((5-cyanopyridin-3-yl)methoxy)-4-((3-(2-(1-cyclopropylpiperidin-4-yl)benzo[d]oxazol-5-yl)-2-methylbenzyl)oxy)benzyl)piperidine-2-carboxylic Acid

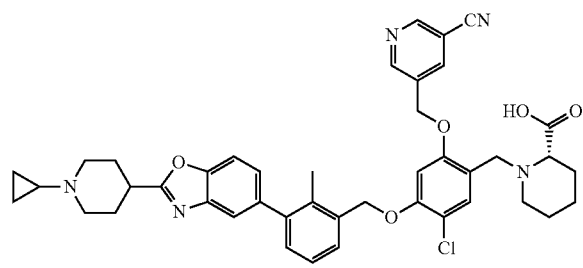 [SMILES: Cc1c(COc2cc(OCc3cncc(C#N)c3)c(CN3CCCC[C@H]3C(=O)O)cc2Cl)cccc1-c1ccc2oc(C3CCN(C4CC4)CC3)nc2c1]

The crude material was purified via preparative HPLC using the following conditions: Waters XBridge 5 μm C18, 30×100 mm where mobile phase A was 5:95 acetonitrile:water with 10 mM ammonium acetate and mobile phase B was 95:5 acetonitrile:water with 10 mM ammonium acetate at a complex gradient of 30-50% B over 25 minutes with a 10-minute hold at 50% B then 50-100% B over 10 minutes at a flow rate of 30 mL/minute. Fractions containing the desired product were evaporated. The yield of the product was 21.5 mg (18% yield), and its estimated purity by LCMS analysis was 99%.
Two analytical LC/MS injections were used to determine the final purity.
Injection 1 conditions: Waters Xbridge 3.5 μm C18, 3.0×150 mm where mobile phase A was 5:95 acetonitrile:water with 10 mM ammonium acetate; mobile phase B was 95:5 acetonitrile:water with 10 mM ammonium acetate at a temperature of 50° C. at a gradient of 10-100% B over 15 minutes with a 5-minute hold at 100% B at a flow rate of 0.5 mL/minute at a UV wavelength of 220 nm.
Injection 2 conditions: Waters Sunfire 3.5 μm C18, 3.0×150 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 10-100% B over 15 minutes with a 5-minute hold at 100% B at a flow rate of 0.5 mL/minute at a UV wavelength of 220 nm.
Analysis condition 1: Retention time=14.83 min; 99% purity.
Analysis condition 2: Retention time=6.09 min; 99% purity.
The LC/MS data was obtained on a Shimadzu analytical LCMS (ESI+) at 220 nm using the following set of conditions: Waters Aquity BEH 1.7 μm C18, 2.1×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.129 min., m/z 746.20 & 748.20 (M+H). $^1$H NMR (500 MHz, CD$_3$OD) δ 8.96 (s, 1H), 8.93 (s, 1H), 8.40 (s, 1H), 7.67 (m, 2H), 7.57 (s, 1H), 7.54-7.46 (m, 1H), 7.32 (m, 3H), 7.06 (s, 1H), 5.39 (s, 2H), 5.34 (s, 2H), 4.51-4.40 (m, 1H), 4.40-4.23 (m, 1H), 3.59-3.45 (m, 1H), 3.28-3.10 (m, 3H), 3.03-2.85 (m, 1H), 2.64-2.44 (m, 2H), 2.28 (m, 6H), 1.98 (m, 2H), 1.92-1.76 (m, 4H), 1.76-1.62 (m, 1H), 1.62-1.44 (m, 1H), 1.39-1.23 (m, 1H), 0.51 (m, 4H).

Intermediate: 2-(8-azabicyclo[3.2.1]octan-3-yl)-5-bromobenzo[d]oxazole

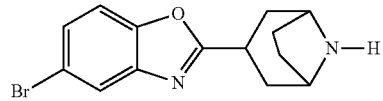 [SMILES: Brc1ccc2oc(C3CC4CCC(C3)N4)nc2c1]

110.7 mgs of 2-(8-azabicyclo[3.2.1]octan-3-yl)-5-bromobenzo[d]oxazole (38% yield) was obtained as a tan solid. The LC/MS data was obtained on a Shimadzu analytical LCMS (ESI+) at 220 nm using the following set of conditions: Waters Aquity BEH 1.7 μm C18, 2.1×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.140 min., m/z 307.10 & 309.10 (M+H), 100% purity. $^1$H NMR (500 MHz, DMSO-d$_6$) δ 7.96 (d, J=1.9 Hz, 1H), 7.69 (d, J=8.7 Hz, 1H), 7.54 (dd, J=8.7, 1.9 Hz, 1H), 3.96 (m, 2H), 3.55 (m, 1H), 2.20-2.04 (m, 4H), 2.02-1.90 (m, 4H).

Example 1006: (2S)-1-(4-((3-(2-(8-azabicyclo[3.2.1]octan-3-yl)benzo[d]oxazol-5-yl)-2-methylbenzyl)oxy)-5-chloro-2-((5-cyanopyridin-3-yl)methoxy)benzyl)piperidine-2-carboxylic Acid

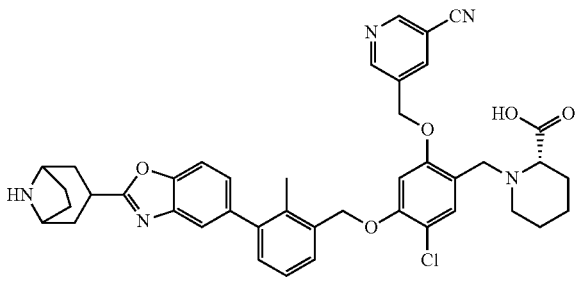 [SMILES: Cc1c(COc2cc(OCc3cncc(C#N)c3)c(CN3CCCC[C@H]3C(=O)O)cc2Cl)cccc1-c1ccc2oc(C3CC4CCC(C3)N4)nc2c1]

The crude material was purified via preparative HPLC using the following conditions: Waters XBridge 5 μm C18, 30×100 mm where mobile phase A was 5:95 acetonitrile:water with 10 mM ammonium acetate and mobile phase B was 95:5 acetonitrile:water with 10 mM ammonium acetate at a gradient of 30-100% B over 25 minutes with a 10-minute hold at a flow rate of 30 mL/minute. Fractions containing the desired product were evaporated. The yield of the product was 24 mg (21% yield), and its estimated purity by LCMS analysis was 99%.

Two analytical LC/MS injections were used to determine the final purity.

Injection 1 conditions: Waters Xbridge 3.5 μm C18, 3.0×150 mm where mobile phase A was 5:95 acetonitrile:water with 10 mM ammonium acetate; mobile phase B was 95:5 acetonitrile:water with 10 mM ammonium acetate at a temperature of 50° C. at a gradient of 10-100% B over 15 minutes with a 5-minute hold at 100% B at a flow rate of 0.5 mL/minute at a UV wavelength of 220 nm.

Injection 2 conditions: Waters Sunfire 3.5 μm C18, 3.0×150 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 10-100% B over 15 minutes with a 5-minute hold at 100% B at a flow rate of 0.5 mL/minute at a UV wavelength of 220 nm.

Analysis condition 1: Retention time=14.11 min; 98% purity.

Analysis condition 2: Retention time=6.01 min; 98% purity.

The LC/MS data was obtained on a Shimadzu analytical LCMS (ESI+) at 220 nm using the following set of conditions: Waters Aquity BEH 1.7 μm C18, 2.1×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.165 min., m/z 732.20 & 734.20 (M+H).

$^1$H NMR (500 MHz, CD$_3$OD) δ 8.96 (d, J=2.0 Hz, 1H), 8.93 (d, J=2.0 Hz, 1H), 8.42-8.37 (m, 1H), 7.67 (m, 2H), 7.57 (d, J=1.3 Hz, 1H), 7.49 (dd, J=6.8, 1.9 Hz, 1H), 7.34 (dd, J=8.4, 1.7 Hz, 1H), 7.32-7.24 (m, 2H), 7.05 (s, 1H), 5.39 (s, 2H), 5.33 (s, 2H), 4.44 (d, J=13.1 Hz, 1H), 4.31 (d, J=13.1 Hz, 1H), 4.19 (m, 2H), 3.77-3.63 (m, 1H), 3.55-3.44 (m, 1H), 2.91 (m, 1H), 2.42-2.29 (m, 6H), 2.27 (s, 3H), 2.25-2.19 (m, 3H), 1.91-1.74 (m, 3H), 1.74-1.63 (m, 1H), 1.60-1.48 (m, 1H), 1.40-1.27 (m, 1H).

Intermediate:
5-bromo-2-(pyridin-4-yl)benzo[d]oxazole

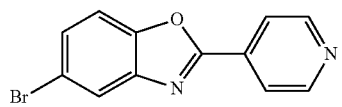 [SMILES: Brc1ccc2oc(-c3ccncc3)nc2c1]

235 mg of 5-bromo-2-(pyridin-4-yl)benzo[d]oxazole (42% yield) was obtained as a pink solid. The LC/MS data was obtained on a Shimadzu analytical LCMS (ESI+) at 220 nm using the following set of conditions: Waters Aquity BEH 1.7 μm C18, 2.1×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.137 min., m/z 275.05, 277.05 (M+H), 65% purity. $^1$H NMR (500 MHz, DMSO-d$_6$) δ 8.88 (m, 2H), 8.16 (d, J=1.9 Hz, 1H), 8.11 (m, 2H), 7.87 (d, J=8.7 Hz, 1H), 7.69 (dd, J=8.7, 1.9 Hz, 1H).

Example 1007: (S)-1-(5-chloro-2-((5-cyanopyridin-3-yl)methoxy)-4-((2-methyl-3-(2-(pyridin-4-yl)benzo[d]oxazol-5-yl)benzyl)oxy)benzyl)piperidine-2-carboxylic Acid

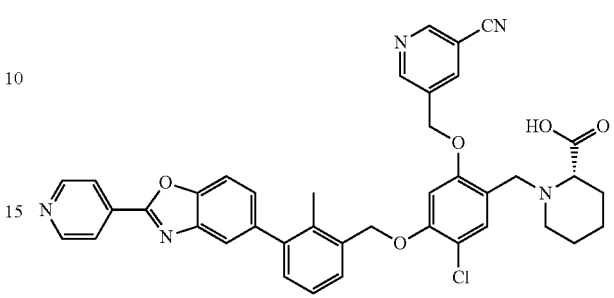

The crude material was purified via preparative HPLC using the following conditions: Waters XBridge 5 μm C18, 30×100 mm where mobile phase A was 5:95 acetonitrile:water with 10 mM ammonium acetate and mobile phase B was 95:5 acetonitrile:water with 10 mM ammonium acetate at a gradient of 10-100% B over 20 minutes with a 10-minute hold at a flow rate of 30 mL/minute. Fractions containing the desired product were evaporated. The yield of the product was 18 mg (31% yield), and its estimated purity by LCMS analysis was 95%.

Two analytical LC/MS injections were used to determine the final purity:

Injection 1 conditions: Waters Xbridge 3.5 μm C18, 3.0×150 mm where mobile phase A was 5:95 acetonitrile:water with 10 mM ammonium acetate; mobile phase B was 95:5 acetonitrile:water with 10 mM ammonium acetate at a temperature of 50° C. at a gradient of 10-100% B over 15 minutes with a 5-minute hold at 100% B at a flow rate of 0.5 mL/minute at a UV wavelength of 220 nm.

Injection 2 conditions: Waters Sunfire 3.5 μm C18, 3.0×150 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 10-100% B over 15 minutes with a 5-minute hold at 100% B at a flow rate of 0.5 mL/minute at a UV wavelength of 220 nm.

Analysis condition 1: Retention time=14.27 min; 95% purity.

Analysis condition 2: Retention time=8.18 min; 95% purity.

The LC/MS data was obtained on a Shimadzu analytical LCMS (ESI+) at 220 nm using the following set of conditions: Waters Aquity BEH 1.7 μm C18, 2.1×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.400 min., m/z 700.20 (M+H).

$^1$H NMR (500 MHz, CD$_3$OD) δ8.94 (d, J=1.9 Hz, 1H), 8.91 (d, J=1.9 Hz, 1H), 8.80 (m, 2H), 8.38 (t, J=2.0 Hz, 1H), 8.22 (m, 2H), 7.88-7.76 (m, 1H), 7.73-7.66 (m, 1H), 7.65 (s, 1H), 7.48 (m, 1H), 7.46-7.37 (m, 1H), 7.29 (m, 2H), 7.04 (s, 1H), 5.37 (s, 2H), 5.32 (s, 2H), 4.44 (d, J=13.1 Hz, 1H), 4.30 (d, J=13.1 Hz, 1H), 3.50 (d, J=7.7 Hz, 1H), 3.33 (m, 1H), 2.98-2.87 (m, 1H), 2.29 (s, 3H), 2.25-2.16 (m, 1H), 1.90-1.73 (m, 3H), 1.68 (m, 1H), 1.52 (m, 1H).

Intermediate: 5-bromo-2-(1-methylpyrrolidin-3-yl)benzo[d]oxazole

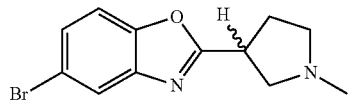 [SMILES: CN1CCC(c2nc3cc(Br)ccc3o2)C1]

171 mg of 5-bromo-2-(1-methylpyrrolidin-3-yl)benzo[d]oxazole (40% yield) was obtained as a red oily solid. The LC/MS data was obtained on a Shimadzu analytical LCMS (ESI+) at 220 nm using the following set of conditions: Waters Aquity BEH 1.7 μm C18, 2.1×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.092 min., m/z 281.15 and 283.15 (M+H), 70% purity. $^1$H NMR (500 MHz, DMSO-d$_6$) δ 7.93 (d, J=2.0 Hz, 1H), 7.69-7.65 (d, J=8.6 Hz, 1H), 7.52 (dd, J=8.6, 2.0 Hz, 1H), 3.71 (m, 1H), 2.89 (m, 1H), 2.81 (m, 1H), 2.58 (m, 2H), 2.32-2.17 (m, 5H).

Example 1008: (2S)-1-(5-chloro-2-((5-cyanopyridin-3-yl)methoxy)-4-((2-methyl-3-(2-(1-methylpyrrolidin-3-yl)benzo[d]oxazol-5-yl)benzyl)oxy)benzyl)piperidine-2-carboxylic Acid

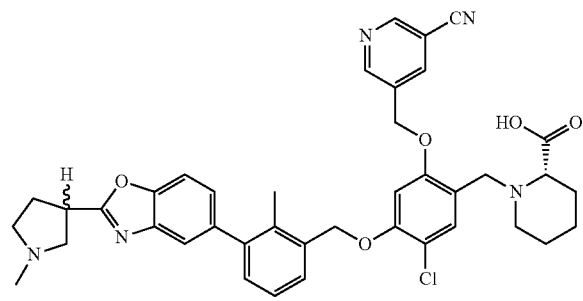 [SMILES: Cc1c(COc2cc(OCc3cncc(C#N)c3)c(CN3CCCC[C@H]3C(=O)O)cc2Cl)cccc1-c1ccc2oc(C3CCN(C)C3)nc2c1]

The crude material was purified via preparative LC/MS using the following conditions: Waters XBridge 5 μm C18, 19×200 mm where mobile phase A was 5:95 acetonitrile:water with 10 mM ammonium acetate and mobile phase B was 95:5 acetonitrile:water with 10 mM ammonium acetate at a gradient of 20-60% B over 25 minutes with a 5-minute hold at a flow rate of 20 mL/minute. The material was further purified via preparative LC/MS using the following conditions: Waters XBridge 5 μm C18, 19×200 mm where mobile phase A was 5:95 acetonitrile:water with 10 mM ammonium acetate and mobile phase B was 95:5 acetonitrile:water with 10 mM ammonium acetate at a gradient of 25-65% B over 15 minutes with a 5-minute hold at a flow rate of 20 mL/minute. Fractions containing the desired product were combined and dried via centrifugal evaporation. The yield of the product was 21.6 mg (35% yield), and its estimated purity by LCMS analysis was 91%.

Two analytical LC/MS injections were used to determine the final purity.

Injection 1 conditions: Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Injection 2 conditions: Waters Acquity UPLC BEH 1.7 μm C18, 2.1×50 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 3 minutes with a 0.75-minute hold at 100% B at a flow rate of 1.0 mL/minute at a UV wavelength of 220 nm.

Analysis condition 1: Retention time=1.319 min; ESI-MS (+) m/z=706.1 (M+H)

Analysis condition 2: Retention time=1.372 min; ESI-MS (+) m/z=706.1 (M+H)

$^1$H NMR (500 MHz, DMSO-d$_6$) δ 8.89 (m, 2H), 8.35 (s, 1H), 7.70 (d, J=8.5 Hz, 1H), 7.53 (s, 2H), 7.39 (d, J=6.7 Hz, 1H), 7.32-7.17 (m, 3H), 6.99 (s, 1H), 5.34 (s, 2H), 5.24 (s, 2H), 3.98 (m, 1H), 3.89 (m, 1H), 3.77 (m, 1H), 3.51 (m, 1H), 2.98 (m, 1H), 2.84 (m, 1H), 2.75 (m, 1H), 2.47 (m, 2H), 2.41 (s, 3H), 2.28 (m, 1H), 2.23 (m, 2H), 2.17 (s, 3H), 2.01 (m, 2H), 1.60 (m, 3H), 1.38 (m, 1H).

Intermediate: 5-bromo-7-methyl-2-(1-methylpiperidin-4-yl)benzo[d]oxazole

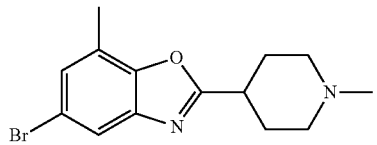 [SMILES: Cc1cc(Br)cc2nc(C3CCN(C)CC3)oc12]

196 mgs of 5-bromo-7-methyl-2-(1-methylpiperidin-4-yl)benzo[d]oxazole (43% yield) was obtained as an orange solid. The LC/MS data was obtained on a Shimadzu analytical LCMS (ESI+) at 220 nm using the following set of conditions: Waters Aquity BEH 1.7 μm C18, 2.1×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.167 min., m/z 309.15, 311.11 (M+H), 85% purity. $^1$H NMR (500 MHz, CD$_3$OD) δ 7.59 (d, J=1.4 Hz, 1H), 7.32 (d, J=1.4 Hz, 1H), 3.10-2.94 (m, 3H), 2.48 (s, 3H), 2.35 (s, 3H), 2.29 (t, J=11.1 Hz, 2H), 2.24-2.15 (m, 2H), 2.06-1.93 (m, 2H).

Example 1009: (S)-1-(5-chloro-2-((5-cyanopyridin-3-yl)methoxy)-4-((2-methyl-3-(7-methyl-2-(1-methylpiperidin-4-yl)benzo[d]oxazol-5-yl)benzyl)oxy)benzyl)piperidine-2-carboxylic Acid

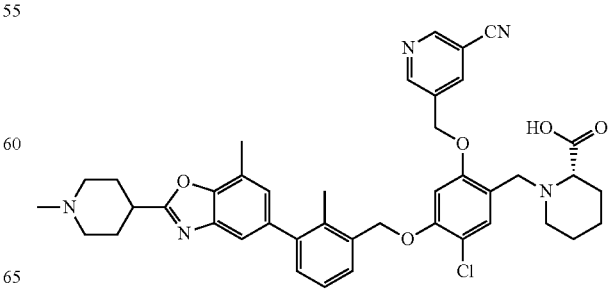

The crude material was purified using a Shimadzu preparative HPLC employing acetonitrile/water/ammonium acetate where solvent A was 5% acetonitrile/95% water/10 mM ammonium acetate and solvent B was 5% water/95% acetonitrile/10 mM ammonium acetate with a Waters XBridge 5 μm C18 30×100 mm column at a gradient of 10-100% B and a flow rate of 30 mL/min. over 20 minutes with a 10 minute hold. Fractions containing the desired product were combined and dried via centrifugal evaporation. The yield of the product was 38 mg (62% yield), and its estimated purity by LCMS analysis was 94%.

Two analytical LC/MS injections were used to determine the final purity.

Injection 1 conditions: Waters Xbridge 3.5 μm C18, 3.0×150 mm where mobile phase A was 5:95 acetonitrile:water with 10 mM ammonium acetate; mobile phase B was 95:5 acetonitrile:water with 10 mM ammonium acetate at a temperature of 50° C. at a gradient of 10-100% B over 15 minutes with a 5-minute hold at 100% B at a flow rate of 0.5 mL/minute at a UV wavelength of 220 nm.

Injection 2 conditions: Waters Sunfire 3.5 μm C18, 3.0×150 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 10-100% B over 15 minutes with a 5-minute hold at 100% B at a flow rate of 0.5 mL/minute at a UV wavelength of 220 nm.

Analysis condition 1: Retention time=14.57 min; 94% purity.

Analysis condition 2: Retention time=7.64 min; 94% purity.

The LC/MS data was obtained on a Shimadzu analytical LCMS (ESI+) at 220 nm using the following set of conditions: Waters Aquity BEH 1.7 μm C18, 2.1×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.244 min., m/z 734.25 & 735.25 (M+H).

¹H NMR (500 MHz, CD₃OD) δ 8.94 (d, J=1.9 Hz, 1H), 8.92 (d, J=1.9 Hz, 1H), 8.37 (t, J=1.9 Hz, 1H), 7.64 (s, 1H), 7.47 (dd, J=6.9, 2.1 Hz, 1H), 7.35 (d, J=0.8 Hz, 1H), 7.31-7.22 (m, 2H), 7.11 (s, 1H), 7.04 (s, 1H), 5.37 (s, 2H), 5.30 (s, 2H), 4.42 (m, 1H), 4.28 (m, 1H), 3.50 (m, 1H), 3.31 (m, 4H), 2.97-2.78 (s, 3H), 2.65 (m, 3H), 2.56 (s, 3H), 2.46-2.34 (m, 2H), 2.31-2.16 (m, 5H), 1.92-1.75 (m, 4H), 1.70 (m, 1H), 1.52 (m, 1H).

Intermediate: 5-bromo-4-methyl-2-(1-methylpiperidin-4-yl)benzo[d]oxazole

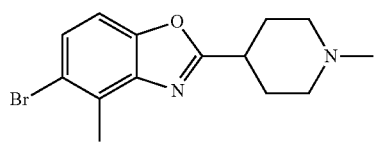 [SMILES: Cc1c(Br)ccc2oc(C3CCN(C)CC3)nc12]

197.9 mgs of 5-bromo-4-methyl-2-(1-methylpiperidin-4-yl)benzo[d]oxazole (45% yield) was obtained as a red solid. The LC/MS data was obtained on a Shimadzu analytical LCMS (ESI+) at 220 nm using the following set of conditions: Waters Aquity BEH 1.7 μm C18, 2.1×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.105 min., m/z 309.10 & 311.10 (M+H), 70% purity. ¹H NMR (500 MHz, CDCl₃) δ 7.45 (d, J=8.7 Hz, 1H), 7.20 (d, J=8.7 Hz, 1H), 2.99-2.90 (m, 3H), 2.63 (s, 3H), 2.33 (s, 3H), 2.20-1.99 (m, 6H).

Example 1010: (S)-1-(5-chloro-2-((5-cyanopyridin-3-yl)methoxy)-4-((2-methyl-3-(4-methyl-2-(1-methylpiperidin-4-yl)benzo[d]oxazol-5-yl)benzyl)oxy)benzyl)piperidine-2-carboxylic Acid

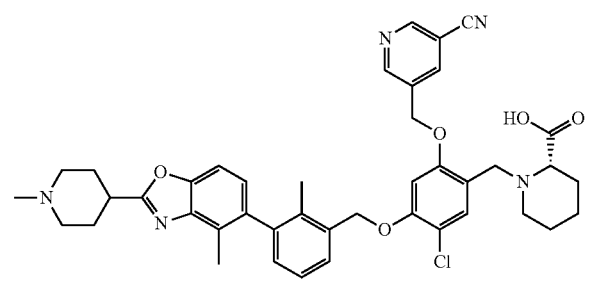 [SMILES: Cc1c(COc2cc(OCc3cncc(C#N)c3)c(CN3CCCC[C@H]3C(=O)O)cc2Cl)cccc1-c1ccc2oc(C3CCN(C)CC3)nc2c1C]

The crude material was purified using a Shimadzu preparative HPLC employing acetonitrile/water/ammonium acetate where solvent A was 5% acetonitrile/95% water/10 mM ammonium acetate and solvent B was 5% water/95% acetonitrile/10 mM ammonium acetate with a Waters XBridge 5u C18 30×100 mm column at a gradient of 10-100% B and a flow rate of 30 mL/min. over 20 minutes with a 10 minute hold. The product was repurified via preparative LC/MS using the following conditions: Waters XBridge 5 μm C18, 19×200 mm where mobile phase A was 5:95 acetonitrile:water with 10 mM ammonium acetate and mobile phase B was 95:5 acetonitrile:water with 10 mM ammonium acetate at a gradient of 15-100% B over 15 minutes with a 5-minute hold at a flow rate of 20 mL/minute. Fractions containing the desired product were combined and dried via centrifugal evaporation. The yield of the product was 17 mg (29% yield), and its estimated purity by LCMS analysis was 99%.

Two analytical LC/MS injections were used to determine the final purity.

Injection 1 conditions: Waters Xbridge 3.5 μm C18, 3.0×150 mm where mobile phase A was 5:95 acetonitrile:water with 10 mM ammonium acetate; mobile phase B was 95:5 acetonitrile:water with 10 mM ammonium acetate at a temperature of 50° C. at a gradient of 10-100% B over 15 minutes with a 5-minute hold at 100% B at a flow rate of 0.5 mL/minute at a UV wavelength of 220 nm.

Injection 2 conditions: Waters Sunfire 3.5 μm C18, 3.0×150 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 10-100% B over 15 minutes with a 5-minute hold at 100% B at a flow rate of 0.5 mL/minute at a UV wavelength of 220 nm.

Analysis condition 1: Retention time=14.45 min; 99% purity.

Analysis condition 2: Retention time=7.39 min; 99% purity.

The LC/MS data was obtained on a Shimadzu analytical LCMS (ESI+) at 220 nm using the following set of conditions: Waters Aquity BEH 1.7 μm C18, 2.1×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.149 min., m/z 734.25 (M+H), 99% purity.

$^1$H NMR (500 MHz, CD$_3$OD) δ 8.88 (m, 1H), 8.82 (m, 1H), 8.31 (m, 1H), 7.55 (s, 1H), 7.40 (m, 1H), 7.37 (m, 1H), 7.18 (m, 1H), 7.08-6.91 (m, 3H), 5.28 (s, 2H), 5.23 (s, 2H), 4.34 (m, 1H), 4.19 (m, 1H), 3.40 (m, 1H), 3.24 (m, 1H), 3.18 (m, 1H), 2.85-2.67 (m, 3H), 2.56 (m, 4H), 2.32-2.22 (m, 2H), 2.20-2.07 (m, 6H), 1.99 (s, 3H), 1.82 (m, 2H), 1.80-1.63 (m, 2H), 1.63-1.54 (m, 1H), 1.47-1.35 (m, 1H).

Intermediate: 5-bromo-2-(4-methylpiperidin-4-yl)benzo[d]oxazole

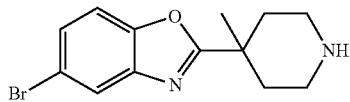

243.2 mgs of 5-bromo-2-(4-methylpiperidin-4-yl)benzo[d]oxazole (56% yield) was obtained as a tan oily solid. The LC/MS data was obtained on a Shimadzu analytical LCMS (ESI+) at 220 nm using the following set of conditions: Waters Aquity BEH 1.7 μm C18, 2.1×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.119 min., m/z 295.10 & 297.10 (M+H), 90% purity. $^1$H NMR (500 MHz, DMSO-d$_6$) δ 7.97 (d, J=1.4 Hz, 1H), 7.69 (d, J=8.5 Hz, 1H), 7.53 (dd, J=8.5, 1.4 Hz, 1H), 2.83 (m, 2H), 2.58 (m, 2H), 2.19 (m, 2H), 1.60 (m, 2H), 1.36 (s, 3H).

Example 1011: (S)-1-(5-chloro-2-((5-cyanopyridin-3-yl)methoxy)-4-((2-methyl-3-(2-(4-methylpiperidin-4-yl)benzo[d]oxazol-5-yl)benzyl)oxy)benzyl)piperidine-2-carboxylic Acid

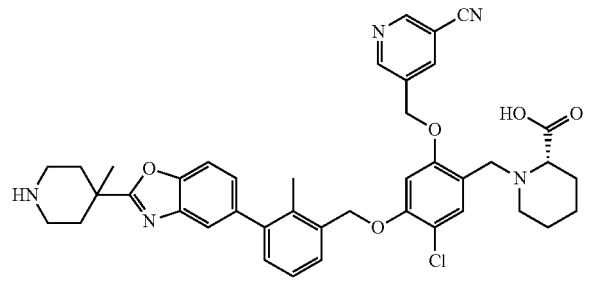 [SMILES: Cc1c(COc2cc(OCc3cncc(C#N)c3)c(CN3CCCC[C@H]3C(=O)O)cc2Cl)cccc1-c1ccc2oc(C3(C)CCNCC3)nc2c1]

The crude material was purified via preparative LC/MS using the following conditions: Waters XBridge 5 μm C18, 19×200 mm where mobile phase A was 5:95 acetonitrile:water with 10 mM ammonium acetate and mobile phase B was 95:5 acetonitrile:water with 10 mM ammonium acetate at a gradient of 15-100% B over 15 minutes with a 5-minute hold at a flow rate of 20 mL/minute. Fractions containing the desired product were combined and dried via centrifugal evaporation. The yield of the product was 6.4 mg (15% yield), and its estimated purity by LCMS analysis was 98%. Two analytical LC/MS injections were used to determine the final purity.

Injection 1 conditions: Waters Sunfire 3.5 μm C18, 3.0×150 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 20 minutes with a 5-minute hold at 100% B at a flow rate of 1.0 mL/minute at a UV wavelength of 220 nm.

Injection 2 conditions: Waters Xbridge 3.5 μm Phenyl, 3.0×150 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 20 minutes with a 5-minute hold at 100% B at a flow rate of 1.0 mL/minute at a UV wavelength of 220 nm.

Analysis condition 1: Retention time=7.40 min., 98% purity.

Analysis condition 2: Retention time=8.17 min., 98% purity.

The LC/MS data was obtained on a Shimadzu analytical LCMS (ESI+) at 220 nm using the following set of conditions: Waters Aquity BEH 1.7 μm C18, 2.1×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.152 min., m/z 720.20 & 722.25 (M+H), 98% purity.

$^1$H NMR (500 MHz, CD$_3$OD) δ 8.93 (d, J=1.9 Hz, 1H), 8.96 (d, J=2.0 Hz, 1H), 8.39 (t, J=1.9 Hz, 1H), 7.70 (d, J=8.4 Hz, 1H), 7.67 (s, 1H), 7.61 (d, J=1.1 Hz, 1H), 7.49 (dd, J=6.9, 2.1 Hz, 1H), 7.36 (dd, J=8.4, 1.7 Hz, 1H), 7.32-7.25 (m, 2H), 7.05 (s, 1H), 5.39 (s, 2H), 5.34 (s, 2H), 4.44 (d, J=13.1 Hz, 1H), 4.31 (d, J=13.1 Hz, 1H), 3.50 (dd, J=10.6, 3.5 Hz, 1H), 3.42-3.35 (m, 2H), 3.32-3.12 (m, 2H), 3.01-2.85 (m, 1H), 2.65 (m, 2H), 2.29 (s, 3H), 2.26-2.16 (m, 1H), 2.03 (m, 2H), 1.96-1.91 (m, 1H), 1.90-1.68 (m, 4H), 1.59-1.45 (m, 4H).

Intermediate: 4-(5-bromobenzo[d]oxazol-2-yl)-N,N-diethylcyclohexanamine

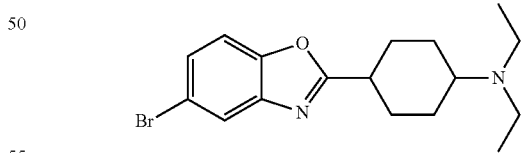

407.8 mgs of 4-(5-bromobenzo[d]oxazol-2-yl)-N,N-diethylcyclohexanamine (74% yield) was obtained as a red oily solid. The LC/MS data was obtained on a Shimadzu analytical LCMS (ESI+) at 220 nm using the following set of conditions: Waters Aquity BEH 1.7 μm C18, 2.1×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.182 min., m/z 351.15 & 353.15 (M+H), 85% purity. $^1$H NMR (500

MHz, CDCl₃) δ 7.80 (m, 1H), 7.42 (m, 1H), 7.35 (m, 1H), 3.08-2.84 (m, 6H), 2.45-2.32 (m, 2H), 2.25 (m, 2H), 1.96-1.60 (m, 4H), 1.30 (m, 6H).

Example 1012: (S)-1-(5-chloro-2-((5-cyanopyridin-3-yl)methoxy)-4-((3-(2-(4-(diethylamino)cyclohexyl)benzo[d]oxazol-5-yl)-2-methylbenzyl)oxy)benzyl)piperidine-2-carboxylic Acid

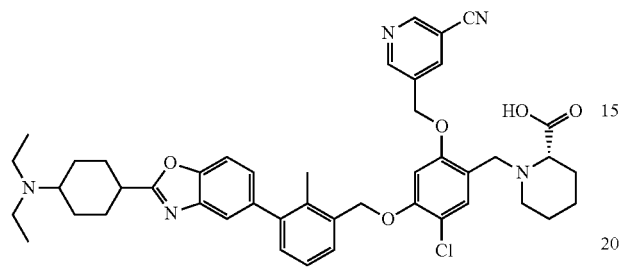

The crude material was purified using a Shimadzu preparative HPLC employing acetonitrile/water/10 mM ammonium acetate where solvent A was 5% acetonitrile/95% water/10 mM ammonium acetate and solvent B was 5% water/95% acetonitrile/10 mM ammonium acetate with a Waters XBridge 5 μm C18 OBD 30×100 mm column at a gradient of 5-100% B and a flow rate of 30 mL/min. over 20 minutes with a 10 minute hold. The product was repurified via preparative LC/MS using the following conditions: Waters XBridge 5 μm C18, 19×200 mm where mobile phase A was 5:95 acetonitrile: water with 10 mM ammonium acetate and mobile phase B was 95:5 acetonitrile:water with 10 mM ammonium acetate at a gradient of 10-50% B over 30 minutes with a 5-minute hold at a flow rate of 20 mL/minute. The yield of the product was 12.5 mg (20% yield), and its estimated purity by LCMS analysis was 98%. Two analytical LC/MS injections were used to determine the final purity.

Injection 1 conditions: Waters Sunfire 3.5 μm C18, 3.0×150 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 20 minutes with a 5-minute hold at 100% B at a flow rate of 1.0 mL/minute at a UV wavelength of 220 nm.

Injection 2 conditions: Waters Xbridge 3.5 μm Phenyl, 3.0×150 mm where mobile phase A was 5:95 acetonitrile: water with 0.1% trifluoroacetic acid; mobile phase B was 95:5 acetonitrile:water with 0.1% trifluoroacetic acid at a temperature of 50° C. at a gradient of 0-100% B over 20 minutes with a 5-minute hold at 100% B at a flow rate of 1.0 mL/minute at a UV wavelength of 220 nm.

Analysis condition 1: Retention time=8.78 min., 98% purity.

Analysis condition 2: Retention time=10.09 min., 98% purity.

The LC/MS data was obtained on a Shimadzu analytical LCMS (ESI+) at 220 nm using the following set of conditions: Waters Aquity BEH 1.7 μm C18, 2.1×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.092 min., m/z 776.30 (M+H), 100% purity.

¹H NMR (500 MHz, CD₃OD) δ 8.96 (d, J=1.9 Hz, 1H), 8.93 (d, J=1.9 Hz, 1H), 8.40 (t, J=1.9 Hz, 1H), 7.68-7.65 (m, 2H), 7.57 (m, 1H), 7.49 (dd, J=6.4, 2.4 Hz, 1H), 7.34 (dd, J=8.4, 1.6 Hz, 1H), 7.30-7.26 (m, 2H), 7.06 (s, 1H), 5.39 (s, 2H), 5.34 (s, 2H), 4.45 (d, J=12.9 Hz, 1H), 4.32 (d, J=12.9 Hz, 1H), 3.54-3.45 (m, 2H), 3.36 (m, 1H), 3.32-3.27 (m, 3H), 3.22 (m, 1H), 3.13 (m, 1H), 2.97-2.89 (m, 1H), 2.49 (m, 2H), 2.28 (m, 6H), 1.92-1.77 (m, 7H), 1.70 (m, 1H), 1.55 (m, 1H), 1.40 (t, J=7.3 Hz, 6H).

Intermediate: 5-bromo-2-(1-isopropylpiperidin-4-yl)benzo[d]oxazole

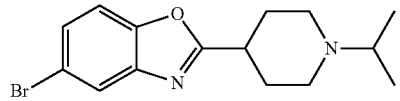 [SMILES: CC(C)N1CCC(c2nc3cc(Br)ccc3o2)CC1]

264 mgs of 5-bromo-2-(1-isopropylpiperidin-4-yl)benzo[d]oxazole (76% yield) was obtained as a pink solid. The LC/MS data was obtained on a Shimadzu analytical LCMS (ESI+) at 220 nm using the following set of conditions: Waters Aquity BEH 1.7 μm C18, 2.1×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=0.972 min., m/z 323.15 & 325.15 (M+H), 99% purity. ¹H NMR (500 MHz, CD₃OD) δ 7.82 (dd, J=1.7, 0.5 Hz, 1H), 7.53 (d, J=0.5 Hz, 1H), 7.52 (d, J=1.7 Hz, 1H), 3.12-3.00 (m, 3H), 2.82 (m, 1H), 2.45 (td, J=11.7, 2.4 Hz, 2H), 2.27-2.17 (m, 2H), 2.06-1.94 (m, 2H), 1.18-1.09 (m, 6H).

Example 1013: (S)-1-(5-chloro-2-((5-cyanopyridin-3-yl)methoxy)-4-((3-(2-(1-isopropylpiperidin-4-yl)benzo[d]oxazol-5-yl)-2-methylbenzyl)oxy)benzyl)piperidine-2-carboxylic Acid

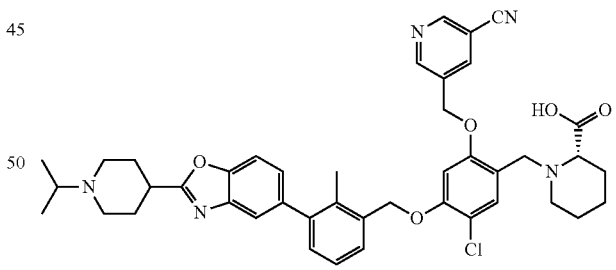

The crude material was purified via preparative HPLC using the following conditions: Waters XBridge 5 μm C18, 30×100 mm where mobile phase A was 5:95 acetonitrile:water with 10 mM ammonium acetate and mobile phase B was 95:5 acetonitrile:water with 10 mM ammonium acetate at a gradient of 0-75% B over 25 minutes with a 10-minute hold at a flow rate of 30 mL/minute. Fractions containing the desired product were evaporated. The yield of the product was 15.2 mg (25% yield), and its estimated purity by LCMS analysis was 97%.

Two analytical LC/MS injections were used to determine the final purity.

Injection 1 conditions: Waters Xbridge 3.5 μm C18, 3.0×150 mm where mobile phase A was 5:95 acetonitrile:water with 10 mM ammonium acetate; mobile phase B was 95:5 acetonitrile:water with 10 mM ammonium acetate at a temperature of 50° C. at a gradient of 10-100% B over 15 minutes with a 5-minute hold at 100% B at a flow rate of 0.5 mL/minute at a UV wavelength of 220 nm.

Injection 2 conditions: Waters Sunfire 3.5 μm C18, 3.0×150 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 10-100% B over 15 minutes with a 5-minute hold at 100% B at a flow rate of 0.5 mL/minute at a UV wavelength of 220 nm.

Analysis condition 1: Retention time=14.77 min; 97% purity.

Analysis condition 2: Retention time=6.35 min; 99% purity.

The LC/MS data was obtained on a Shimadzu analytical LCMS (ESI+) at 220 nm using the following set of conditions: Waters Aquity BEH 1.7 μm C18, 2.1×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=0.890 min., m/z 749.10 (M+H).

$^1$H NMR (500 MHz, C D$_3$OD) δ 8.96 (d, J=1.9 Hz, 1H), 8.92 (d, J=1.9 Hz, 1H), 8.39 (s, 1H), 7.66 (m, 2H), 7.54 (d, J=1.3 Hz, 1H), 7.48 (dd, J=6.9, 1.9 Hz, 1H), 7.33 (dd, J=8.4, 1.6 Hz, 1H), 7.27 (m, 2H), 7.04 (s, 1H), 5.38 (s, 2H), 5.31 (s, 2H), 4.46 (d, J=13.1 Hz, 1H), 4.31 (d, J=13.1 Hz, 1H), 3.56-3.35 (m, 6H), 3.14 (t, J=11.3 Hz, 2H), 2.92 (td, J=12.0, 3.2 Hz, 1H), 2.48 (dd, J=14.2, 3.0 Hz, 2H), 2.35-2.18 (m, 6H), 1.92-1.75 (m, 3H), 1.70 (m, 1H), 1.59-1.48 (m, 1H), 1.44-1.28 (m, 6H).

Intermediate: 5-bromo-2-(8-methyl-8-azabicyclo[3.2.1]octan-3-yl)benzo[d]oxazole

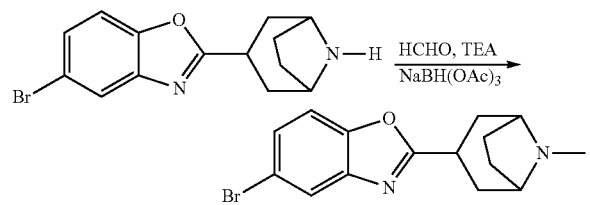

To a solution of 2-(8-azabicyclo[3.2.1]octan-3-yl)-5-bromobenzo[d]oxazole (78.2 mg, 0.255 mmol) in DCE (1,2-dichloroethane, 3 mL) with triethylamine (0.106 mL, 0.764 mmol) was added 2.5 eq. of 37% aq. formaldehyde (0.047 mL, 0.636 mmol). The mixture was stirred for 1 hour at room temperature. To the reaction mixture was then added neat sodium triacetoxyborohydride (216 mg, 1.018 mmol) and the mixture stirred overnight at room temperature. The reaction mixture was further diluted with 10 mL of DCM (dichloromethane), washed with 2 mL of 1.5M aq. potassium phosphate, brine, dried over sodium sulfate, filtered, and evaporated under nitrogen to give 96 mgs of a red oil. The crude product was taken up in 10 mL of methanol and pushed through a Biotage 5 g SCX-2 ion exchange cartridge. The cartridge flushed with 3 column volumes (30 mL) of methanol, the basic product eluted with 30 mL of 2M ammonia in methanol. 49.6 mgs of 5-bromo-2-(8-methyl-8-azabicyclo[3.2.1]octan-3-yl)benzo[d]oxazole (60% yield) was obtained as a reddish-tan solid. The LC/MS data was obtained on a Shimadzu analytical LCMS (ESI+) at 220 nm using the following set of conditions: Waters Aquity BEH 1.7 μm C18, 2.1×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=0.925 min., m/z 321.15 & 323.15 (M+H), 99% purity. $^1$H NMR (500 MHz, CDCl$_3$) δ 7.79 (d, J=1.9 Hz, 1H), 7.40 (dd, 1.9 Hz, 1H), 7.33 (d, J=8.5 Hz, 1H), 3.34-3.24 (m, 3H), 2.36 (s, 3H), 2.22-2.10 (m, 4H), 1.93-1.84 (m, 2H), 1.74-1.66 (m, 2H).

Example 1014: (2S)-1-(5-chloro-2-((5-cyanopyridin-3-yl)methoxy)-4-((2-methyl-3-(2-(8-methyl-8-azabicyclo[3.2.1]octan-3-yl)benzo[d]oxazol-5-yl)benzyl)oxy)benzyl)piperidine-2-carboxylic Acid

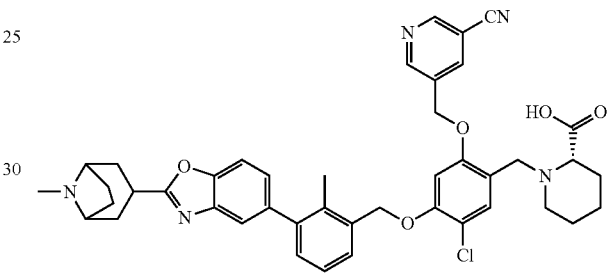

The crude material was purified using a Shimadzu preparative HPLC employing acetonitrile/water/ammonium acetate where solvent A was 5% acetonitrile/95% water/10 mM ammonium acetate and solvent B was 5% water/95% acetonitrile/10 mM ammonium acetate with a Xbridge 5 μm 30×100 mm C18 column at a gradient of 30-100% B and a flow rate of 30 mL/min. over 25 minutes with a 10 minute hold. The fractions containing the desired product were evaporated. The yield of the product was 46.5 mg (38% yield), and its estimated purity by LCMS analysis was 98%. Two analytical LC/MS injections were used to determine the final purity.

Injection 1 conditions: Waters Xbridge 3.5 μm C18, 3.0×150 mm where mobile phase A was 5:95 acetonitrile:water with 10 mM ammonium acetate; mobile phase B was 95:5 acetonitrile:water with 10 mM ammonium acetate at a temperature of 50° C. at a gradient of 10-100% B over 15 minutes with a 5-minute hold at 100% B at a flow rate of 0.5 mL/minute at a UV wavelength of 220 nm.

Injection 2 conditions: Waters Sunfire 3.5 μm C18, 3.0×150 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 10-100% B over 15 minutes with a 5-minute hold at 100% B at a flow rate of 0.5 mL/minute at a UV wavelength of 220 nm.

Analysis condition 1: Retention time=14.12 min; 99% purity.

Analysis condition 2: Retention time=6.15 min; 98% purity.

The LC/MS data was obtained on a Shimadzu analytical LCMS (ESI+) at 220 nm using the following set of conditions: Waters Aquity BEH 1.7 µm C18, 2.1×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.159 min., m/z 746.20 & 748.15 (M+H).

¹H NMR (400 MHz, CD₃OD) δ 8.96 (s, 1H), 8.93 (s, 1H), 8.38 (s, 1H), 7.71-7.62 (m, 2H), 7.54 (s, 1H), 7.49 (d, J=8.8 Hz, 1H), 7.33 (dd, J=8.3, 1.7 Hz, 1H), 7.31-7.24 (m, 2H), 7.04 (s, 1H), 5.38 (s, 2H), 5.32 (s, 2H), 4.45 (d, J=13.2 Hz, 1H), 4.31 (d, J=13.2 Hz, 1H), 3.96 (br. s., 2H), 3.73-3.62 (m, 1H), 3.55-3.46 (m, 1H), 2.99-2.87 (m, 1H), 2.79 (s, 3H), 2.49-2.34 (m, 6H), 2.27 (s, 3H), 2.19 (d, J=8.6 Hz, 3H), 1.80 (m, 3H), 1.73-1.64 (m, 1H), 1.61-1.46 (m, 1H), 1.31 (m, 1H).

Intermediate: 3-(5-bromobenzo[d]oxazol-2-yl)bicyclo[1.1.1]pentan-1-amine

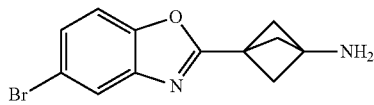 [SMILES: NC12CC(c3nc4cc(Br)ccc4o3)(C1)C2]

54 mgs of 3-(5-bromobenzo[d]oxazol-2-yl)bicyclo[1.1.1]pentan-1-amine (43% yield) was obtained as a tan solid. The LC/MS data was obtained on a Shimadzu analytical LCMS (ESI+) at 220 nm using the following set of conditions: Waters Aquity BEH 1.7 µm C18, 2.1×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=0.794 min., m/z 278.85 & 280.90 (M+H), 90% purity. ¹H NMR (500 MHz, CDCl₃) δ 7.79 (d, J=1.9 Hz, 1H), 7.41 (dd, J=8.7, 1.9 Hz, 1H), 7.34 (d, J=8.7 Hz, 1H), 2.35 (s, 6H).

Example 1015: (S)-1-(4-((3-(2-(3-aminobicyclo[1.1.1]pentan-1-yl)benzo[d]oxazol-5-yl)-2-methylbenzyl)oxy)-5-chloro-2-((5-cyanopyridin-3-yl)methoxy)benzyl)piperidine-2-carboxylic Acid

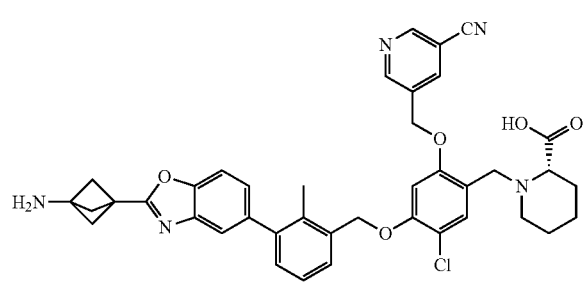 [SMILES: Cc1c(COc2cc(OCc3cncc(C#N)c3)c(CN3CCCC[C@H]3C(=O)O)cc2Cl)cccc1-c1ccc2oc(C34CC(N)(C3)C4)nc2c1]

The crude material was purified using a Shimadzu preparative HPLC employing acetonitrile/water/ammonium acetate where solvent A was 5% acetonitrile/95% water/10 mM ammonium acetate and solvent B was 5% water/95% acetonitrile/10 mM ammonium acetate with a XTERRA 5 µm C18 30×100 mm column at a gradient of 30-100% B and a flow rate of 30 mL/min. over 25 minutes with a 10 minute hold. The product was repurified using a Shimadzu preparative HPLC employing acetonitrile/water/ammonium acetate where solvent A was 5% acetonitrile/95% water/10 mM ammonium acetate and solvent B was 5% water/95% acetonitrile/10 mM ammonium acetate with a XTERRA 5 µm C18 30×100 mm column at a gradient of 30-50% B and a flow rate of 30 mL/min. over 25 minutes with a 5 minute hold then 50-100% B over 10 minutes. The fractions containing the desired product were combined and evaporated. The yield of the product was 6 mg (11% yield), and its estimated purity by LCMS analysis was 100%.

Two analytical LC/MS injections were used to determine the final purity.

Injection 1 conditions: Waters Xbridge 3.5 µm C18, 3.0×150 mm where mobile phase A was 5:95 acetonitrile:water with 10 mM ammonium acetate; mobile phase B was 95:5 acetonitrile:water with 10 mM ammonium acetate at a temperature of 50° C. at a gradient of 10-100% B over 15 minutes with a 5-minute hold at 100% B at a flow rate of 0.5 mL/minute at a UV wavelength of 220 nm.

Injection 2 conditions: Waters Sunfire 3.5 µm C18, 3.0×150 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 10-100% B over 15 minutes with a 5-minute hold at 100% B at a flow rate of 0.5 mL/minute at a UV wavelength of 220 nm.

Analysis condition 1: Retention time=13.15 min; 100% purity.

Analysis condition 2: Retention time=5.76 min; 100% purity.

The LC/MS data was obtained on a Shimadzu analytical LCMS (ESI+) at 220 nm using the following set of conditions: Waters Aquity BEH 1.7 µm C18, 2.1×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.090 min., m/z 704.20 & 706.15 (M+H).

¹H NMR (500 MHz, CDCl₃) δ 8.86 (d, J=1.4 Hz, 2H), 8.21 (br.s., 1H), 7.60 (d, J=1.1 Hz, 1H), 7.52 (m, 2H), 7.41 (m, 1H), 7.29-7.22 (m, 3H), 6.64 (s, 1H), 5.29-5.23 (m, 1H), 5.22-5.15 (m, 1H), 5.13 (s, 2H), 4.33 (br. s., 2H), 3.54-3.41 (m, 2H), 2.68 (m, 1H), 2.39 (s, 6H), 2.22 (s, 3H), 1.95-1.71 (m, 5H), 1.49-1.32 (m, 1H).

Intermediate: 2-(4-(5-bromobenzo[d]oxazol-2-yl)piperidin-1-yl)acetic Acid

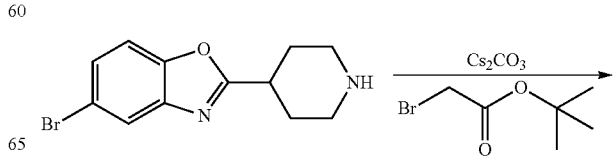

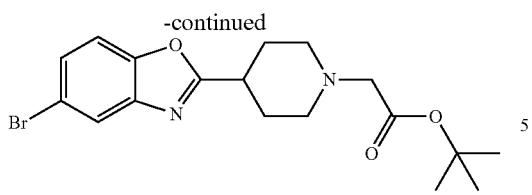

↓ TFA

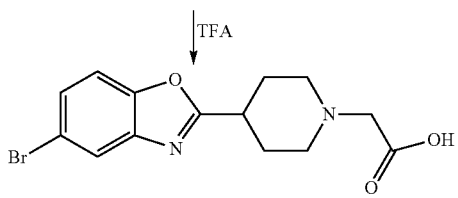

To a mixture of 5-bromo-2-(piperidin-4-yl)benzo[d]oxazole (245 mg, 0.871 mmol) and cesium carbonate (315 mg, 0.967 mmol) in DMF (3 mL) at 0° C., under nitrogen, was added, dropwise, tert-butyl 2-bromoacetate (0.135 mL, 0.915 mmol). The ice bath was removed and the mixture allowed to warm to room temperature. After 2.5 hours the reaction mixture was diluted with 2 mL of water and 20 mL of ethyl acetate. The organics were extracted, washed with brine, dried over $Na_2SO_4$, filtered and evaporated to give a crude oil. The crude product was diluted with 3 mL of water and pushed through a Waters 1 g HLB extraction cartridge. The cartridge was flushed with an additional 10 mL of water, the product eluted with 30 mL of methanol. The solvent was removed to give 304 mgs of tert-butyl 2-(4-(5-bromobenzo[d]oxazol-2-yl)piperidin-1-yl)acetate as an orange solid (88% yield). The LC/MS data was obtained on a Shimadzu analytical LCMS (ESI+) at 220 nm using the following set of conditions: Waters Aquity BEH 1.7 μm C18, 2.1×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.224 min., m/z 395.15, 397.10 (M+H), >90% purity. $^1$H NMR (500 MHz, DMSO-$d_6$) δ 7.96 (d, J=1.9 Hz, 1H), 7.69 (d, J=8.7 Hz, 1H), 7.53 (dd, J=8.7, 1.9 Hz, 1H), 3.14 (s, 2H), 3.05-2.97 (m, 1H), 2.89 (m, 2H), 2.38 (m, 2H), 2.12-2.00 (m, 2H), 1.83 (m, 2H), 1.42 (s, 9H).

To the tert-butyl 2-(4-(5-bromobenzo[d]oxazol-2-yl)piperidin-1-yl)acetate (50 mg, 0.126 mmol) in DCE (2.5 mL), at room temperature, was added, under nitrogen, trifluoroacetic acid (0.078 mL, 1.012 mmol). The purple mixture was stirred for 16 hours. The volatiles were removed under vacuum (rotovap), 10 mL of DCM was added and the evaporation process repeated to give 57.9 mgs (100% yield) of 2-(4-(5-bromobenzo[d]oxazol-2-yl)piperidin-1-yl)acetic acid, TFA as a red solid. The LC/MS data was obtained on a Shimadzu analytical LCMS (ESI+) at 220 nm using the following set of conditions: Waters Aquity BEH 1.7 μm C18, 2.1×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.024 min., m/z 339.0 & 341.05 (M+H), 99% purity. $^1$H NMR (500 MHz, CDCl$_3$) δ 9.32 (br. s., 1H), 7.88 (s, 1H), 7.53 (d, J=8.5 Hz, 1H), 7.49-7.38 (m, 1H), 3.97 (m, 2H), 3.74 (m, 1H), 3.42 (m, 2H), 3.22 (m, 2H), 2.48 (m, 2H), 1.50 (m, 2H).

Example 1016: (S)-1-(4-((3-(2-(1-(carboxymethyl) piperidin-4-yl)benzo[d]oxazol-5-yl)-2-methylbenzyl) oxy)-5-chloro-2-((5-cyanopyridin-3-yl)methoxy) benzyl)piperidine-2-carboxylic Acid

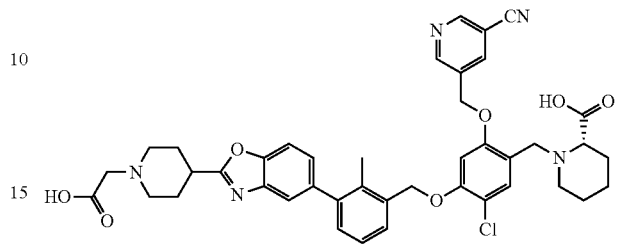

The crude material was purified via preparative LC/MS using the following conditions: Waters XBridge 5 μm C18, 19×200 mm where mobile phase A was 5:95 acetonitrile:water with 10 mM ammonium acetate and mobile phase B was 95:5 acetonitrile:water with 10 mM ammonium acetate at a gradient of 10-50% B over 25 minutes with a 5-minute hold at a flow rate of 20 mL/minute. Fractions containing the desired product were combined and dried via centrifugal evaporation. The yield of the product was 19.1 mg (26% yield), and its estimated purity by LCMS analysis was 94%. One analytical LC/MS injection was used to determine the final purity.

Injection condition: Waters Acquity UPLC BEH 1.7 μm C18, 2.1×50 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 3 minutes with a 0.75-minute hold at 100% B at a flow rate of 1.0 mL/minute at a UV wavelength of 220 nm.

Analysis condition: Retention time=1.268 min; ESI-MS (+) m/z=764.1 (M+H).

$^1$H NMR (500 MHz, DMSO-$d_6$) δ 8.98 (s, 2H), 8.41 (s, 1H), 7.72 (d, J=8.4 Hz, 1H), 7.60 (s, 1H), 7.51 (d, J=7.0 Hz, 1H), 7.41 (s, 1H), 7.33-7.22 (m, 3H), 7.10 (s, 1H), 5.33 (d, J=2.6 Hz, 2H), 5.27 (s, 2H), 3.74 (d, J=13.9 Hz, 1H), 3.57 (d, J=13.9 Hz, 1H), 3.18 (s, 2H), 3.15-3.00 (m, 4H), 2.89 (m, 1H), 2.57 (m, 2H), 2.25 (m, 4H), 2.15 (m, 2H), 1.95 (m, 2H), 1.77 (m, 2H), 1.49 (m, 3H), 1.44-1.33 (m, 1H).

Intermediate: 5-bromo-2-(tetrahydro-2H-pyran-4-yl) benzo[d]oxazole

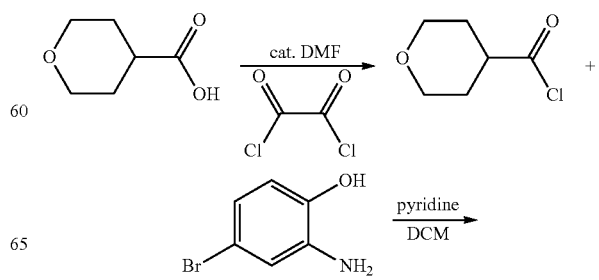

-continued

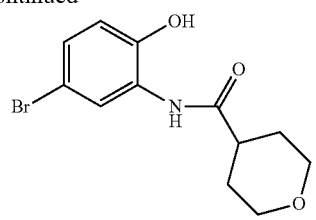

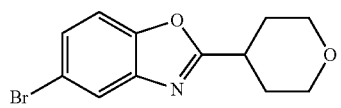

To tetrahydro-2H-pyran-4-carboxylic acid (0.690 g, 5.3 mmol) in DCM (10 mL) was added, under nitrogen, at 0° C., DMF (0.041 mL, 0.530 mmol), and dropwise, oxalyl chloride (1.180 mL, 7.9 mmol). The ice bath was removed and the mixture was stirred for 45 minutes. The volatiles were removed on the rotovap, the crude oil diluted with 10 mL of DCM and the evaporation repeated.

To a RBF (round-bottomed flask) was added 2-amino-4-bromophenol (1097 mg, 5.83 mmol) in DCM (20 mL) along with pyridine (0.429 mL, 5.30 mmol). The mixture was stirred for 15 minutes under nitrogen. In a second RBF containing the above mentioned freshly synthesized tetrahydro-2H-pyran-4-carbonyl chloride (788 mg, 5.30 mmol) was added, at room temperature, 2 mL of DCM followed by the above mixture containing 2-amino-4-bromophenol/pyridine in DCM. The combined pink heterogeneous mixture was stirred overnight at room temperature under nitrogen. The crude product mixture was washed with water, brine, dried over sodium sulfate, filtered and evaporated. The isolated crude product was triturated with 4:1 ice cold diethyl ether/hexane to give 1.512 g of N-(5-bromo-2-hydroxyphenyl)tetrahydro-2H-pyran-4-carboxamide (88% yield) as a pink solid. The LC/MS data was obtained on a Shimadzu analytical LCMS (ESI+) at 220 nm using the following set of conditions: Waters Aquity BEH 1.7 μm C18, 2.1×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.190 min., m/z 300.15, 302.15 (M+H), 90% purity.

$^1$H NMR (500 MHz, CDCl$_3$) δ 8.37 (br. s., 1H), 7.58 (br. s., 1H), 7.39 (d, J=2.4 Hz, 1H), 7.20 (dd, J=8.7, 2.4 Hz, 1H), 6.87 (d, J=8.7 Hz, 1H), 4.09 (m, 2H), 3.47 (m, 2H), 2.62 (m, 1H), 1.98-1.77 (m, 4H).

To a sealed tube was added 2 mL of dioxane, N-(5-bromo-2-hydroxyphenyl)tetrahydro-2H-pyran-4-carboxamide (200 mg, 0.666 mmol), and 3 eq of phosphorus oxychloride (0.186 mL, 1.999 mmol). The tube was sealed and the mixture heated at 110° C. for 2 hours. The mixture was cooled and the dioxane was evaporated to give a crude oil. The crude product was triturated with water and dried under vaccuum to give 160 mgs (51% yield) of 5-bromo-2-(tetrahydro-2H-pyran-4-yl)benzo[d]oxazole as a pink solid. The LC/MS data was obtained on a Shimadzu analytical LCMS (ESI+) at 220 nm using the following set of conditions: Waters Aquity BEH 1.7 μm C18, 2.1×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.427 min., m/z 282.15, 284.10 (M+H), 65% purity.

$^1$H NMR (500 MHz, CDCl$_3$) δ 7.83 (d, J=1.7 Hz, 1H), 7.44 (dd, J=1.7, 8.7 Hz, 1H), 7.37 (d, J=8.7 Hz, 1H), 4.08 (dt, J=11.7, 3.5 Hz, 2H), 3.58 (td, J=11.7, 3.5 Hz, 3H), 3.29-3.15 (m, 1H), 2.11-1.98 (m, 4H).

Example 1017: (S)-1-(5-chloro-2-((5-cyanopyridin-3-yl)methoxy)-4-((2-methyl-3-(2-(tetrahydro-2H-pyran-4-yl)benzo[d]oxazol-5-yl)benzyl)oxy)benzyl)piperidine-2-carboxylic Acid

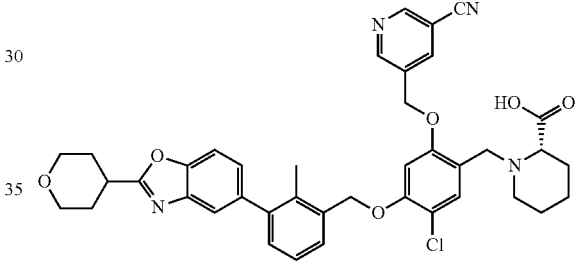

The crude material was purified using a Shimadzu preparative HPLC employing acetonitrile/water/10 mM ammonium acetate where solvent A was 5% acetonitrile/95% water/10 mM ammonium acetate and solvent B was 5% water/95% acetonitrile/10 mM ammonium acetate with a Waters XBridge 5 μm C18 OBD 30×100 mm column at a gradient of 10-100% B and a flow rate of 30 mL/min. over 20 minutes with a 10 minute hold. The fractions containing the desired material were evaporated. The yield of the product was 22 mg (39% yield), and its estimated purity by LCMS analysis was 99%. Two analytical LC/MS injections were used to determine the final purity.

Injection 1 conditions: Waters Sunfire 3.5 μm C18, 3.0×150 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 20 minutes with a 5-minute hold at 100% B at a flow rate of 1.0 mL/minute at a UV wavelength of 220 nm.

Injection 2 conditions: Waters Xbridge 3.5 μm Phenyl, 3.0×150 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 20 minutes with a 5-minute hold at 100% B at a flow rate of 1.0 mL/minute at a UV wavelength of 220 nm.

Analysis condition 1: Retention time=7.15 min., 99% purity.

Analysis condition 2: Retention time=7.66 min., 99% purity.

The LC/MS data was obtained on a Shimadzu analytical LCMS (ESI+) at 220 nm using the following set of conditions: Waters Aquity BEH 1.7 µm C18, 2.1×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.360 min., m/z 707.20 (M+H), 100% purity.

$^1$H NMR (500 MHz, CD$_3$OD) δ 8.96 (d, J=2.0 Hz, 1H), 8.92 (d, J=2.0 Hz, 1H), 8.39 (t, J=2.0 Hz, 1H), 7.65 (m, 2H), 7.56 (d, J=1.3 Hz, 1H), 7.48 (m, 1H), 7.31 (dd, J=8.4, 1.7 Hz, 1H), 7.27 (m, 2H), 7.06 (s, 1H), 5.39 (s, 2H), 5.32 (s, 2H), 4.46 (d, J=13.1 Hz, 1H), 4.32 (d, J=13.1 Hz, 1H), 4.06 (dt, J=11.2, 3.6 Hz, 2H), 3.64 (td, J=11.2, 3.6 Hz, 2H), 3.52 (dd, J=10.5, 3.1 Hz, 1H), 3.39-3.35 (m, 2H), 2.93 (m, 1H), 2.27 (s, 3H), 2.24 (m, 1H), 2.14 (m, 2H), 2.08-2.00 (m, 2H), 1.93-1.75 (m, 3H), 1.70 (m, 1H), 1.59-1.49 (m, 1H).

Intermediate: 2-(8-oxabicyclo[3.2.1]octan-3-yl)-5-bromobenzo[d]oxazole was synthesized in a similar manner.

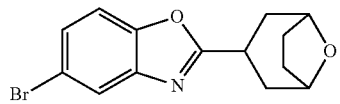 [SMILES: Brc1ccc2oc(C3CC4CCC(C3)O4)nc2c1]

375 mgs of N-(5-bromo-2-hydroxyphenyl)-8-oxabicyclo [3.2.1]octane-3-carboxamide (81% yield) was obtained as a tan solid. The LC/MS data was obtained on a Shimadzu analytical LCMS (ESI+) at 220 nm using the following set of conditions: Waters Aquity BEH 1.7 □m C18, 2.1×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.862 min., m/z 381.20 & 383.15 (M+H), 90% purity. $^1$H NMR (500 MHz, CD$_3$OD) δ 9.11 (br. s., 1H), 7.99 (m, 1H), 7.10 (dd, J=8.6, 2.4 Hz, 1H), 6.78 (d, J=8.6 Hz, 1H), 4.45 (m, 2H), 3.11-2.98 (m, 1H), 2.08-1.86 (m, 6H), 1.69 (m, 2H).

31.4 mgs of 2-(8-oxabicyclo[3.2.1]octan-3-yl)-5-bromobenzo[d]oxazole (23% yield) was obtained as a light yellow solid. The LC/MS data was obtained on a Shimadzu analytical LCMS (ESI+) at 220 nm using the following set of conditions: Waters Aquity BEH 1.7 µm C18, 2.1×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.502 min., m/z 308.10 & 310.10 (M+H), 90% purity. $^1$H NMR (500 MHz, CDCl$_3$) δ 7.79 (s, 1H), 7.40 (m, 1H), 7.34 (m, 1H), 4.52 (br. s., 2H), 3.48-3.33 (m, 1H), 2.17 (m, 2H), 2.07 (m, 2H), 1.99-1.77 (m, 4H).

Example 1018: (2S)-1-(4-((3-(2-(8-oxabicyclo [3.2.1]octan-3-yl)benzo[d]oxazol-5-yl)-2-methylbenzyl)oxy)-5-chloro-2-((5-cyanopyridin-3-yl)methoxy) benzyl)piperidine-2-carboxylic Acid

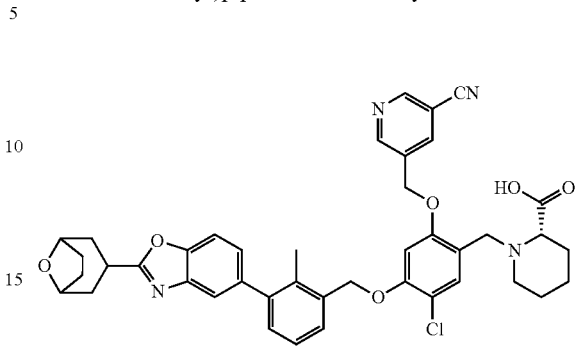

The crude material was purified via preparative HPLC using the following conditions: Waters XBridge 5 µm C18, 30×100 mm where mobile phase A was 5:95 acetonitrile: water with 10 mM ammonium acetate and mobile phase B was 95:5 acetonitrile:water with 10 mM ammonium acetate at a complex gradient of 30% B over 25 minutes then 50% B for 10 minutes and finally 50-100% B over 5 minutes at a flow rate of 30 mL/minute. Fractions containing the desired product were combined and evaporated. The yield of the product was 10.4 mg (18% yield), and its estimated purity by LCMS analysis was 98%.

Two analytical LC/MS injections were used to determine the final purity.

Injection 1 conditions: Waters Xbridge 3.5 µm C18, 3.0×150 mm where mobile phase A was 5:95 acetonitrile: water with 10 mM ammonium acetate; mobile phase B was 95:5 acetonitrile:water with 10 mM ammonium acetate at a temperature of 50° C. at a gradient of 10-100% B over 15 minutes with a 5-minute hold at 100% B at a flow rate of 0.5 mL/minute at a UV wavelength of 220 nm.

Injection 2 conditions: Waters Sunfire 3.5 µm C18, 3.0× 150 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 10-100% B over 15 minutes with a 5-minute hold at 100% B at a flow rate of 0.5 mL/minute at a UV wavelength of 220 nm.

Analysis condition 1: Retention time=14.08 min; 98% purity.

Analysis condition 2: Retention time=9.13 min; 99% purity.

The LC/MS data was obtained on a Shimadzu analytical LCMS (ESI+) at 220 nm using the following set of conditions: Waters Aquity BEH 1.7 µm C18, 2.1×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.485 min., m/z 733.20 & 734.20 (M+H).

$^1$H NMR (400 MHz, CD$_3$OD) δ 8.94 (m, 2H), 8.39 (m, 1H), 7.66 (m, 2H), 7.55 (m, 1H), 7.48 (m, 1H), 7.27 (m, 3H), 7.05 (m, 1H), 5.38 (s, 2H), 5.33 (s, 2H), 4.54 (m, 2H), 4.45 (m, 1H), 4.32 (m, 1H), 3.59 (m, 1H), 3.49 (m, 1H), 2.92 (m, 1H), 2.27 (s, 3H), 2.14-1.94 (m, 9H), 1.78 (m, 3H), 1.66 (m, 1H), 1.53 (m, 1H), 1.30 (m, 1H).

Example 1019 and Example 1020 were prepared according to the following scheme.

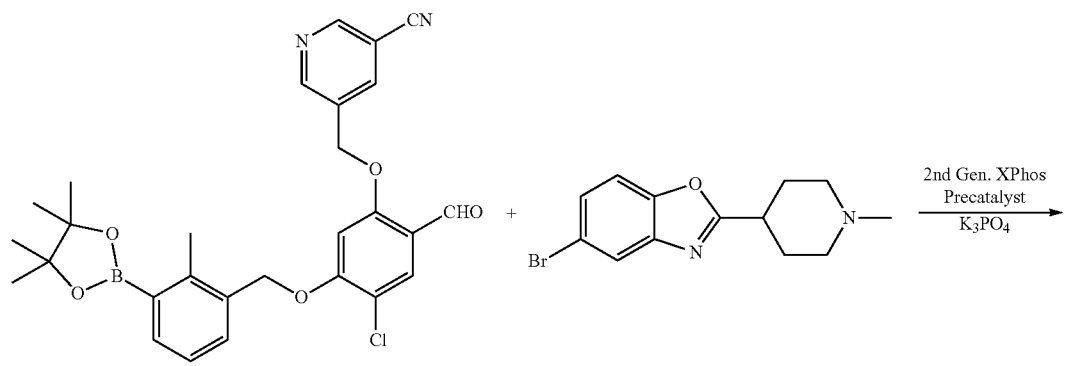
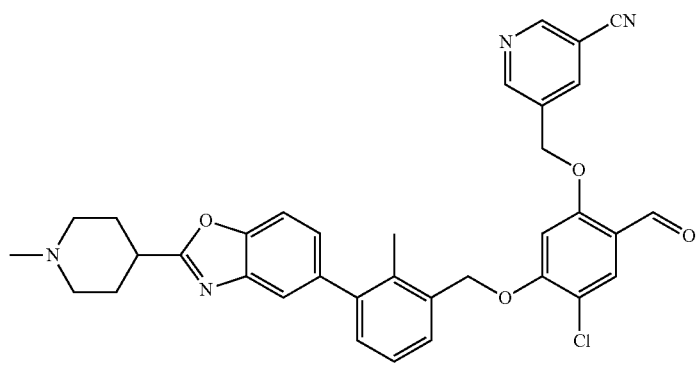 [SMILES: Cc1c(COc2cc(OCc3cncc(C#N)c3)c(C=O)cc2Cl)cccc1-c1ccc2oc(C3CCN(C)CC3)nc2c1]
Example 1019
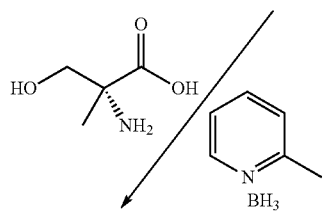
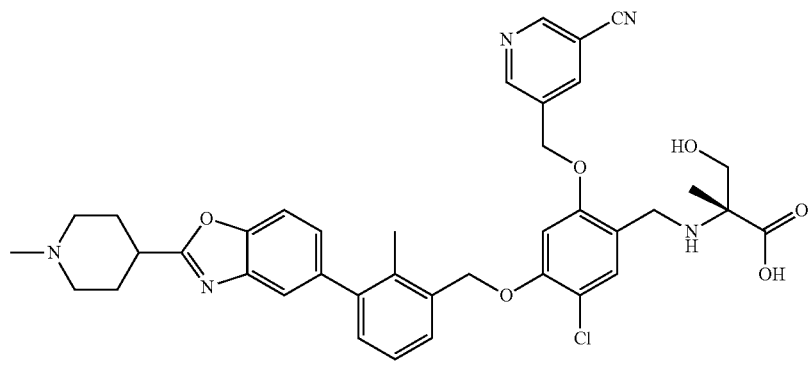 [SMILES: Cc1c(COc2cc(OCc3cncc(C#N)c3)c(CN[C@](C)(CO)C(=O)O)cc2Cl)cccc1-c1ccc2oc(C3CCN(C)CC3)nc2c1]
Example 1020

Example 1019: 5-((4-chloro-2-formyl-5-((2-methyl-3-(2-(1-methylpiperidin-4-yl)benzo[d]oxazol-5-yl)benzyl)oxy)phenoxy)methyl)nicotinonitrile

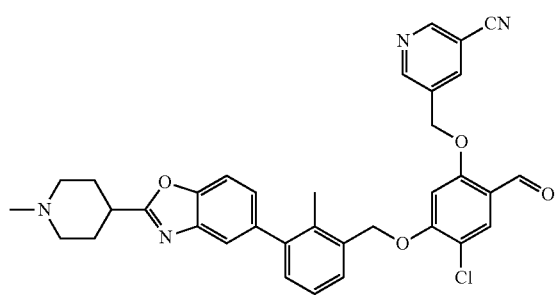

To a sealed tube was added 5-bromo-2-(1-methylpiperidin-4-yl)benzo[d]oxazole (85 mg, 0.289 mmol), 5-((4-chloro-2-formyl-5-((2-methyl-3-(4,4,5,5-tetramethyl-1,3,2-dioxaborolan-2-yl)benzyl)oxy) phenoxy)methyl) nicotinonitrile (150 mg, 0.289 mmol), THF (4.5 mL), water (1.5 mL), potassium phosphate, tribasic (245 mg, 1.157 mmol), and second generation XPhos precatalyst (22.75 mg, 0.029 mmol). The mixture was de-gassed/flushed with nitrogen then heated overnight at 80° C. The reaction mixture was cooled, the solvent evaporated. The residue taken up in ethyl acetate, washed with water, brine, dried over sodium sulfate, filtered and evaporated. The resulting oil was triturated with 3:1 cold diethyl ether/hexanes to produce 148.8 mgs of 5-((4-chloro-2-formyl-5-((2-methyl-3-(2-(1-methylpiperidin-4-yl)benzo[d]oxazol-5-yl)benzyl)oxy)phenoxy) methyl)nicotinonitrile (85% yield) as a light tan powder. The LC/MS data was obtained on a Shimadzu analytical LCMS (ESI+) at 220 nm using the following set of conditions: Waters Aquity BEH 1.7 µm C18, 2.1×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.437 min., m/z 607.20, 609.20 (M+H), 93% purity. $^1$H NMR (500 MHz, DMSO-d$_6$) δ 10.24 (s, 1H), 9.04 (d, J=1.9 Hz, 2H), 8.56 (s, 1H), 7.74 (m, 2H), 7.63 (d, J=1.1 Hz, 1H), 7.54 (d, J=6.1 Hz, 1H), 7.40-7.20 (m, 4H), 5.50 (s, 2H), 5.44 (s, 2H), 3.43 (m, 1H), 3.04-2.96 (m, 1H), 2.81 (m, 2H), 2.67-2.58 (m, 1H), 2.24 (s, 3H), 2.20 (s, 3H), 2.14-2.03 (m, 3H), 1.86 (m, 1H).

Example 1020: (R)-2-((5-chloro-2-((5-cyanopyridin-3-yl)methoxy)-4-((2-methyl-3-(2-(1-methylpiperidin-4-yl)benzo[d]oxazol-5-yl)benzyl)oxy)benzyl)amino)-3-hydroxy-2-methylpropanoic Acid

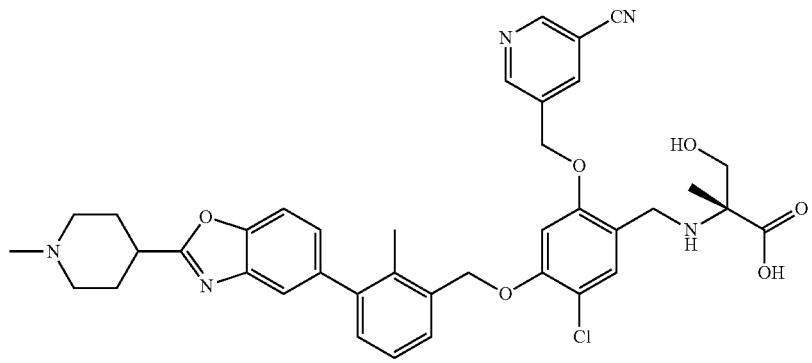

To a vial was added 5-((4-chloro-2-formyl-5-((2-methyl-3-(2-(1-methylpiperidin-4-yl)benzo[d]oxazol-5-yl)benzyl)oxy)phenoxy)methyl)nicotinonitrile (25 mg, 0.041 mmol) in DMF (1 mL) along with acetic acid (0.100 mL), and (R)-2-amino-3-hydroxy-2-methylpropanoic acid (12.26 mg, 0.103 mmol). The vial was sealed and the mixture stirred for 1 hour at room temperature. To the reaction mixture was then added borane-2-picoline complex (5.29 mg, 0.049 mmol) and the mixture stirred overnight at room temperature. The crude material was purified via preparative LC/MS using the following conditions: Waters XBridge 5 μm C18, 19×200 mm where mobile phase A was 5:95 acetonitrile:water with 10 mM ammonium acetate and mobile phase B was 95:5 acetonitrile:water with 10 mM ammonium acetate at a gradient of 15-80% B over 25 minutes with a 5-minute hold at a flow rate of 20 mL/minute. Fractions containing the desired product were combined and dried via centrifugal evaporation. The yield of the product, (R)-2-((5-chloro-2-((5-cyanopyridin-3-yl)methoxy)-4-((2-methyl-3-(2-(1-methylpiperidin-4-yl)benzo[d]oxazol-5-yl)benzyl)oxy)benzyl)amino)-3-hydroxy-2-methylpropanoic acid was 4.3 mg (14% yield), and its estimated purity by LCMS analysis was 94%. Two analytical LC/MS injections were used to determine the final purity.

Injection 1 conditions: Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Injection 2 conditions: Waters Acquity UPLC BEH 1.7 μm C18, 2.1×50 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 3 minutes with a 0.75-minute hold at 100% B at a flow rate of 1.0 mL/minute at a UV wavelength of 220 nm.

Analysis condition 1: Retention time=1.394 min; ESI-MS (+) m/z=710.1 (M+H)

Analysis condition 2: Retention time=1.435 min; ESI-MS (+) m/z=710.0 (M+H)

$^1$H NMR (500 MHz, DMSO-$d_6$) δ 8.95 (m, 1H), 8.89 (m, 1H), 8.39 (m, 1H), 7.70 (m, 1H), 7.52 (m, 2H), 7.40 (m, 1H), 7.31-7.18 (m, 3H), 7.02 (m, 1H), 5.33 (m, 2H), 5.24 (m, 2H), 4.00 (m, 4H), 3.07 (m, 1H), 2.92 (m, 2H), 2.41-2.24 (m, 4H), 2.22-2.07 (m, 4H), 1.88 (m, 2H), 1.76 (m, 2H), 1.24 (s, 3H).

Example 1021: 5-((4-chloro-2-(hydroxymethyl)-5-((2-methyl-3-(2-(1-methylpiperidin-4-yl)benzo[d]oxazol-5-yl)benzyl)oxy)phenoxy)methyl)nicotinonitrile

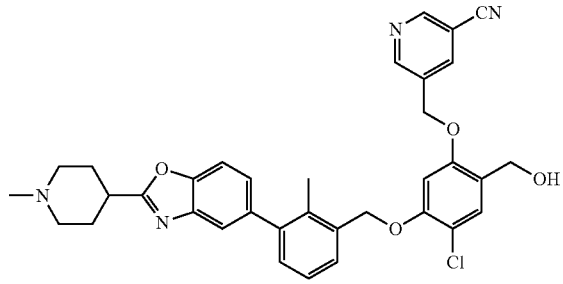 [SMILES: Cc1c(COc2cc(OCc3cncc(C#N)c3)c(CO)cc2Cl)cccc1-c1ccc2oc(C3CCN(C)CC3)nc2c1]

Example 1021 was isolated from the reaction mixture for Example 1020. The crude material was purified via preparative LC/MS using the following conditions: Waters XBridge 5 μm C18, 19×200 mm where mobile phase A was 5:95 acetonitrile: water with 10 mM ammonium acetate and mobile phase B was 95:5 acetonitrile:water with 10 mM ammonium acetate at a gradient of 15-80% B over 25 minutes with a 5-minute hold at a flow rate of 20 mL/minute. Fractions containing the desired product were combined and dried via centrifugal evaporation. The yield of the product, 5-((4-chloro-2-(hydroxymethyl)-5-((2-methyl-3-(2-(1-methylpiperidin-4-yl)benzo[d]oxazol-5-yl)benzyl)oxy)phenoxy)methyl)nicotinonitrile, was 2.6 mg (10% yield), and its estimated purity by LCMS analysis was 96.2%.

Two analytical LC/MS injections were used to determine the final purity.

Injection 1 conditions: Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Injection 2 conditions: Waters Acquity UPLC BEH 1.7 μm C18, 2.1×50 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 3 minutes with a 0.75-minute hold at 100% B at a flow rate of 1.0 mL/minute at a UV wavelength of 220 nm.

Analysis condition 1: Retention time=1.944 min; ESI-MS (+) m/z=609.0 (M+H)

Analysis condition 2: Retention time=1.884 min; ESI-MS (+) m/z=609.0 (M+H)

Intermediate: 5-bromo-2-(1-phenylpiperidin-4-yl)benzo[d]oxazole

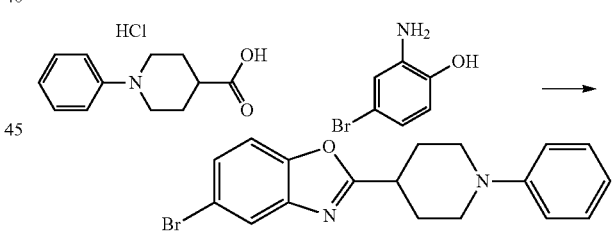

To 2-amino-4-bromophenol (300 mg, 1.596 mmol) and 1-phenylpiperidine-4-carboxylic acid hydrochloride (386 mg, 1.596 mmol) was added polyphosphoric acid (5 g). The mixture was heated for 3.5 hours at 190° C. To the reaction mixture at 0° C. was added dropwise 6 mL of water with manual stirring. To the reaction mixture, was added dropwise, aq 2M NaOH until pH reached ~7. To the thick purple mixture was added 30 mL of ethyl acetate, the product extracted, washed with water, brine, dried over sodium sulfate, filtered and evaporated to give 158.9 mgs of 5-bromo-2-(1-phenylpiperidin-4-yl)benzo[d]oxazole as a red solid (28% yield) which by LCMS had a purity of 95%. The LC/MS data was obtained on a Shimadzu analytical LCMS (ESI+) at 220 nm using the following set of conditions: Waters Aquity BEH 1.7 μm C18, 2.1×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.202 min., m/z 357.15 & 359.15 (M+H), 95% purity. $^1$H NMR (500 MHz, DMSO-$d_6$) δ 7.96 (d, J=1.9 Hz, 1H), 7.70 (d, J=8.6 Hz, 1H), 7.55 (d, J=1.9, 8.6 Hz, 1H), 7.27-7.19 (m, 2H), 6.99 (d, J=8.0 Hz, 2H), 6.78 (t, J=7.2 Hz, 1H), 3.74 (dt, J=12.7, 3.4 Hz, 2H), 3.25 (m, 1H), 2.98-2.88 (m, 2H), 2.19 (dd, J=13.3, 2.9 Hz, 2H), 1.98-1.88 (m, 2H).

Example 1022: (S)-1-(5-chloro-2-((5-cyanopyridin-3-yl)methoxy)-4-((2-methyl-3-(2-(1-phenylpiperidin-4-yl)benzo[d]oxazol-5-yl)benzyl)oxy)benzyl)piperidine-2-carboxylic Acid

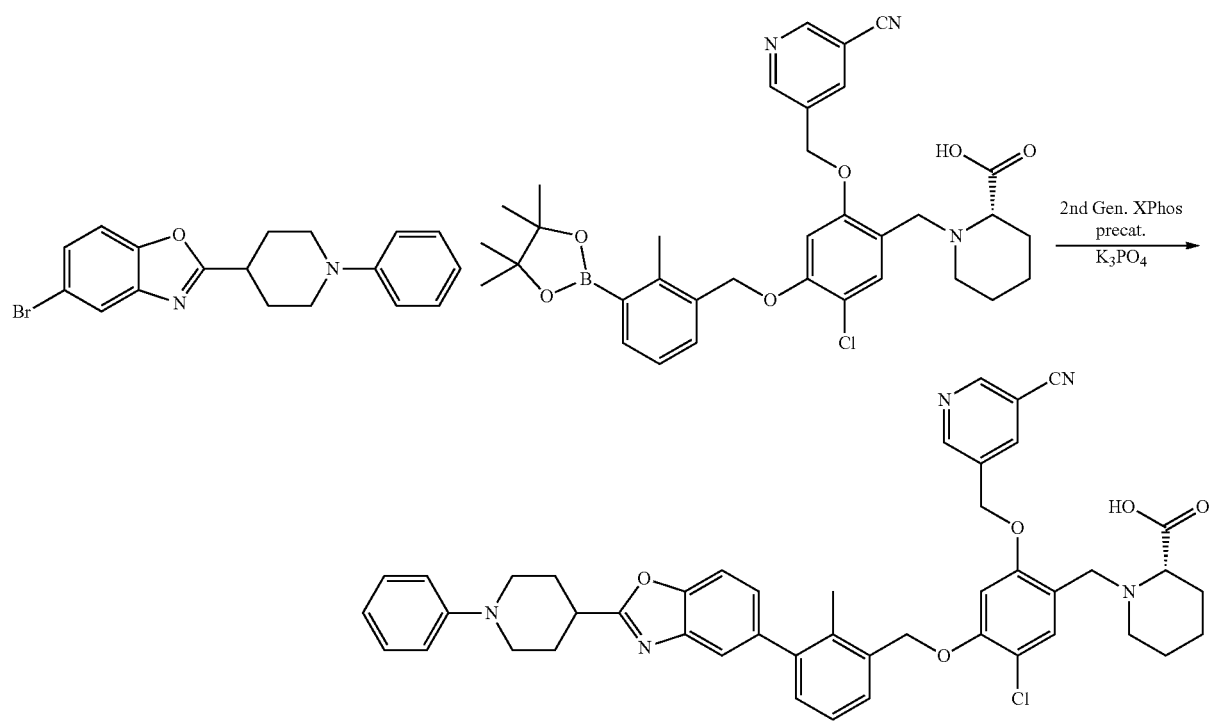

Example 1022

To a sealed tube was added 5-bromo-2-(1-phenylpiperidin-4-yl)benzo[d]oxazole (28.3 mg, 0.079 mmol), THF (3 mL), (S)-1-(5-chloro-2-((5-cyanopyridin-3-yl)methoxy)-4-((2-methyl-3-(4,4,5,5-tetramethyl-1,3,2-dioxaborolan-2-yl)benzyl)oxy)benzyl)piperidine-2-carboxylic acid (50 mg, 0.079 mmol), potassium phosphate, tribasic (42.0 mg, 0.198 mmol), water (1 mL), and second generation XPhos precatalyst (7.80 mg, 9.91 μmol). The vessel was sealed, the mixture de-gassed/flushed with nitrogen and then heated at 75° C. overnight. The crude material was purified via preparative LC/MS using the following conditions: Waters XBridge 5 μm C18, 19×200 mm where mobile phase A was 5:95 acetonitrile:water with 10 mM ammonium acetate and mobile phase B was 95:5 acetonitrile:water with 10 mM ammonium acetate at a gradient of 50-90% B over 20 minutes with a 5-minute hold at a flow rate of 20 mL/minute. Fractions containing the desired product were combined and dried via centrifugal evaporation. The yield of the product was 17.5 mg (28.1% yield), and its estimated purity by LCMS analysis was 99%.
Two analytical LC/MS injections were used to determine the final purity.

Injection 1 conditions: Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.
Injection 2 conditions: Waters Acquity UPLC BEH 1.7 μm C18, 2.1×50 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 3 minutes with a 0.75-minute hold at 100% B at a flow rate of 1.0 mL/minute at a UV wavelength of 220 nm.

Analysis condition 1: Retention time=2.494 min; ESI-MS (+) m/z=782.0 (M+H)
Analysis condition 2: Retention time=1.846 min; ESI-MS (+) m/z=782.0 (M+H)
$^1$H NMR (500 MHz, DMSO-$d_6$) δ9.02 (m, 2H), 8.47 (s, 1H), 7.77 (d, J=8.5 Hz, 1H), 7.64 (s, 1H), 7.53 (d, J=6.7 Hz, 1H), 7.45 (s, 1H), 7.36-7.20 (m, 5H), 7.14 (s, 1H), 7.01 (d, J=7.9 Hz, 2H), 6.79 (t, J=7.2 Hz, 1H), 5.35 (br. s., 2H), 5.29 (s, 2H), 3.85-3.73 (m, 4H), 3.62 (d, J=13.7 Hz, 1H), 3.13 (m, 1H), 2.94 (m, 4H), 2.33-2.15 (m, 5H), 1.97 (m, 2H), 1.80 (m, 1H), 1.73 (m, 1H), 1.49 (m, 3H), 1.37 (m, 1H).

Example 1023: (S)-1-(5-chloro-2-methoxy-4-((2-methyl-3-(2-(1-phenylpiperidin-4-yl)benzo[d]oxazol-5-yl)benzyl)oxy)benzyl)piperidine-2-carboxylic Acid

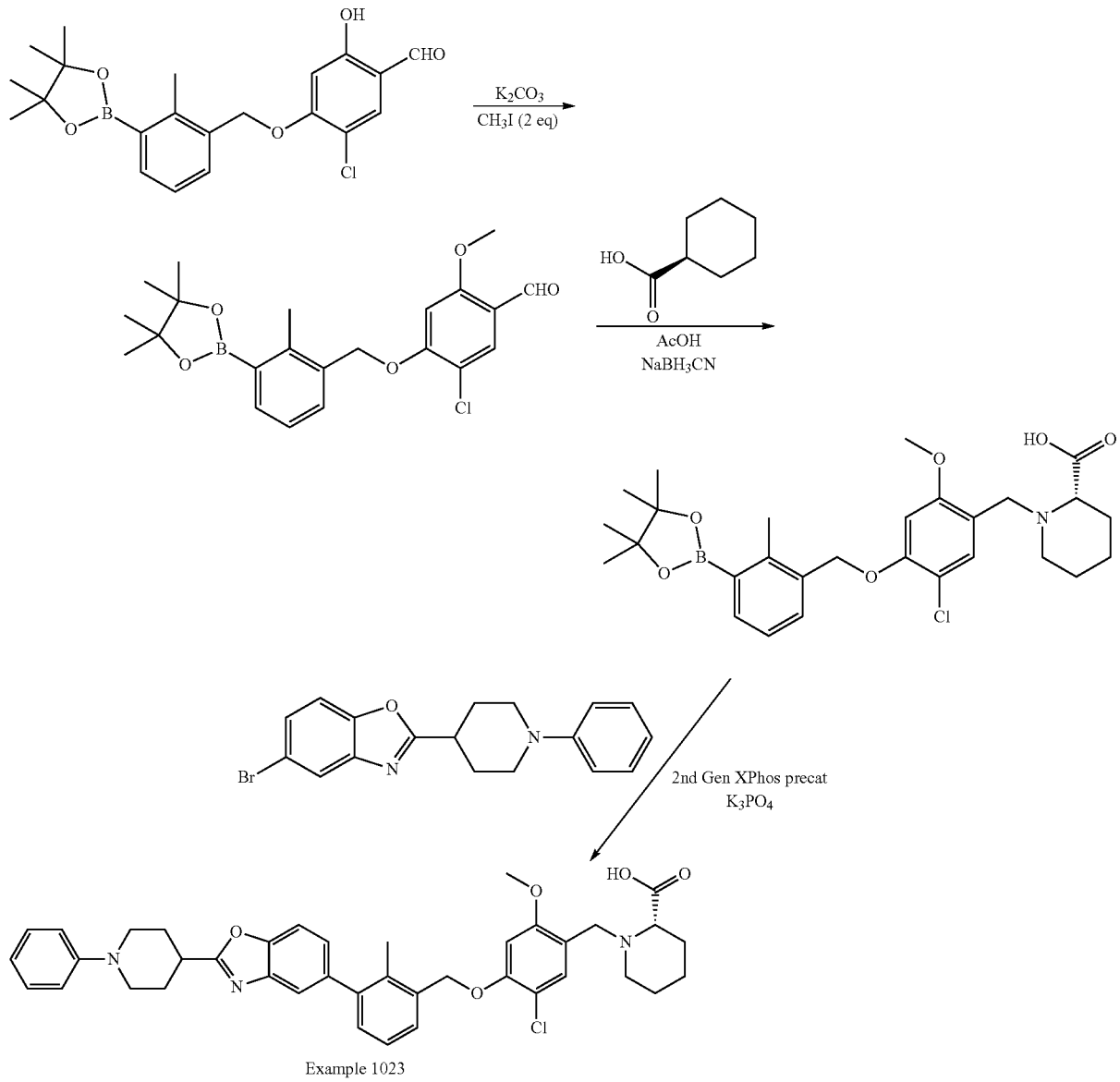

Example 1023

Example 1023 was prepared according to the above scheme and the following procedure: To 5-chloro-2-hydroxy-4-((2-methyl-3-(4,4,5,5-tetramethyl-1,3,2-dioxaborolan-2-yl)benzyl)oxy)benzaldehyde (1.41 g, 3.50 mmol) in DMF (23 mL) under a nitrogen atmosphere was added potassium carbonate (1.113 g, 8.05 mmol) and iodomethane (0.436 ml, 7.00 mmol). The mixture was stirred overnight at room temperature. The crude product was diluted with 75 mL of DCM, washed with water, brine, dried over sodium sulfate, filtered and evaporated to give 1.4 g (88%) of 5-chloro-2-methoxy-4-((2-methyl-3-(4,4,5,5-tetramethyl-1,3,2-dioxaborolan-2-yl)benzyl)oxy)benzaldehyde as a light tan solid. The LC/MS data was obtained on a Shimadzu analytical LCMS (ESI+) at 220 nm using the following set of conditions: Waters Aquity BEH 1.7 mm C18, 2.1×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=2.044 min., m/z 417.25, 419.25 (M+H), 90% purity. $^1$H NMR (500 MHz, DMSO-$d_6$) δ10.16 (s, 1H), 7.69-7.65 (m, 2H), 7.64-7.59 (m, 1H), 7.25 (t, J=7.5 Hz, 1H), 7.11 (s, 1H), 5.38 (s, 2H), 4.01 (s, 3H), 2.54 (s, 3H), 1.32 (s, 12H).

To a RBF was added acetic acid (27.5 μl, 0.480 mmol), DCE (1 mL), ethanol (3 mL), THF (1 mL), 20 mgs of oven dried, ground 4 Å sieves, L-pipecolic acid (62.0 mg, 0.480 mmol), and 5-chloro-2-methoxy-4-((2-methyl-3-(4,4,5,5-tetramethyl-1,3,2-dioxaborolan-2-yl)benzyl)oxy)benzaldehyde (100 mg, 0.240 mmol). The RBF was sealed, the mixture placed under a nitrogen atmosphere and the mixture stirred at room temperature for 1 hour. To a small vial was added THF (1 ml) and sodium cyanotrihydroborate (30.2 mg, 0.480 mmol). The mixture was briefly sonicated into solution then taken up in a syringe. The resulting solution was dripped into the above reaction mixture manually over 4 hours. The reaction mixture was then stirred overnight under nitrogen. The crude product was diluted with ethyl acetate, washed with 1.5M potassium phosphate, water, brine, dried over sodium sulfate, filtered and evaporated to give 134.7 mgs of (S)-1-(5-chloro-2-methoxy-4-((2-methyl-3-(4,4,5,5-tetramethyl-1,3,2-dioxaborolan-2-yl)benzyl)oxy)benzyl) piperidine-2-carboxylic acid as a white solid (85% yield, 80% purity). The LC/MS data was obtained on a Shimadzu analytical LCMS (ESI+) at 220 nm using the following set of conditions: Waters Aquity BEH 1.7 mm C18, 2.1×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.554 min., m/z 530.35 (M+H), 80% purity. $^1$H NMR (500 MHz, DMSO-$d_6$) δ7.64 (m, 1H), 7.59 (m, 1H), 7.40 (s, 1H), 7.28-7.21 (m, 1H), 6.95 (S, 1H), 5.23 (s, 2H), 3.84 (s, 3H), 3.77-3.71 (m, 1H), 3.69-3.62 (m, 1H), 3.13 (m, 1H), 2.90 (m, 1H), 2.54 (s, 3H), 2.32 (m, 1H), 1.82 (m, 1H), 1.76-1.68 (m, 1H), 1.52 (m, 3H), 1.41-1.36 (m, 1H), 1.32 (s, 12H).

To a sealed tube was added 5-bromo-2-(1-phenylpiperidin-4-yl)benzo[d]oxazole (35.4 mg, 0.099 mmol), THF (3 mL), (S)-1-(5-chloro-2-methoxy-4-((2-methyl-3-(4,4,5,5-tetramethyl-1,3,2-dioxaborolan-2-yl)benzyl)oxy)benzyl)piperidine-2-carboxylic Acid (68.25 mg, 0.129 mmol), potassium phosphate, tribasic (52.6 mg, 0.248 mmol), water (1 mL), and second generation XPhos precatalyst (7.80 mg, 9.91 μmol). The vessel was sealed, the mixture de-gassed/flushed with nitrogen then heated overnight at 75° C. The crude material was purified via preparative LC/MS using the following conditions: Waters XBridge 5 μm C18, 19×200 mm where mobile phase A was 5:95 acetonitrile: water with 10 mM ammonium acetate and mobile phase B was 95:5 acetonitrile:water with 10 mM ammonium acetate at a gradient of 47-87% B over 23 minutes with a 4-minute hold at a flow rate of 20 mL/minute. Fractions containing the desired product were combined and dried via centrifugal evaporation. The material was further purified via preparative LC/MS using the following conditions: Waters XBridge 5 μm C18, 19×200 mm where mobile phase A was 5:95 methanol: water with 10 mM ammonium acetate and mobile phase B was 95:5 acetonitrile:water with 10 mM ammonium acetate at a gradient of 50-90% B over 25 minutes with a 5-minute hold at a flow rate of 20 mL/minute. Fractions containing the desired product were combined and dried via centrifugal evaporation. The yield of Example 1023, (S)-1-(5-chloro-2-methoxy-4-((2-methyl-3-(2-(1-phenylpiperidin-4-yl)benzo[d]oxazol-5-yl)benzyl)oxy)benzyl)piperidine-2-carboxylic acid, was 1.1 mg (2% yield), and its estimated purity by LCMS analysis was 92%.

Two analytical LC/MS injections were used to determine the final purity.

Injection 1 conditions: Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm. Injection 2 conditions: Waters Acquity UPLC BEH 1.7 μm C18, 2.1×50 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 3 minutes with a 0.75-minute hold at 100% B at a flow rate of 1.0 mL/minute at a UV wavelength of 220 nm. Analysis condition 1: Retention time=2.567 min; ESI-MS(+) m/z=680.0 (M+H); Analysis condition 2: Retention time=1.866 min; ESI-MS(+) m/z=680.0 (M+H); $^1$H NMR (400 MHz, DMSO-$d_6$) δ7.76 (d, J=8.3 Hz, 1H), 7.62 (d, J=1.7 Hz, 1H), 7.57 (d, J=6.8 Hz, 1H), 7.50 (s, 1H), 7.33-7.19 (m, 5H), 7.03-6.97 (m, 2H), 6.92 (s, 1H), 6.78 (t, J=7.2 Hz, 1H), 5.27 (s, 2H), 3.82 (s, 3H), 3.79-3.67 (m, 2H), 3.30-3.21 (m, 2H), 2.94 (t, J=10.9 Hz, 3H), 2.84 (m, 1H), 2.65 (dd, J=8.1, 3.9 Hz, 1H), 2.28-2.16 (m, 4H), 2.05-1.86 (m, 3H), 1.74-1.50 (m, 3H), 1.42 (m, 2H), 1.24 (m, 2H).

Intermediates: Methyl 4-(5-bromobenzo[d]oxazol-2-yl) cyclohexanecarboxylate & 4-(5-bromobenzo[d]oxazol-2-yl) cyclohexanecarboxylic Acid

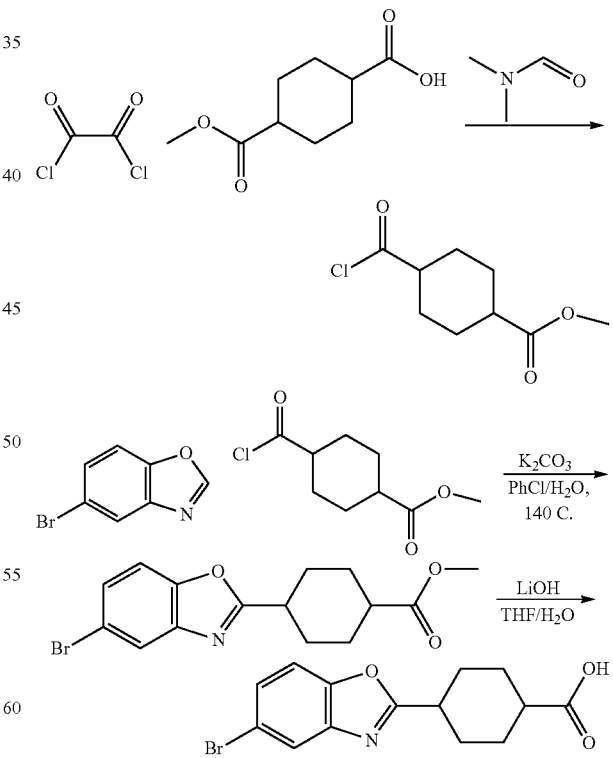

To a RBF was added at 0° C., under nitrogen, 4-(methoxycarbonyl) cyclohexanecarboxylic acid (0.484 g, 2.60 mmol), dry DCM (10 mL), dry DMF (0.040 mL, 0.520 mmol), and dropwise oxalyl chloride (0.854 mL, 5.72 mmol). The ice-bath was removed and the mixture was stirred for 45 minutes under nitrogen. The volatiles were removed on the rotovap, the crude oil diluted with dry DCM and evaporation repeated to give crude methyl 4-(chlorocarbonyl)cyclohexanecarboxylate. To a vial was added freshly synthesized methyl 4-(chlorocarbonyl)cyclohexane-carboxylate (2.60 mmol assumed), PhCl (2 mL), 5-bromobenzoxazole (257 mg, 1.3 mmol) and potassium carbonate (27.6 mg, 0.200 mmol) in water (0.667 mL). The vial was sealed and the mixture stirred overnight at 140° C. The mixture was cooled and volatiles were removed. The crude product was taken up in 1:1 ethylacetate/DCM, washed with minimal water, brine, dried over sodium sulfate, filtered, and evaporated. The crude reaction mixture was then taken up in 6 mL of acetonitrile/DMF and purified using a Shimadzu preparative HPLC employing acetonitrile/water/ammonium acetate where solvent A was 5% acetonitrile/95% water/10 mM ammonium acetate and solvent B was 5% water/95% acetonitrile/10 mM ammonium acetate with a Waters Sunfire 5 μm C18 30×100 mm column at a gradient of 25-100% B and a flow rate of 40 mL/min. over 15 minutes with a 5 minute hold. Methyl 4-(5-bromobenzo[d]oxazol-2-yl)cyclohexanecarboxylate was obtained as a ~1:1 mixture of cis and trans isomers by NMR analysis and as a peach colored solid (100.8 mgs, 23% yield). The LC/MS data was obtained on a Shimadzu analytical LCMS (ESI+) at 220 nm using the following set of conditions: Waters Aquity BEH 1.7 μm C18, 2.1×50 mm column, with a gradient of 2-98% B (B=100% HPLC grade acetonitrile/0.05% trifluoroacetic acid), (A=100% HPLC grade water/0.05% trifluoroacetic acid), in 2 minutes with a gradient time of 1.5 minute at a flow rate of 0.8 mL/minute. LCMS Rt=1.334 min., m/z 337.9 & 339.9 (M+H).

To a vial was added methyl 4-(5-bromobenzo[d]oxazol-2-yl)cyclohexanecarboxylate (20 mg, 0.059 mmol) in THF (2 mL) along with lithium hydroxide (7.08 mg, 0.296 mmol) in water (0.400 mL). The mixture was stirred overnight at room temperature. The volatiles were removed, the resulting white residue taken up in ethylacetate, washed with NH₄Cl, brine, dried over sodium sulfate, filtered and evaporated to give 18.7 mgs of 4-(5-bromobenzo[d]oxazol-2-yl)cyclohexanecarboxylic acid as a white solid. The LC/MS data was obtained on a Shimadzu analytical LCMS (ESI+) at 220 nm using the following set of conditions: Waters Aquity BEH 1.7 mm C18, 2.1×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=2.114 min., m/z 324.15, 326.15 (M+H), 95% purity. ¹H NMR (500 MHz, CD₃OD) δ 7.82 (m, 1H), 7.54 (m, 1H), 7.51 (m, 1H), 3.20 (m, 1H), 3.02 (m, 1H), 2.61 (m, 1H), 2.33 (m, 1H), 2.30 (m, 1H), 2.16 (m, 1H), 2.03 (m, 2H), 1.81 (m, 1H), 1.75-1.59 (m, 1H).

Example 1024: (S)-1-(5-chloro-2-((5-cyanopyridin-3-yl)methoxy)-4-((3-(2-(4-benzo[d]oxazol-5-yl)-2-methylbenzyl)oxy)benzyl)piperidine-2-carboxylic Acid

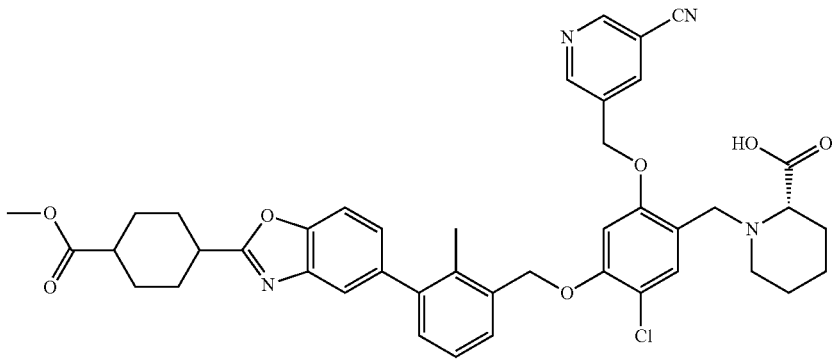 [SMILES: COC(=O)C1CCC(c2nc3cc(-c4cccc(COc5cc(OCc6cncc(C#N)c6)c(CN6CCCC[C@H]6C(=O)O)cc5Cl)c4C)ccc3o2)CC1]

To a sealed tube was added (S)-1-(5-chloro-2-((5-cyanopyridin-3-yl)methoxy)-4-((2-methyl-3-(4,4,5,5-tetramethyl-1,3,2-dioxaborolan-2-yl)benzyl)oxy)benzyl)piperidine-2-carboxylic acid (30 mg, 0.047 mmol), THF (3 mL), water (1 mL), methyl 4-(5-bromobenzo[d]oxazol-2-yl)cyclohexanecarboxylate (16.05 mg, 0.047 mmol), potassium phosphate, tribasic (25.2 mg, 0.119 mmol), and second generation XPhos precatalyst (3.74 mg, 4.75 μmol). The vessel was sealed, the mixture de-gassed/flushed with nitrogen, then heated overnight at 80° C. The crude reaction mixture was concentrated, taken up in 4 mL of acetonitrile and purified using a Shimadzu preparative HPLC employing acetonitrile/water/ammonium acetate where solvent A was 5% acetonitrile/95% water/10 mM ammonium acetate and solvent B was 5% water/95% acetonitrile/10 mM ammonium acetate with a Phenomenex Axia C18 30×100 mm 10 μm column at a gradient of 20-100% B and a flow rate of 40 mL/min. over 12 minutes with a 10 minute hold. Fractions were pooled and solvent removed under a stream of nitrogen to give 8.0 mgs (22% yield) of (S)-1-(5-chloro-2-((5-cyanopyridin-3-yl)methoxy)-4-((3-(2-(4-(methoxycarbonyl)cyclohexyl)benzo[d]oxazol-5-yl)-2-methylbenzyl) oxy)benzyl)piperidine-2-carboxylic acid as a white solid with a purity of 96%. The LC/MS data was obtained on a Shimadzu analytical LCMS (ESI+) at 220 nm using the following set of conditions: Waters Aquity BEH 1.7 mm C18, 2.1×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute. LCMS Rt=1.234 min., m/z 763.15, 764.10 (M+H). Two analytical LC/MS injections were used to determine the final purity. Injection 1 conditions: Waters Xbridge 3.5 μm C18, 3.0×150 mm where mobile phase A was 5:95 acetonitrile:water with 10 mM ammonium acetate; mobile phase B was 95:5 acetonitrile:water with 10 mM ammonium acetate at a temperature of 50° C. at a gradient of 10-100% B over 15 minutes with a 5-minute hold at 100%

B at a flow rate of 0.5 mL/minute at a UV wavelength of 220 nm. Injection 2 conditions: Waters Sunfire 3.5 μm C18, 3.0×150 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 10-100% B over 15 minutes with a 5-minute hold at 100% B at a flow rate of 0.5 mL/minute at a UV wavelength of 220 nm.

Analysis condition 1: Retention time=14.68 min; 95% purity.

Analysis condition 2: Retention time=11.30 min; 97% purity.

$^1$H NMR (500 MHz, CD$_3$OD) δ 8.96 (s, 1H), 8.93 (s, 1H), 8.40 (t, J=1.8 Hz, 1H), 7.70-7.61 (m, 2H), 7.57-7.47 (m, 3H), 7.34-7.24 (m, 2H), 7.06 (s, 1H), 5.39 (s, 2H), 5.30 (s, 2H), 4.44 (d, J=12.9 Hz, 1H), 4.30 (d, J=13.1 Hz, 1H), 3.73-3.68 (m, 3H), 3.51 (br d, J=7.9 Hz, 1H), 3.29-3.15 (m, 1H), 3.05 (m, 1H), 2.94 (br t, J=11.0 Hz, 1H), 2.73-2.64 (m, 1H), 2.55-2.41 (m, 1H), 2.36-2.27 (m, 4H), 2.25-2.12 (m, 3H), 2.10-2.00 (m, 3H), 1.87-1.76 (m, 3H), 1.74-1.66 (m, 2H), 1.59-1.43 (m, 1H).

Example 1025 and Example 1026: (S)-1-(2-(4-carboxycyclohexyl)benzo[d]oxazol-5-yl)-2-methylbenzyl)oxy)-5-chloro-2-((5-cyanopyridin-3-yl)methoxy)benzyl)piperidine-2-carboxylic Acid

Example 1025

(Isomer-1, the first eluting isomer): The yield of the product was 11.1 mg (28% yield), and its estimated purity by LCMS analysis was 100%.

Two analytical LC/MS injections were used to determine the final purity.

Injection 1 conditions: Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm.

Injection 2 conditions: Waters Acquity UPLC BEH 1.7 μm C18, 2.1×50 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 3 minutes with a 0.75-minute hold at 100% B at a flow rate of 1.0 mL/minute at a UV wavelength of 220 nm.

Analysis condition 1: Retention time=1.474 min; ESI-MS (+) m/z=749.2 (M+H)

Analysis condition 2: Retention time=1.839 min; ESI-MS (+) m/z=749.2 (M+H)

$^1$H NMR (500 MHz, DMSO-d$_6$) δ 8.98 (dd, J=3.2, 2.0 Hz, 2H), 8.41 (m, 1H), 7.71 (m, 1H), 7.58 (s, 1H), 7.50 (m, 1H),

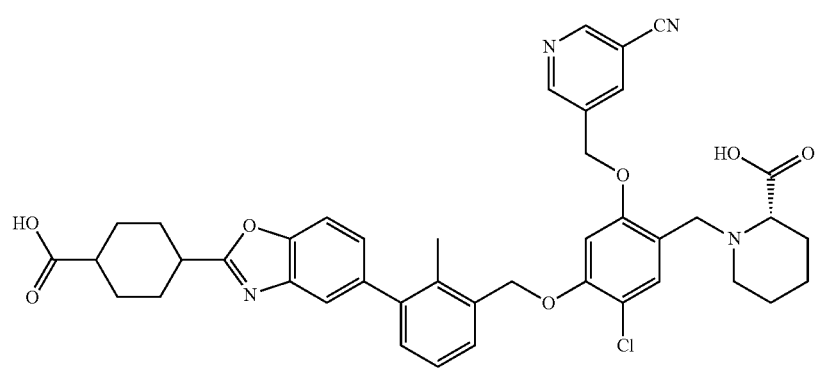

Example 1025 (Isomer-1)
Example 1026 (Isomer-2)

To a sealed tube was added (S)-1-(5-chloro-2-((5-cyanopyridin-3-yl)methoxy)-4-((2-methyl-3-(4,4,5,5-tetramethyl-1,3,2-dioxaborolan-2-yl)benzyl)oxy)benzyl)piperidine-2-carboxylic acid (40 mg, 0.063 mmol), THF (3 mL), water (1 mL), 4-(5-bromobenzo[d]oxazol-2-yl)cyclohexanecarboxylic acid (17.10 mg, 0.053 mmol), potassium phosphate, tribasic (28.0 mg, 0.132 mmol), and second generation XPhos precatalyst (4.15 mg, 5.27 μmop. The vessel was sealed, the mixture de-gassed/flushed with nitrogen, then heated overnight at 80° C. The crude material was purified via preparative LC/MS using the following conditions: Waters XBridge 5 μm C18, 19×200 mm where mobile phase A was 5:95 acetonitrile:water with 10 mM ammonium acetate and mobile phase B was 95:5 acetonitrile:water with 10 mM ammonium acetate at a gradient of 15-55% B over 20 minutes with a 5-minute hold at a flow rate of 20 mL/minute. Fractions containing the desired products were combined and dried via centrifugal evaporation.

7.44 (m, 1H), 7.36-7.22 (m, 3H), 7.10 (m, 1H), 5.34 (s, 2H), 5.27 (s, 2H), 3.85-3.76 (m, 1H), 3.68-3.59 (m, 1H), 3.18-3.11 (m, 1H), 3.08-2.98 (m, 1H), 2.96-2.88 (m, 1H), 2.36-2.26 (m, 2H), 2.26-2.18 (m, 5H), 2.10-2.02 (m, 2H), 1.86-1.60 (m, 4H), 1.59-1.45 (m, 5H), 1.43-1.32 (m, 1H).

Example 1026

(Isomer-2, the second eluting isomer): The yield of the product was 6.3 mg (16% yield), and its estimated purity by LCMS analysis was 99%. Two analytical LC/MS injections were used to determine the final purity. Injection 1 conditions: Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm. Injection 2 conditions: Waters Acquity UPLC BEH 1.7 μm C18, 2.1×50 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 3 minutes with a 0.75-minute hold at 100% B at a flow rate of 1.0 mL/minute at a UV wavelength of 220 nm. Analysis condition 1: Retention time=1.596 min; ESI-MS(+) m/z=749.2 (M+H); Analysis condition 2: Retention time=1.906 min; ESI-MS (+) m/z=749.2 (M+H); $^1$H NMR (500 MHz, DMSO-$d_6$) δ 8.97 (dd, J=3.2, 2.0 Hz, 2H), 8.40 (m, 1H), 7.72-7.68 (m, 1H), 7.57 (s, 1H), 7.52-7.48 (m, 1H), 7.44 (s, 1H), 7.33-7.21 (m, 3H), 7.08 (s, 1H), 5.33 (s, 2H), 5.26 (s, 2H), 3.87-3.79 (m, 1H), 3.70-3.62 (m, 1H), 3.22 (m, 1H), 3.17-3.10 (m, 1H), 2.97-2.87 (m, 1H), 2.36-2.27 (m, 1H), 2.24 (s, 3H), 2.12-2.01 (m, 2H), 1.99-1.69 (m, 9H), 1.57-1.46 (m, 3H), 1.42-1.30 (m, 1H).

The following scheme illustrates the synthesis of Example 1027 to Example 1031.

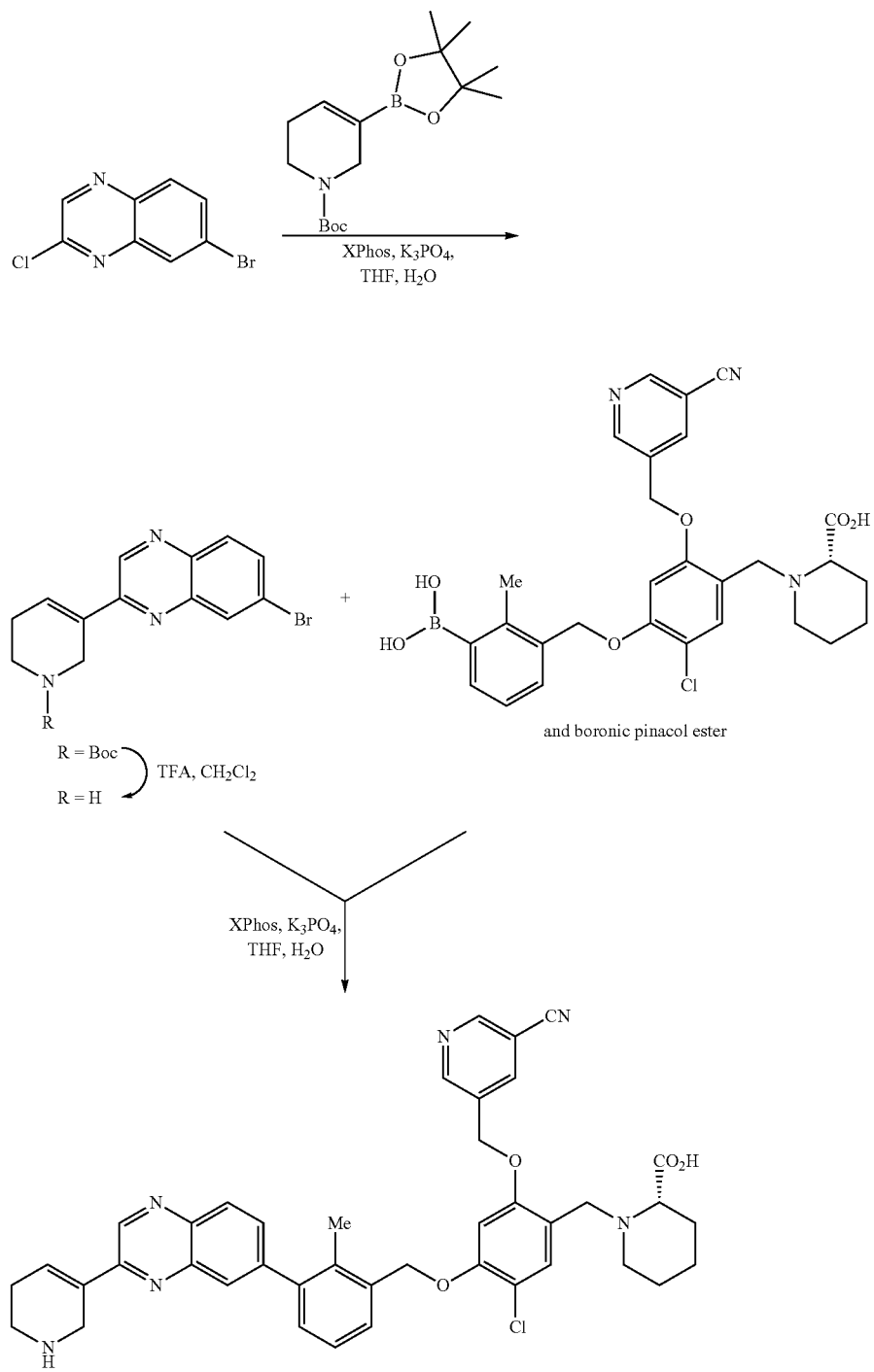

Example 1027

Intermediate: tert-Butyl 5-(7-Bromoquinoxalin-2-yl)-3,6-dihydropyridine-1(2H)-carboxylate

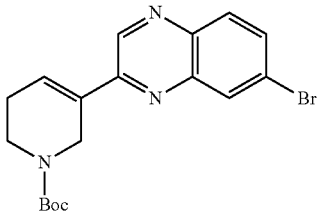 [SMILES: CC(C)(C)OC(=O)N1CCC=C(c2cnc3ccc(Br)cc3n2)C1]

XPhos second generation precatalyst (40.5 mg, 0.051 mmol) was added to a thick-walled, screw top tube containing an argon-degassed solution of 7-bromo-2-chloroquinoxaline (250 mg, 1.027 mmol), tert-butyl 3-(4,4,5,5-tetramethyl-1,3,2-dioxaborolan-2-yl)-5,6-dihydropyridine-1(2H)-carboxylate (317 mg, 1.027 mmol) and potassium phosphate (545 mg, 2.57 mmol) in THF (5 mL) and water (1 mL). The tube was sealed, and the mixture was stirred at rt for 16 h before it was diluted with ethyl acetate and water. The aqueous layer was separated and the organic layer was extracted twice more with ethyl acetate. The combined organic extract was washed with brine, dried over MgSO$_4$, filtered and concentrated to give a light caramel-colored residue. The residue was taken up in a small amount of dichloromethane and charged to a RediSepRf normal phase silica gel Teledyne ISCO 40 g disposable column which was first eluted with hexanes for 120 mL, followed by 0-50% B for 1400 mL where solvent B=ethyl acetate and solvent A=hexanes. After concentration of the eluant, there was isolated the desired product, tert-butyl 3-(7-bromoquinoxalin-2-yl)-5,6-dihydropyridine-1(2H)-carboxylate (56.0 mg, 14% yield) as a light yellow solid. LCMS: t$_R$ (retention time)=1.51 min; LCMS (ESI) m/z calcd for C18H21BrN3O2: 390.08, found: 389.95 and 391.95 [M+H]$^+$. LCMS conditions: Injection Vol=3 uL; Gradient=2-98% B; Gradient Time=1.5 min; Flow Rate=0.8 ml/min; Wavelength=220 nm; Mobile Phase A=0:100 acetonitrile:water with 0.05% trifluoroacetic acid; Mobile Phase B=100:0 acetonitrile:water with 0.05% trifluoroacetic acid; Column=Waters Aquity BEH C18, 2.1×50 mm, 1.7 U (=μm); Oven Temp=40° C. $^1$H NMR (500 MHz, CDCl$_3$) δ 9.10 (s, 1H), 8.25 (br. s., 1H), 7.94 (d, J=8.8 Hz, 1H), 7.80 (dd, J=8.8, 2.0 Hz, 1H), 7.04 (br. s., 1H), 4.59 (br. s., 2H), 3.66 (t, J=5.7 Hz, 2H), 2.50 (br. s., 2H), 1.55 (s, 9H).

Intermediate: 7-Bromo-2-(1,2,5,6-tetrahydropyridin-3-yl)quinoxaline

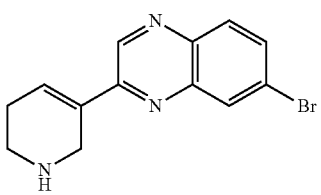 [SMILES: Brc1ccc2ncc(C3=CCCNC3)nc2c1]

Trifluoroacetic acid (0.4 mL, 5.19 mmol) was added to a solution of tert-butyl 3-(7-bromoquinoxalin-2-yl)-5,6-dihydropyridine-1(2H)-carboxylate (50 mg, 0.128 mmol) in dry DCM (2 mL) at rt. The mixture was stirred at rt for 2 h before it was evaporated down to dryness. The residue was free-based using a 1.0 g SCX cartridge (MeOH:2N NH$_3$:MeOH) to yield 7-bromo-2-(1,2,5,6-tetrahydropyridin-3-yl)quinoxaline as a caramel-colored oil which was used 'as is' and carried forward directly. LCMS: t$_R$=0.77 min; LCMS (ESI) m/z calcd for C$_{13}$H13BrN3: 290.03, found: 289.85 and 291.85 [M+H]$^+$. LCMS conditions: Injection Vol=3 uL; Gradient=2-98% B; Gradient Time=1.5 min; Flow Rate=0.8 ml/min; Wavelength=220 nm; Mobile Phase A=0:100 acetonitrile:water with 0.05% trifluoroacetic acid; Mobile Phase B=100:0 acetonitrile:water with 0.05% trifluoroacetic acid; Column=Waters Aquity BEH C18, 2.1×50 mm, 1.7 U; Oven Temp=40° C.

Example 1027: (S)-1-(5-Chloro-2-((5-cyanopyridin-3-yl)methoxy)-4-((2-methyl-3-(3-(1,2,5,6-tetra-hydropyridin-3-yl)quinoxalin-6-yl)benzyl)oxy)benzyl)piperidine-2-carboxylic Acid

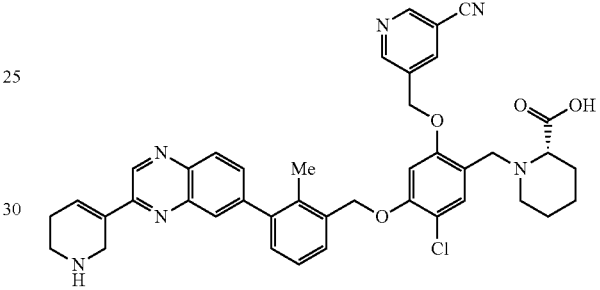

XPhos second generation precatalyst (10.09 mg, 0.013 mmol) was added to a 1 dram vial containing an argon-degassed solution of 7-bromo-2-(1,2,5,6-tetrahydropyridin-3-yl)quinoxaline (37.2 mg, 0.128 mmol), a mixture (1:4) of (S)-1-(5-chloro-2-((5-cyanopyridin-3-yl)methoxy)-4-((2-methyl-3-(4,4,5,5-tetramethyl-1,3,2-dioxaborolan-2-yl)benzyl)oxy)-benzyl)piperidine-2-carboxylic acid and (S)-1-(4-((3-borono-2-methylbenzyl)oxy)-5-chloro-2-((5-cyanopyridin-3-yl)methoxy)benzyl)piperidine-2-carboxylic acid (70.5 mg, 0.128 mmol, based on boronic acid, prepared in a similar fashion as described above) and potassium phosphate (68.0 mg, 0.321 mmol) in THF (1 mL) and water (0.5 mL). The vial was sealed and the mixture was stirred at 80° C. for 16 h. Upon cooling to rt, the organic layer was separated and concentrated to near dryness and the resultant residue was taken up in MeOH (1 mL) and DMF (1 mL) and purified via preparative LCMS with the following conditions: Column: XBridge C18, 19×200 mm, 5 U; Mobile Phase A: 5:95 acetonitrile:water with 10 mM ammonium acetate; Mobile Phase B: 95:5 acetonitrile:water with 10 mM ammonium acetate; Gradient: 14-54% B over 19 min, then a 4 min hold at 100% B; Flow: 20 mL/min. Fractions containing the desired product were combined and dried via centrifugal evaporation. The yield of the product was 25.4 mg (27%), and its estimated purity by LCMS analysis was 97%. Analytical LCMS was used to determine the final purity. Injection 1 conditions: Column: Waters XBridge C18, 2.1×50 mm, 1.7 U; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.75 min hold at 100% B; Flow: 1 mL/min; Detection: MS and UV (220 nm). Injection 1 results: Purity: 98.3%; Observed Mass: 714.97; Retention Time: 1.44 min. Injection 2 conditions: Column: Waters XBridge C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75 min hold at 100% B; Flow: 1 mL/min; Detection: MS and UV (220 nm). Injection 2 results: Purity: 96.7%; Observed Mass: 714.98; Retention Time: 1.46 min. $^1$H NMR (500 MHz, DMSO-$d_6$) δ 9.34 (s, 1H), 9.02 (d, J=1.8 Hz, 1H), 9.01 (d, J=1.8 Hz, 1H), 8.47 (s, 1H), 8.12 (d, J=8.4 Hz, 1H), 7.88 (d, J=1.8 Hz, 1H), 7.76 (dd, J=8.4, 1.8 Hz, 1H), 7.59 (dd, J=6.2, 2.6 Hz, 1H), 7.46 (s, 1H), 7.40-7.34 (m, 2H), 7.24 (br s, 1H), 7.12 (s, 1H), 5.34 (s, 2H), 5.31 (s, 2H), 3.87 (br s, 2H), 3.81 (br d, J=13.6 Hz, 1H), 3.61 (br d, J=13.6 Hz, 1H), 3.13-3.07 (m, 1H), 2.98-2.83 (2 m, 3H), 2.37 (br s, 2H), 2.30 (s, 3H), 2.29-2.24 (m, 1H), 1.83-1.78 (m, 1H), 1.75-1.68 (m, 1H), 1.55-1.45 (m, 3H), 1.41-1.30 (m, 1H).

Intermediate: tert-Butyl 3-(7-Bromoquinoxalin-2-yl)-8-azabicyclo[3.2.1]oct-2-ene-8-carboxylate

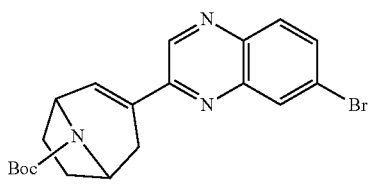 [SMILES: CC(C)(C)OC(=O)N1C2C=C(c3cnc4ccc(Br)cc4n3)CC1CC2]

XPhos second generation precatalyst (11.76 mg, 0.015 mmol) was added to a thick-walled, screw top tube containing an argon-degassed solution of 7-bromo-2-chloroquinoxaline (72.6 mg, 0.298 mmol), tert-butyl 3-(4,4,5,5-tetramethyl-1,3,2-dioxaborolan-2-yl)-8-azabicyclo[3.2.1]oct-2-ene-8-carboxylate (100 mg, 0.298 mmol) and potassium phosphate (158 mg, 0.746 mmol) in THF (2 mL) and water (1.0 mL). The tube was sealed, and the mixture was stirred at rt for 16 h before it was diluted with ethyl acetate and water. The aqueous layer was separated and the aqueous layer was extracted twice more with ethyl acetate. The combined organic extract was washed with brine, dried over MgSO$_4$, filtered and concentrated to give a caramel-colored residue. Three quarters of this residue was taken up in a small amount of dichloromethane and charged to a RediSepRf normal phase silica gel Teledyne ISCO 24 g disposable column which was first eluted with hexanes for 80 mL, followed by 0-50% B for 280 mL where solvent B=ethyl acetate and solvent A=hexanes. After concentration of the eluant, there was isolated the desired product, tert-butyl 3-(7-bromoquinoxalin-2-yl)-8-azabicyclo-[3.2.1]oct-2-ene-8-carboxylate (21.2 mg, 17% yield) as a light yellow film. The remaining one quarter of the crude residue was submitted for preparative LCMS purification for characterization purposes with the following conditions: Column: XBridge C18, 19×200 mm, 5 U; Mobile Phase A: 5:95 acetonitrile:water with 10 mM ammonium acetate; Mobile Phase B: 95:5 acetonitrile:water with 10 mM ammonium acetate; Gradient: 50-100% B over 22 min, then a 5 min hold at 100% B; Flow: 20 mL/min. Fractions containing the desired product were combined and dried via centrifugal evaporation. The yield of the product was 6.2 mg (5%), and its estimated purity by LCMS analysis was 100%. Analytical LCMS was used to determine the final purity. Injection 1 conditions: Column: Waters XBridge C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75 min hold at 100% B; Flow: 1 mL/min; Detection: MS and UV (220 nm). Injection 1 results: Purity: 100.0%; Observed Mass: 416.06; Retention Time: 2.5 min. Injection 2 conditions: Column: Waters XBridge C18, 2.1×50 mm, 1.7 U; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.75 min hold at 100% B; Flow: 1 mL/min; Detection: MS and UV (220 nm). Injection 2 results: Purity: 100.0%; Observed Mass: 416.07; Retention Time: 2.51 min. $^1$H NMR (500 MHz, DMSO-$d_6$) δ9.32 (s, 1H), 8.24 (d, J=2.2 Hz, 1H), 8.04-7.99 (m, 1H), 7.93 (dd, J=8.8, 1.8 Hz, 1H), 7.49 (br. s., 1H), 4.54 (br. s., 1H), 4.49-4.37 (m, 1H), 3.13-2.98 (m, 1H), 2.65-2.54 (m, 1H), 2.28-2.09 (m, 1H), 1.98 (br. s., 2H), 1.77-1.64 (m, 1H), 1.39 (s, 9H).

The preparation in a two mmol scale and purification using normal phase silica gel Teledyne ISCO column were performed in a similar fashion: LCMS: $t_R$=1.55 min; LCMS (ESI) m/z calcd for C20H23BrN3O2: 416.10, found: 415.95 and 417.95 [M+H]$^+$. LCMS conditions: Injection Vol=3 uL; Gradient=2-98% B; Gradient Time=1.5 min; Flow Rate=0.8 ml/min; Wavelength=220 nm; Mobile Phase A=0:100 acetonitrile:water with 0.05% trifluoroacetic acid; Mobile Phase B=100:0 acetonitrile:water with 0.05% trifluoroacetic acid; Column=Waters Aquity BEH C18, 2.1×50 mm, 1.7 U; Oven Temp=40° C.

Example 1028: (2S)-1-(4-((3-(3-(8-(tert-Butoxycarbonyl)bicyclo[3.2.1]oct-2-en-3-yl)quinoxalin-6-yl)-2-methylbenzyl)oxy)-5-chloro-2-((5-cyanopyridin-3-yl)methoxy)benzyl)piperidine-2-carboxylic Acid

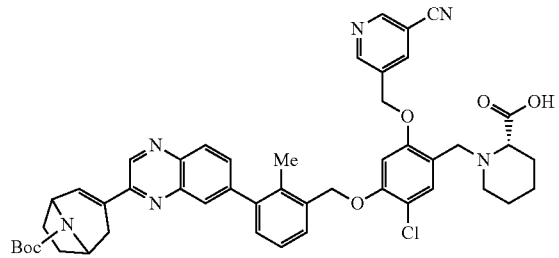 [SMILES: Cc1c(COc2cc(OCc3cncc(C#N)c3)c(CN3CCCC[C@H]3C(=O)O)cc2Cl)cccc1-c1ccc2ncc(C3=CC4CCC(C3)N4C(=O)OC(C)(C)C)nc2c1]

Example 1028 was prepared in a similar fashion to Example 1027. The crude material was purified via preparative LCMS with the following conditions: Column: XBridge C18, 19×200 mm, 5 U; Mobile Phase A: 5:95 acetonitrile:water with 10 mM ammonium acetate; Mobile Phase B: 95:5 acetonitrile:water with 10 mM ammonium acetate; Gradient: 20-85% B over 25 min, then a 5 min hold at 100% B; Flow: 20 mL/min. Fractions containing the desired product were combined and dried via centrifugal evaporation. The yield of the product was 2.5 mg (3.2%), and its estimated purity by LCMS analysis was 97%. Analytical LCMS was used to determine the final purity. Injection 1 conditions: Column: Waters XBridge C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75 min hold at 100% B; Flow: 1 mL/min; Detection: MS and UV (220 nm). Injection 1 results: Purity: 100.0%; Observed Mass: 841.05; Retention Time: 2.21 min. Injection 2 conditions: Column: Waters XBridge C18, 2.1×50 mm, 1.7 U; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.75 min hold at 100% B; Flow: 1 mL/min; Detection: MS and UV (220 nm). Injection 2 results: Purity: 96.6%; Observed Mass: 841.06; Retention Time: 2.26 min. $^1$H NMR (500 MHz, DMSO-$d_6$) δ 9.32 (s, 1H), 9.04-9.03 (m, 1H), 9.02-9.00 (m, 1H), 8.48 (s, 1H), 8.13 (d, J=8.4 Hz, 1H), 7.90 (s, 1H), 7.77 (dd, J=8.4, 1.8 Hz, 1H), 7.59 (dd, J=5.9, 2.9 Hz, 1H), 7.48 (br s, 1H), 7.45 (s, 1H), 7.39-7.36 (m, 2H), 5.36 (br s, 2H), 5.32 (s, 2H), 4.55 (br s, 1H), 4.50-4.38 (m, 1H), 3.80 (br d, J=13.9 Hz, 1H), 3.63 (br d, J=13.2 Hz, 1H), 3.19-3.02 (2 m, 2H), 2.95-2.83 (m, 1H), 2.74-2.59 (m, 1H), 2.31 (s, 3H), 2.31-2.26 (m, 1H), 2.26-2.08 (m, 1H), 2.03-1.96 (m, 2H), 1.86-1.77 (m, 1H), 1.76-1.65 (m, 2H), 1.49 (br s, 3H), 1.42-1.34 (m, 2H), 1.39 (s, 9H).

Intermediate: 2-(8-Azabicyclo[3.2.1]oct-2-en-3-yl)-7-bromoquinoxaline

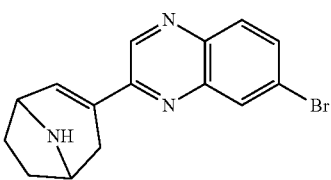 [SMILES: Brc1ccc2ncc(C3=CC4CCC(C3)N4)nc2c1]

Trifluoroacetic acid (200 µL, 2.60 mmol) was added in one portion to a solution of tert-butyl 3-(7-bromoquinoxalin-2-yl)-8-azabicyclo[3.2.1]oct-2-ene-8-carboxylate (50 mg, 0.12 mmol) in dry dichloromethane (1 mL) at rt. The mixture was stirred at rt for 1.5 h before it was concentrated with nitrogen stream and placed on high vacuum for 16 h. The resultant residue was free-based using a 1 g Varian Mega Bond Elut Flash SCX cartridge (MeOH and then 2 M NH$_3$ in MeOH; 3 column volume each). Afterwards, there was isolated the desired product, 2-(8-azabicyclo[3.2.1]oct-2-en-3-yl)-7-bromoquinoxaline (35.7 mg, 94% yield) as a light caramel-colored glass which was carried forward directly. LCMS: $t_R$=1.06 min; LCMS (ESI) m/z calcd for C15H15BrN3: 316.05, found: 316.15 and 318.15 [M+H]$^+$. LCMS conditions: Injection Vol=1 uL; Gradient=0-100% B; Gradient Time=2 min; Flow Rate=1 ml/min; Wavelength=220 nm; Mobile Phase A=10:90 acetonitrile:water with 0.1% trifluoroacetic acid; Mobile Phase B=90:10 acetonitrile:water with 0.1% trifluoroacetic acid; Column=Waters Aquity BEH C18, 2.1×50 mm, 1.7 U; Oven Temp=40° C.

Example 1029: (2S)-1-(4-((3-(3-(8-Azabicyclo [3.2.1]oct-2-en-3-yl)quinoxalin-6-yl)-2-methylbenzyl)-oxy)-5-chloro-2-((5-cyanopyridin-3-yl) methoxy)benzyl)piperidine-2-carboxylic acid

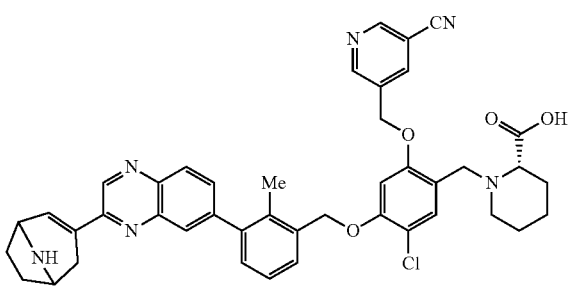 [SMILES: Cc1c(COc2cc(OCc3cncc(C#N)c3)c(CN3CCCC[C@H]3C(=O)O)cc2Cl)cccc1-c1ccc2ncc(C3=CC4CCC(C3)N4)nc2c1]

Example 1029 was prepared in a similar fashion to Example 1027. The crude material was purified via preparative LCMS with the following conditions: Column: XBridge C18, 19×200 mm, 5 U; Mobile Phase A: 5:95 acetonitrile:water with 10 mM ammonium acetate; Mobile Phase B: 95:5 acetonitrile:water with 10 mM ammonium acetate; Gradient: 12-52% B over 22 min, then a 4 min hold at 100% B; Flow: 20 mL/min. Fractions containing the desired product were combined and dried via centrifugal evaporation. The yield of the product was 20.8 mg (25%), and its estimated purity by LCMS analysis was 97%. Analytical LCMS was used to determine the final purity. Injection 1 conditions: Column: Waters XBridge C18, 2.1×50 mm, 1.7 U; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.75 min hold at 100% B; Flow: 1 mL/min; Detection: MS and UV (220 nm). Injection 1 results: Purity: 97.3%; Observed Mass: 741.02; Retention Time: 1.43 min. Injection 2 conditions: Column: Waters XBridge C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75 min hold at 100% B; Flow: 1 mL/min; Detection: MS and UV (220 nm). Injection 2 results: Purity: 97.3%; Observed Mass: 741.05; Retention Time: 1.41 min. $^1$H NMR (500 MHz, DMSO-$d_6$) δ 9.28 (s, 1H), 9.02 (d, J=1.8 Hz, 1H), 9.01 (d, J=1.5 Hz, 1H), 8.47 (s, 1H), 8.11 (d, J=8.4 Hz, 1H), 7.87 (s, 1H), 7.75 (dd, J=8.6, 1.7 Hz, 1H), 7.58 (dd, J=6.2, 1.8 Hz, 1H), 7.45 (s, 1H), 7.41 (br d, J=5.5 Hz, 1H), 7.39-7.35 (m, 2H), 7.12 (d, J=3.3 Hz, 1H), 5.34 (br s, 2H), 5.31 (s, 2H), 3.94-3.90 (m, 1H), 3.89-3.85 (m, 1H), 3.80 (br d, J=14.3 Hz, 1H), 3.61 (br d, J=13.6 Hz, 1H), 3.13-3.05 (m, 1H), 2.99-2.96 (m, 1H), 2.95-2.92 (m, 1H), 2.92-2.86 (m, 1H), 2.30 (s, 3H), 2.33-2.22 (m, 1H), 2.06-1.95 (m, 2H), 1.90-1.85 (m, 1H), 1.82-1.75 (m, 1H), 1.75-1.66 (m, 1H), 1.65-1.56 (m, 1H), 1.55-1.43 (m, 3H), 1.41-1.29 (m, 1H).

Example 1030: (S)-1-(5-chloro-2-((5-cyanopyridin-3-yl)methoxy)-4-((2-methyl-3-(3-(1,2,3,6-tetrahydropyridin-4-yl)quinoxalin-6-yl)benzyl)oxy)benzyl)piperidine-2-carboxylic Acid Example 1031: (S)-1-(5-chloro-2-((5-cyanopyridin-3-yl)methoxy)-4-((2-methyl-3-(3-(4-methylpiperazin-1-yl)quinoxalin-6-yl)benzyl)oxy)benzyl)piperidine-2-carboxylic Acid

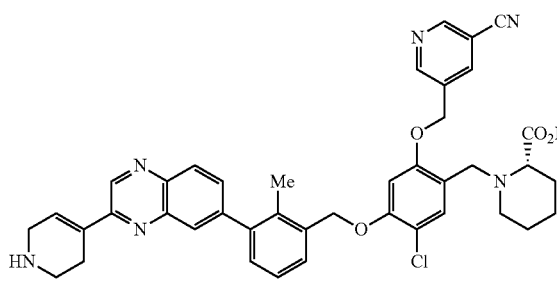

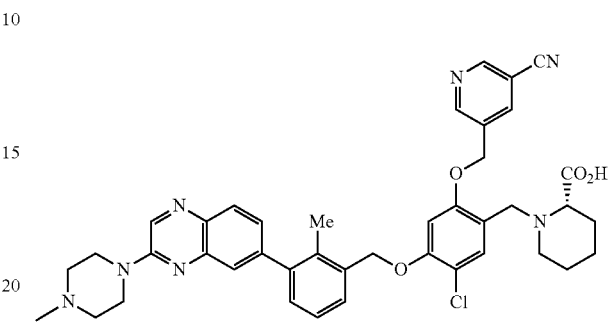

Example 1030 was prepared in a similar fashion to Example 1027. The crude material was purified via preparative LC/MS using the following conditions: Waters XBridge 5 μm C18, 19×200 mm where mobile phase A was 5:95 acetonitrile:water with 0.1% trifluoroacetic acid and mobile phase B was 95:5 acetonitrile:water with 0.1% trifluoroacetic acid at a gradient of 15-55% B over 20 minutes with a 5-minute hold at a flow rate of 20 mL/minute. Fractions containing the desired product were combined and dried via centrifugal evaporation. The yield of the product was 7.3 mg (9% yield), and its estimated purity by LCMS analysis was 94%. Two analytical LC/MS injections were used to determine the final purity. Injection 1 conditions: Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm. Injection 2 conditions: Waters Acquity UPLC BEH 1.7 μm C18, 2.1×50 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 3 minutes with a 0.75-minute hold at 100% B at a flow rate of 1.0 mL/minute at a UV wavelength of 220 nm. Analysis condition 1: Retention time=1.328 min; ESI-MS(+) m/z=715.0 (M+H) Analysis condition 2: Retention time=1.298 min; ESI-MS(+) m/z=715.0 (M+H) $^1$H NMR (500 MHz, DMSO-$d_6$) δ9.36 (s, 1H), 9.06-8.95 (m, 1H), 8.42 (s, 1H), 8.16 (d, J=8.5 Hz, 1H), 7.92 (d, J=1.5 Hz, 1H), 7.79 (dd, J=8.4, 2.0 Hz, 1H), 7.58-7.50 (m, 2H), 7.41-7.33 (m, 2H), 7.28 (s, 1H), 7.17 (d, J=7.0 Hz, 2H), 7.09 (m, 2H), 5.38 (d, J=6.4 Hz, 2H), 5.34 (s, 2H), 4.25 (m, 1H), 3.92 (m, 1H), 3.40 (m, 2H), 3.33 (m, 1H), 3.26 (m, 2H), 2.94 (m, 2H), 2.89-2.81 (m, 1H), 2.32-2.24 (m, 4H), 2.08 (m, 1H), 1.65 (m, 4H), 1.47 (m, 1H).

Example 1031 was prepared from 7-bromo-2-(4-methylpiperazin-1-yl)quinoxaline in a similar fashion to Example 1027. The crude material was purified via preparative LC/MS using the following conditions: Waters XBridge 5 μm C18, 19×200 mm where mobile phase A was 5:95 acetonitrile:water with 0.1% TFA and mobile phase B was 95:5 acetonitrile:water with 0.1% TFA at a gradient of 15-55% B over 20 minutes with a 5-minute hold at a flow rate of 20 mL/minute. Fractions containing the desired product were combined and dried via centrifugal evaporation. The yield of the product was 6.1 mg (6% yield), and its estimated purity by LCMS analysis was 93%. Two analytical LC/MS injections were used to determine the final purity. Injection 1 conditions: Waters Acquity UPLC BEH 1.7 μm C18, 2.1×50 mm where mobile phase A was 5:95 acetonitrile:water with 10 mM ammonium acetate; mobile phase B was 95:5 acetonitrile:water with 10 mM ammonium acetate at a temperature of 50° C. at a gradient of 0-100% B over 3 minutes with a 0.75-minute hold at 100% B at a flow rate of 1.0 mL/minute at a UV wavelength of 220 nm. Injection 2 conditions: Waters Acquity UPLC BEH 1.7 μm C18, 2.1×50 mm where mobile phase A was 5:95 acetonitrile:water with 0.1% trifluoroacetic acid; mobile phase B was 95:5 acetonitrile:water with 0.1% trifluoroacetic acid at a temperature of 50° C. at a gradient of 0-100% B over 3 minutes with a 0.75-minute hold at 100% B at a flow rate of 1.0 mL/minute at a UV wavelength of 220 nm.

Analysis condition 1: Retention time=1.387 min; ESI-MS (+) m/z=732.1 (M+H)

Analysis condition 2: Retention time=1.434 min; ESI-MS (+) m/z=732.1 (M+H)

$^1$H NMR (500 MHz, DMSO-$d_6$) δ9.02 (m, 2H), 8.93 (s, 1H), 8.46 (s, 1H), 7.96 (d, J=8.2 Hz, 1H), 7.58-7.52 (m, 3H), 7.43 (m, 1H), 7.33 (m, 2H), 7.27 (br. s., 1H), 7.21 (s, 1H), 7.16 (br. s., 1H), 7.06 (br.s., 1H), 5.39 (d, J=7.3 Hz, 2H), 5.35 (s, 2H), 4.82-4.61 (m, 1H), 4.28 (m, 3H), 4.04-3.86 (m, 2H), 3.34-3.24 (m, 5H), 2.86 (m, 5H), 2.28 (s, 3H), 2.18-2.05 (m, 2H), 1.67 (m, 3H), 1.49 (m, 1H).

Examples 2001-2018 were prepared in a manner exemplified by Example 2001 and analogous to those described above.

Example 2001: 5-((4-chloro-2-4(1,3-dihydroxypropan-2-yl)(methyl)amino)methyl)-5-((2-methyl-3-(2-((1S,4S)-5-methyl-2,5-diazabicyclo[2.2.1]heptan-2-yl)benzo[d]oxazol-5 yl)benzyl)oxy)phenoxy)methyl) nicotinonitrile

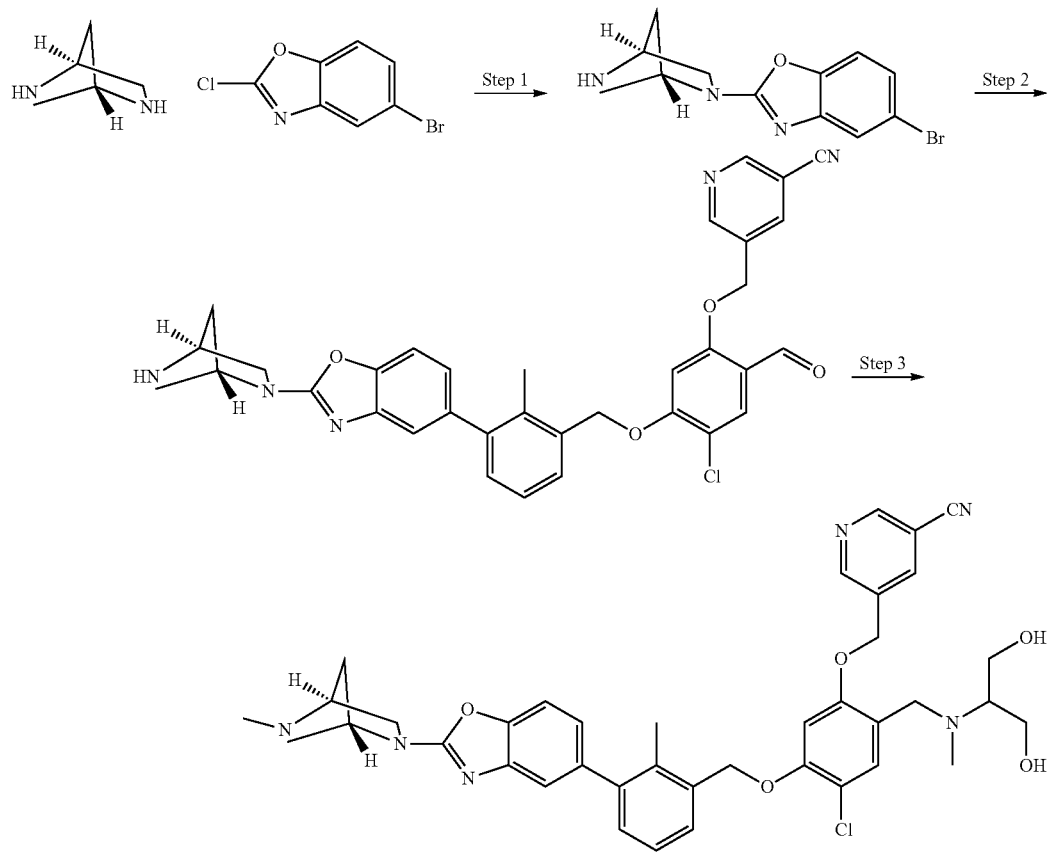

Example 2001

Step 1: To a mixture of (1S,4S)-2,5-diazabicyclo[2.2.1]heptane dihydrobromide (300 mg, 1.154 mmol), 5-bromo-2-chlorobenzo[d]oxazole (179 mg, 0.769 mmol) in DMF (4 mL) was added Hunig's Base (0.403 mL, 2.308 mmol). The reaction solution was stirred for 2 h. and diluted with ethyl acetate, washed with brine, concentrated after drying with $MgSO_4$. The residue was purified by flash column chromatography over silical gel eluting with 10-30% MeOH in DCM to give 60 mg of 2-((1S,4S)-2,5-diazabicyclo[2.2.1]heptan-2-yl)-5-bromobenzo[d]oxazole as a solid. LC/MS (ESI) m/z 295.8 (M+1)$^+$.

Step 2: A mixture of 5-((4-chloro-2-formyl-5-((2-methyl-3-(4,4,5,5-tetramethyl-1,3,2-dioxaborolan-2-yl)benzyl)oxy)phenoxy)methyl)nicotinonitrile (0.088 g, 0.17 mmol), 2-((1S,4S)-2,5-diazabicyclo[2.2.1]heptan-2-yl)-5-bromobenzo[d]oxazole (0.050 g, 0.170 mmol), and 0.5 M $K_3PO_4$ (1.020 mL, 0.510 mmol) in THF (6 mL) and 1,4-dioxane (1.200 mL) was stirred under $N_2$, sparging for 15 min, then treated with 2nd generation XPhos precatalyst (6.69 mg, 8.50 μmop. The mixture was sparged for 10 min, then stirred under nitrogen for 16 hours. The mixture was diluted with EtOAc, washed with water, brine, dried ($MgSO_4$) and concentrated. The crude isolate was purified by flash chromatography over silica gel to give 80 mg of the desired product 5-((5-((3-(2-((1S,4S)-2,5-diazabicyclo[2.2.1]heptan-2-yl)benzo[d]oxazol-5-yl)-2-methylbenzyl)oxy)-4-chloro-2-formylphenoxy)methyl)nicotinonitrile as solid. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100%; Observed Mass: 606.1; Retention Time: 1.86 min.

Step 3: A mixture of 5-((5-((3-(2-((1S,4S)-2,5-diazabicyclo[2.2.1]heptan-2-yl)benzo[d]oxazol-5-yl)-2-methylbenzyl)oxy)-4-chloro-2-formylphenoxy)methyl)nicotinonitrile (18.18 mg, 0.03 mmol), 2-aminopropane-1,3-diol (10.93 mg, 0.120 mmol), and acetic acid (0.012 mL, 0.210 mmol) in DCE (2 mL) and EtOH (2 mL) and sodium cyanoborohydride (1M in THF) (0.120 mL, 0.120 mmol) was stirred for 16 h at rt. To the reaction mixture was added 0.02 mL of 37% formaldehyde solution in water, then stirred for 16 h.

After solvents were removed, the crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min. Fractions containing the desired product were combined and dried via centrifugal evaporation. The yield of the product was 7.0 mg, and its estimated purity by LCMS analysis was 89%. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 89.1%; Observed Mass: 709.09; Retention Time: 1.64 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 90.3%; Observed Mass: 709.12; Retention Time: 1.32 min.

Example 2002: (S)-1-(5-chloro-2-((5-cyanopyridin-3-yl)methoxy)-4-((2-methyl-3-(2-((1S,4S)-5-methyl-2,5-diazabicyclo[2.2.1]heptan-2-yl)benzo[d]oxazol-5-yl)benzyl)oxy)benzyl)piperidine-2-carboxylic Acid B over 3 min, then a 0.75 min hold at 100% B; Flow: 1 mL/min; Detection: MS and UV (220 nm). Injection 1 results: Purity: 100.0%; Observed Mass: 733.05; Retention Time: 1.51 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 97.0%; Observed Mass: 733.1; Retention Time: 1.38 min.

Example 2003: 5-((5-((3-(2-((1S,4S)-2,5-diazabicyclo[2.2.1]heptan-2-yl)benzo[d]oxazol-5-yl)-2-methylbenzyl)oxy)-4-chloro-2-4(1,3-dihydroxypropan-2-yl)amino)methyl)phenoxy)methyl)nicotinonitrile

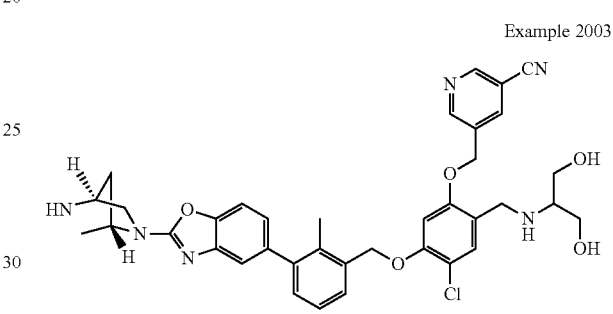

Example 2003

The crude material was purified via preparative LC/MS with the following conditions: Column: XBridge C18,

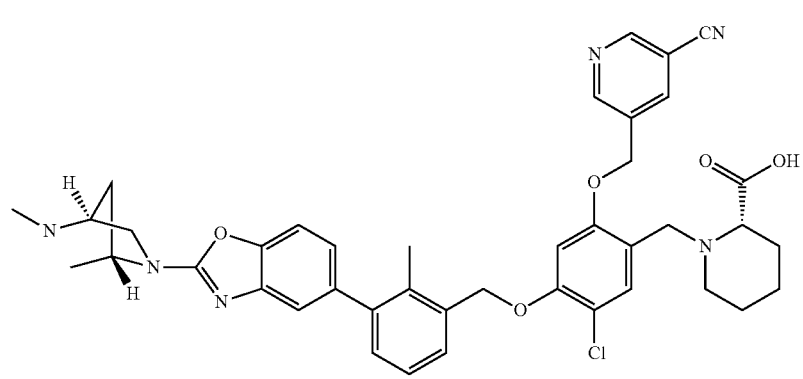

Example 2002

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile: water with 10-mM ammonium acetate; Gradient: 15-55% B over 20 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100%

19×200 mm, 5-μm particles; Mobile Phase A: 5:95 acetonitrile:water with 10-mM ammonium acetate; Mobile Phase B: 95:5 acetonitrile: water with 10-mM ammonium acetate; Gradient: 15-55% B over 20 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 99.2%; Observed Mass: 681; Retention Time: 1.3 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 681.06; Retention Time: 1.43 min.

Example 2004: 5-((4-chloro-2-4(1,3-dihydroxy-2-methylpropan-2-yl)(methyl)amino)methyl)-5-((2-methyl-3-(2-((1S,4S)-5-methyl-2,5-diazabicyclo[2.2.1]heptan-2-yl)benzo[d]oxazol-5-yl)benzyl)oxy)phenoxy)methyl)nicotinonitrile

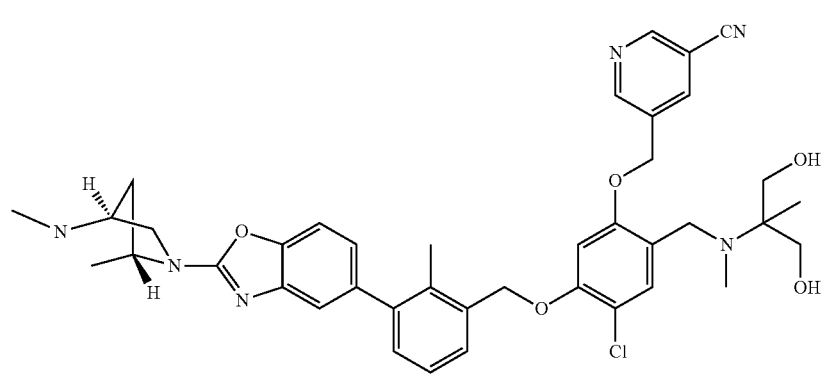

Example 2004

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile: water with 10-mM ammonium acetate; Gradient: 20-60% B over 20 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 95.0%; Observed Mass: 723.08; Retention Time: 1.63 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 94.6%; Observed Mass: 723.12; Retention Time: 1.35 min.

Example 2005: (S)-1-(4-((3-(2-((1S,4S)-2,5-diazabicyclo[2.2.1]heptan-2-yl)benzo[d]oxazol-5-yl)-2-methylbenzyl)oxy)-5-chloro-2-((5-cyanopyridin-3-yl)methoxy)benzyl)piperidine-2-carboxylic Acid

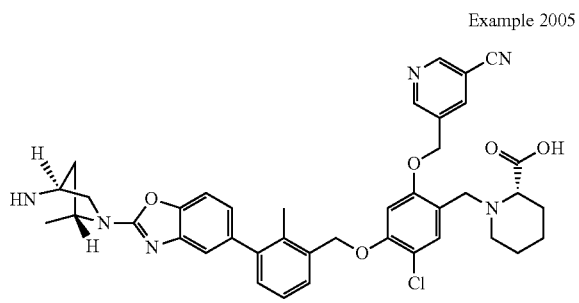

Example 2005

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile: water with 10-mM ammonium acetate; Gradient: 10-50% B over 20 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid;

Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 96.6%; Observed Mass: 719.02; Retention Time: 1.38 min. Injection 2 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 719; Retention Time: 1.39 min.

Example 2006: 5-((5-((3-(2-((1S,4S)-2,5-diazabicyclo[2.2.1]heptan-2-yl)benzo[d]oxazol-5-yl)-2-methylbenzyl)oxy)-4-chloro-2-4(1,3-dihydroxy-2-methylpropan-2-yl)amino)methyl)phenoxy)methyl) nicotinonitrile

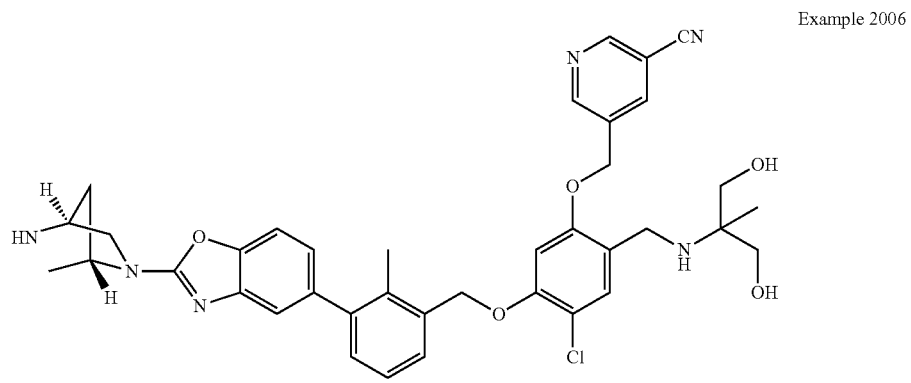

Example 2006

The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile: water with 10-mM ammonium acetate; Gradient: 15-55% B over 20 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-50% B over 20 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-µm particles; Mobile Phase A: 5:95 methanol: water with 10-mM ammonium acetate; Mobile Phase B: 95:5 methanol: water with 10-mM ammonium acetate; Gradient: 45-85% B over 20 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 695.1; Retention Time: 1.33 min. Injection 2 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 695.05; Retention Time: 1.43 min.

Example 2007: (S)-1-(5-chloro-2-((5-cyanopyridin-3-yl)methoxy)-4-((2-methyl-3-(2-(4-methylpiperazin-1-yl)benzo[d]oxazol-5-yl)benzyl)oxy)benzyl)piperidine-2-carboxylic Acid

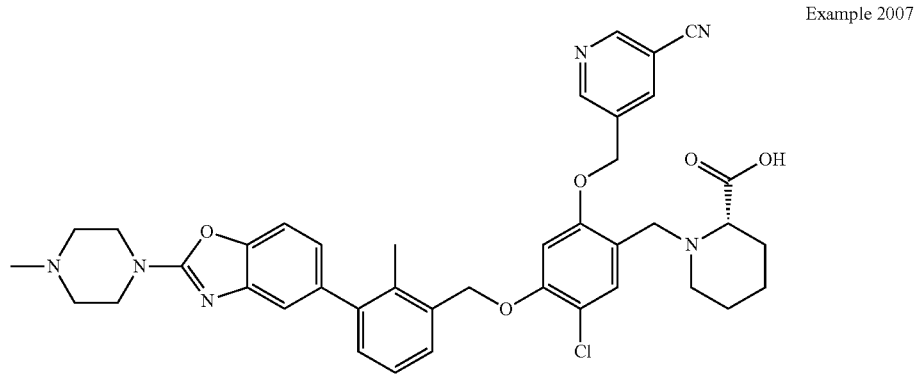 [SMILES: Cc1c(COc2cc(OCc3cncc(C#N)c3)c(CN3CCCC[C@H]3C(=O)O)cc2Cl)cccc1-c1ccc2oc(N3CCN(C)CC3)nc2c1]

Example 2007

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 22-62% B over 23 minutes, then a 4-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 721.04; Retention Time: 1.9 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 721.02; Retention Time: 1.47 min.

Example 2008: 5-((4-chloro-2-4(1,3-dihydroxypropan-2-yl)amino)methyl)-5-((2-methyl-3-(2-(4-methylpiperazin-1-yl)benzo[d]oxazol-5-yl)benzyl)oxy)phenoxy)methyl)nicotinonitrile

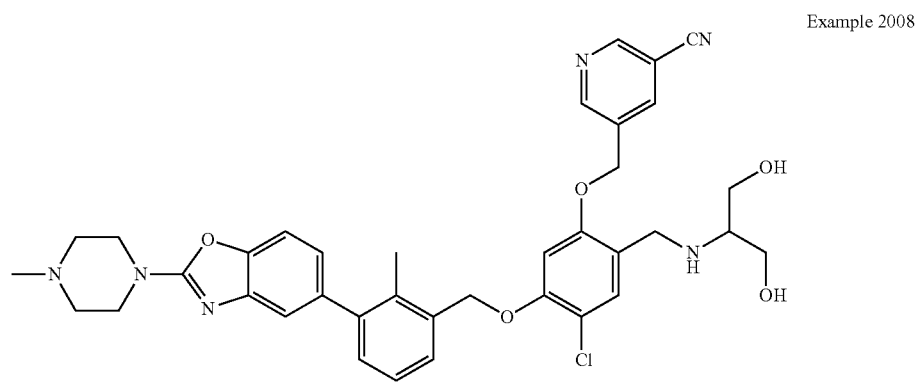 [SMILES: Cc1c(COc2cc(OCc3cncc(C#N)c3)c(CNC(CO)CO)cc2Cl)cccc1-c1ccc2oc(N3CCN(C)CC3)nc2c1]

Example 2008

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile: water with 10-mM ammonium acetate; Gradient: 26-66% B over 25 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 98.9%; Observed Mass: 683.01; Retention Time: 1.95 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 99.2%; Observed Mass: 682.99; Retention Time: 1.4 min.

Example 2009: 5-((4-chloro-2-4(1,3-dihydroxy-2-methylpropan-2-yl)amino)methyl)-5-((2-methyl-3-(2-(4-methylpiperazin-1-yl)benzo[d]oxazol-5-yl)benzyl)oxy)phenoxy)methyl)nicotinonitrile

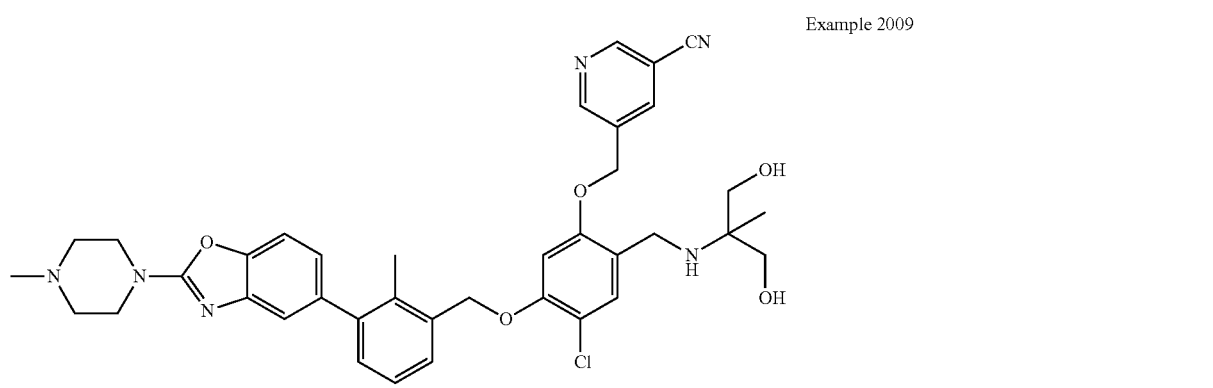

Example 2009

The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile: water with 0.1% trifluoroacetic acid; Gradient: 10-50% B over 25 minutes, then a 4-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 98.2%; Observed Mass: 697.03; Retention Time: 1.95 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 97.8%; Observed Mass: 697.02; Retention Time: 1.44 min.

Example 2010: (5-chloro-2-((5-cyanopyridin-3-yl)methoxy)-4-((2-methyl-3-(2-(4-methylpiperazin-1-yl)benzo[d]oxazol-5-yl)benzyl)oxy)benzyl)-L-serine

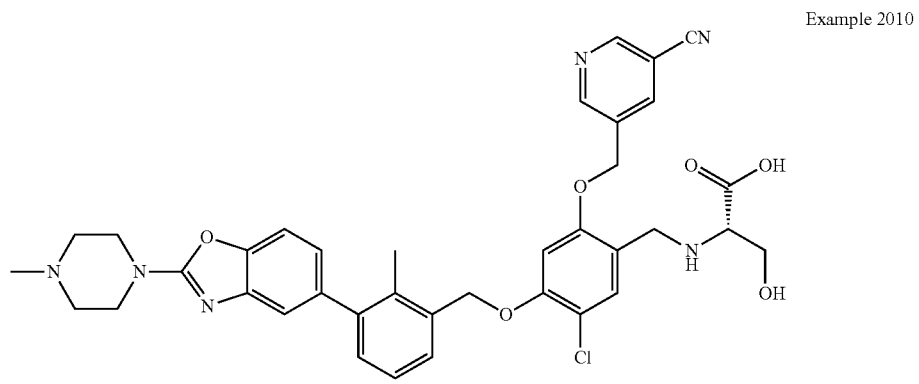 [SMILES: Cc1c(COc2cc(OCc3cncc(C#N)c3)c(CN[C@@H](CO)C(=O)O)cc2Cl)cccc1-c1ccc2oc(N3CCN(C)CC3)nc2c1]

Example 2010

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile: water with 10-mM ammonium acetate; Gradient: 15-55% B over 22 minutes, then a 4-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 93.0%; Observed Mass: 696.93; Retention Time: 1.8 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 93.6%; Observed Mass: 696.98; Retention Time: 1.41 min.

Example 2011: (S)-2-((5-chloro-2-((5-cyanopyridin-3-yl)methoxy)-4-((2-methyl-3-(2-(4-methylpiperazin-1-yl)benzo[d]oxazol-5-yl)benzyl)oxy)benzyl)amino)-3-hydroxy-2-methylpropanoic Acid

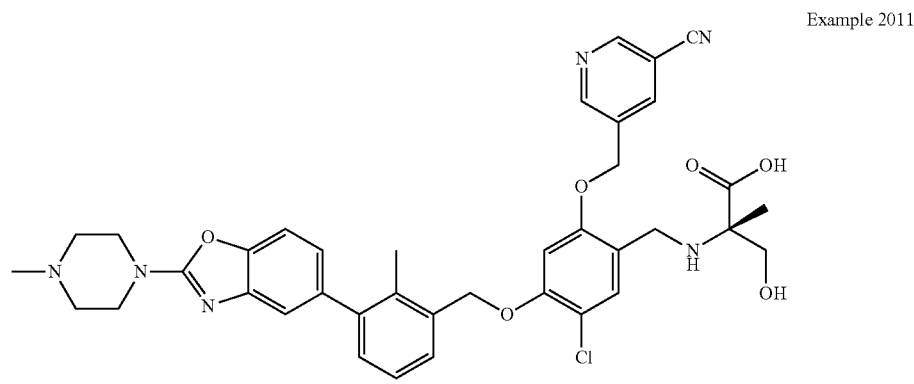 [SMILES: Cc1c(COc2cc(OCc3cncc(C#N)c3)c(CN[C@@](C)(CO)C(=O)O)cc2Cl)cccc1-c1ccc2oc(N3CCN(C)CC3)nc2c1]

Example 2011

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile: water with 10-mM ammonium acetate; Gradient: 20-60% B over 20 minutes, then a 4-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 98.6%; Observed Mass: 710.97; Retention Time: 1.84 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.8%; Observed Mass: 710.98; Retention Time: 1.44 min.

Example 2012: (S)-2-((5-chloro-2-((5-cyanopyridin-3-yl)methoxy)-4-((2-methyl-3-(2-(4-methylpiperazin-1-yl)benzo[d]oxazol-5-yl)benzyl)oxy)benzyl)amino)pentanoic Acid

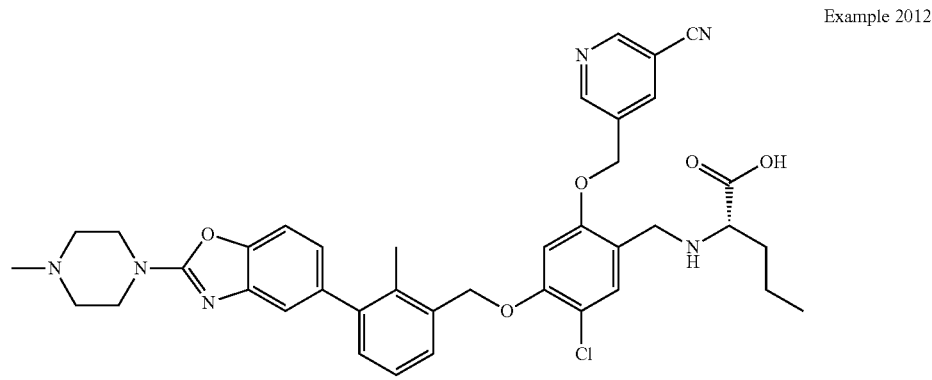

Example 2012

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile: water with 10-mM ammonium acetate; Gradient: 22-62% B over 22 minutes, then a 4-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 709.05; Retention Time: 1.91 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 709.01; Retention Time: 1.53 min.

Example 2013: (S)-2-((5-chloro-2-((5-cyanopyridin-3-yl)methoxy)-4-((2-methyl-3-(2-(4-methylpiperazin-1-yl)benzo[d]oxazol-5-yl)benzyl)oxy)benzyl)amino)-3-methylbutanoic Acid

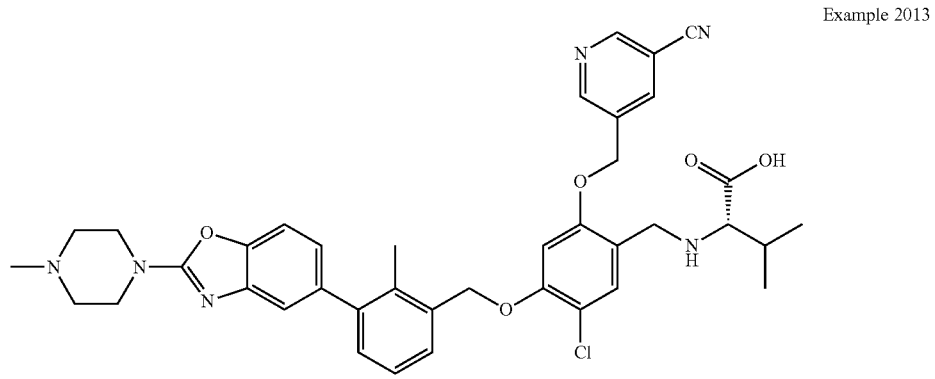 [SMILES: Cc1c(COc2cc(OCc3cncc(C#N)c3)c(CN[C@H](C(=O)O)C(C)C)cc2Cl)cccc1-c1ccc2oc(N3CCN(C)CC3)nc2c1]

Example 2013

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile: water with 10-mM ammonium acetate; Gradient: 22-62% B over 22 minutes, then a 4-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 709.01; Retention Time: 1.9 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 709; Retention Time: 1.5 min.

Example 2014: 5-((4-chloro-2-4(1,3-dihydroxypropan-2-yl)(methyl)amino)methyl)-5-((2-methyl-3-(2-(4-methylpiperazin-1-yl)benzo[d]oxazol-5-yl)benzyl)oxy)phenoxy)methyl)nicotinonitrile

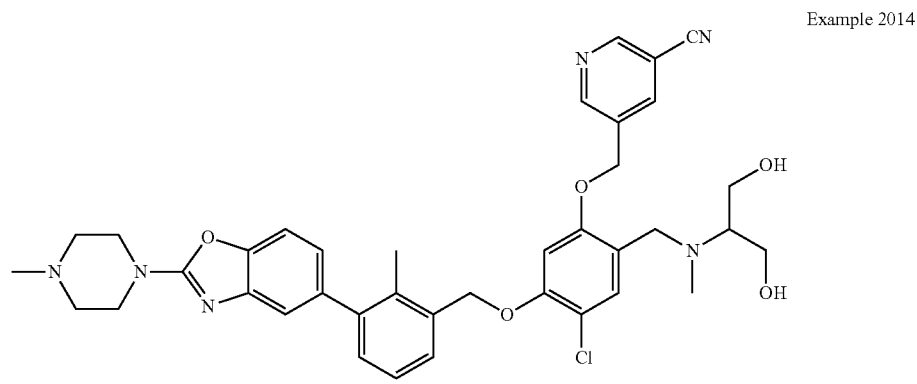 [SMILES: Cc1c(COc2cc(OCc3cncc(C#N)c3)c(CN(C)C(CO)CO)cc2Cl)cccc1-c1ccc2oc(N3CCN(C)CC3)nc2c1]

Example 2014

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile: water with 10-mM ammonium acetate; Gradient: 35-75% B over 20 minutes, then a 4-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm).

Injection 1 results: Purity: 100.0%; Observed Mass: 697.01; Retention Time: 2.11 min.

Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 97.7%; Observed Mass: 696.98; Retention Time: 1.46 min.

Example 2015: 5-((4-chloro-2-4(1,3-dihydroxy-2-methylpropan-2-yl)(methyl)amino)methyl)-5-((2-methyl-3-(2-(4-methylpiperazin-1-yl)benzo[d]oxazol-5-yl)benzyl)oxy)phenoxy)methyl)nicotinonitrile

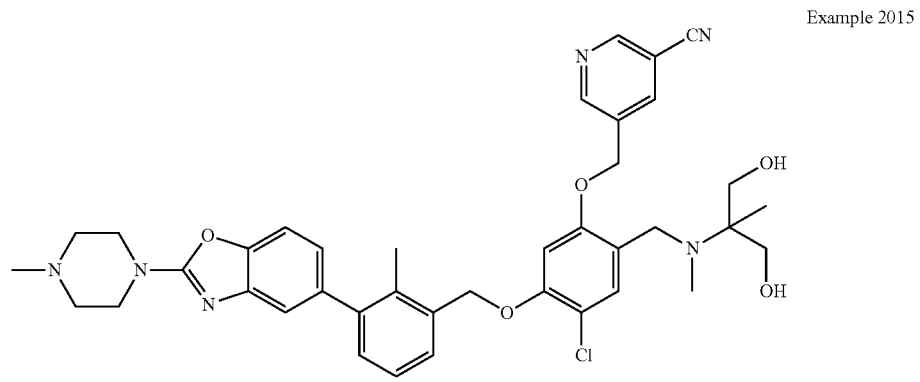 [SMILES: Cc1c(COc2cc(OCc3cncc(C#N)c3)c(CN(C)C(C)(CO)CO)cc2Cl)cccc1-c1ccc2oc(N3CCN(C)CC3)nc2c1]

Example 2015

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile: water with 10-mM ammonium acetate; Gradient: 35-75% B over 19 minutes, then a 4-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 99.2%; Observed Mass: 711.03; Retention Time: 2.04 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 99.4%; Observed Mass: 711.03; Retention Time: 1.49 min.

Example 2016: N-(5-chloro-2-((5-cyanopyridin-3-yl)methoxy)-4-((2-methyl-3-(2-(4-methylpiperazin-1-yl)benzo[d]oxazol-5-yl)benzyl)oxy)benzyl)-N-methyl-L-serine

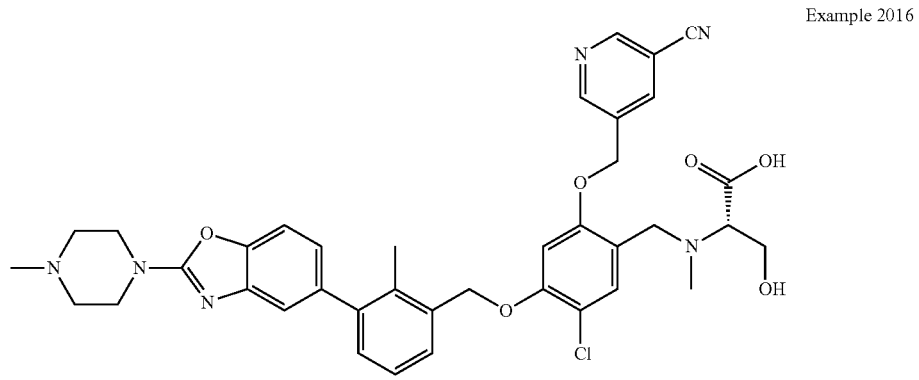 [SMILES: Cc1c(COc2cc(OCc3cncc(C#N)c3)c(CN(C)[C@@H](CO)C(=O)O)cc2Cl)cccc1-c1ccc2oc(N3CCN(C)CC3)nc2c1]

Example 2016

The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile: water with 10-mM ammonium acetate; Gradient: 20-60% B over 22 minutes, then a 4-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 96.4%; Observed Mass: 711.02; Retention Time: 1.88 min. Injection 2 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 96.1%; Observed Mass: 710.97; Retention Time: 1.45 min.

Example 2017: (S)-2-((5-chloro-2-((5-cyanopyridin-3-yl)methoxy)-4-((2-methyl-3-(2-(4-methylpiperazin-1-yl)benzo[d]oxazol-5-yl)benzyl)oxy)benzyl)(methyl)amino)-3-hydroxy-2-methylpropanoic Acid

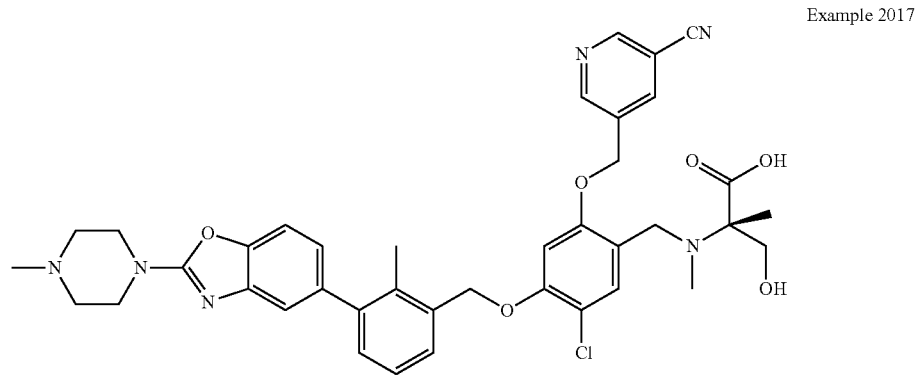 [SMILES: Cc1c(COc2cc(OCc3cncc(C#N)c3)c(CN(C)[C@@](C)(CO)C(=O)O)cc2Cl)cccc1-c1ccc2oc(N3CCN(C)CC3)nc2c1]

Example 2017

The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile: water with 10-mM ammonium acetate; Gradient: 22-62% B over 20 minutes, then a 4-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 725.21; Retention Time: 1.43 min. Injection 2 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 725.22; Retention Time: 1.57 min.

Example 2018: (S)-2-((5-chloro-2-((5-cyanopyridin-3-yl)methoxy)-4-((2-methyl-3-(2-(4-methylpiperazin-1-yl)benzo[d]oxazol-5-yl)benzyl)oxy)benzyl)(methyl)amino)pentanoic Acid

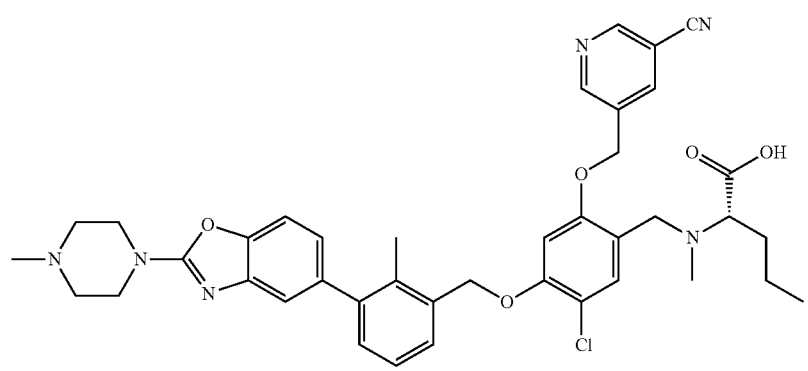

Example 2018

The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile: water with 10-mM ammonium acetate; Gradient: 25-65% B over 20 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 94.7%; Observed Mass: 723.25; Retention Time: 1.68 min. Injection 2 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 96.4%; Observed Mass: 723.23; Retention Time: 1.52 min.

BIOLOGICAL ASSAY

The ability of the compounds of formula (I) to bind to PD-L1 was investigated using a PD-1/PD-L1 Homogenous Time-Resolved Fluorescence (HTRF) binding assay.
Homogenous Time-Resolved Fluorescence (HTRF) binding assay.

The interaction of PD-1 and PD-L1 can be assessed using soluble, purified preparations of the extracellular domains of the two proteins. The PD-1 and PD-L1 protein extracellular domains were expressed as fusion proteins with detection tags, for PD-1, the tag was the Fc portion of Immunoglobulin (PD-1-Ig) and for PD-L1 it was the 6 histidine motif (PD-L1-His). All binding studies were performed in an HTRF assay buffer consisting of dPBS supplemented with 0.1% (with) bovine serum albumin and 0.05% (v/v) Tween-20. For the h/PD-L1-His binding assay, inhibitors were pre-incubated with PD-L1-His (10 nM final) for 15 m in 4 µl of assay buffer, followed by addition of PD-1-Ig (20 nM final) in 1 µl of assay buffer and further incubation for 15 m. HTRF detection was achieved using europium crypate-labeled anti-Ig (1 nM final) and allophycocyanin (APC) labeled anti-His (20 nM final). Antibodies were diluted in HTRF detection buffer and 5 µl was dispensed on top of the binding reaction. The reaction mixture was allowed to equilibrate for 30 minutes and the resulting signal (665 nm/620 nm ratio) was obtained using an EnVision fluorometer. Additional binding assays were established between the human proteins PD-1-Ig/PD-L2-His (20 & 5 nM, respectively) and $CD_8O$-His/PD-L1-Ig (100 & 10 nM, respectively).

Recombinant Proteins: Human PD-1 (25-167) with a C-terminal human Fc domain of immunoglobulin G (Ig) epitope tag [hPD-1 (25-167)-3S-IG] and human PD-L1 (18-239) with a C-terminal His epitope tag [hPD-L1(18-239)-TVMV-His] were expressed in HEK293T cells and purified sequentially by ProteinA affinity chromatography and size exclusion chromatography. Human PD-L2-His and CD80-His was obtained through commercial sources.

Sequence of recombinant human PD-1-Ig
hPD1(25-167)-3S-IG
(SEQ ID NO: 1)

```
  1 LDSPDRPWNP PRFSPALLVV TEGDNATFTC SFSNTSESPV LNWYRMSPSN

51 QTDKLAAFPE DRSQPGQDCR FRVTQLPNGR DFHMSVVRAR RNDSGTYLCG

101 AISLAPKAQI KESLRAELRV TERRAEVPTA HPSPSPRPAG QFQGSPGGGG

151 GREPKSSDKT HTSPPSPAPE LLGGSSVFLF PPKPKDTLMI SRTPEVTCVV

201 VDVSHEDPEV KFNWYVDGVE VHNAKTKPRE EQYNSTYRVV SVLTVLHQDW

251 LNGKEYKCKV SNKALPAPIE KTISKAKGQF REPQVYTLPP SRDELTKNQV

301 SLTCLVKGFY PSDIAVEWES NGQPENNYKT TPPVLDSDGS FFLYSKLTVD

351 KSRWQQGNVF SCSVMHEALH NHYTQKSLSL SPGK
```

Sequence of recombinant human PD-L1-His
hPDL1(18-239)-TVMV-His
(SEQ ID NO: 2)

```
  1 AFTVTVPKDL YVVEYGSNMT IECKFPVEKQ LDLAALIVYW EMEDKNIIQF

51 VHGEEDLKVQ HSSYRQRARL LKDQSLSGNA ALQITDVKLQ DAGVYRCMIS

101 YGGADYKRIT VKVNAPYNKI NQRILVVDPV TSEHELTCQA EGYPAKEVIW

151 TSSDHQVLSG KTTTTNSKRE EKLPNVTSTL RINTTTNEIF YCTFRRLDPE

201 ENHTAELVIP ELPLAHPPNE RTGSSETVRF QGHHHHHH
```

The table below lists the IC$_{50}$ values for representative examples of this disclosure measured in the PD-1/PD-L1 Homogenous Time-Resolved Fluorescence (HTRF) binding assay. Ranges are as follows: A=0.18 nM-0.99 nM; B=1.0 nM-5.0 nM; C=5.01 nM-10.1 nM; D=10.2 nM-200 nM; E=201 nM→10 uM

| Example Number | Range or IC50 (nM) |
| --- | --- |
| Example 1001 | A |
| Example 1002 | B |
| Example 1003 | B |
| Example 1004 | B |
| Example 1005 | B |
| Example 1006 | B |
| Example 1007 | B |
| Example 1008 | 0.67 |
| Example 1009 | B |
| Example 1010 | B |
| Example 1011 | B |
| Example 1012 | A |
| Example 1013 | B |
| Example 1014 | B |
| Example 1015 | C |
| Example 1016 | A |
| Example 1017 | A |
| Example 1018 | B |
| Example 1019 | C |
| Example 1020 | A |
| Example 1021 | C |
| Example 1022 | D |
| Example 1023 | E |
| Example 1024 | B |
| Example 1025 | A |
| Example 1026 | E |

-continued

| Example Number | Range or IC50 (nM) |
| --- | --- |
| Example 1027 | 1.7 |
| Example 1028 | E |
| Example 1029 | B |
| Example 1030 | A |
| Example 1031 | C |
| Example 2001 | 3.8 |
| Example 2002 | C |
| Example 2003 | A |
| Example 2004 | A |
| Example 2005 | — |
| Example 2006 | A |
| Example 2007 | B |
| Example 2008 | B |
| Example 2009 | A |
| Example 2010 | B |
| Example 2011 | B |
| Example 2012 | 7.2 |
| Example 2013 | B |
| Example 2014 | B |
| Example 2015 | A |
| Example 2016 | B |
| Example 2017 | A |
| Example 2018 | B |

The compounds of formula (I) possess activity as inhibitors of the PD-1/PD-L1 interaction, and therefore, may be used in the treatment of diseases or deficiencies associated with the PD-1/PD-L1 interaction. Via inhibition of the PD-1/PD-L1 interaction, the compounds of the present disclosure may be employed to treat infectious diseases such as HIV, septic shock, Hepatitis A, B, C, or D and cancer.

What is claimed is:

1. A compound of formula (I):

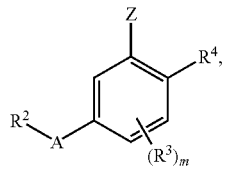

(I)

or a pharmaceutically acceptable salt thereof, wherein:

m is 0, 1, or 2;

Z is selected from —OCH$_3$ and —O(CH$_2$)$_n$Ar; wherein n is 1, 2, 3, or 4;

Ar is selected from phenyl and pyridinyl, wherein each ring is optionally substituted with 1, 2, 3, or 4 substituents independently selected from C$_1$-C$_4$alkoxy, C$_1$-C$_4$alkyl, amido, carboxy, cyano, formyl, halo, haloC$_1$-C$_4$alkyl, haloC$_1$-C$_4$alkoxy, and nitro;

A is selected from —CH$_2$O—, —OCH$_2$—, —(CH$_2$)$_2$—, —CH═CH—, —C(O)NH—, and —NHC(O)—, wherein each group is drawn with its left side attached to R$^2$ and its right side attached to the phenyl ring;

R$^2$ is selected from

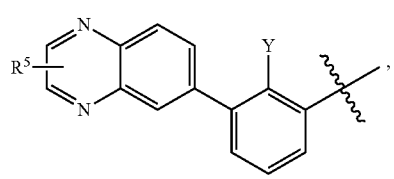

-continued

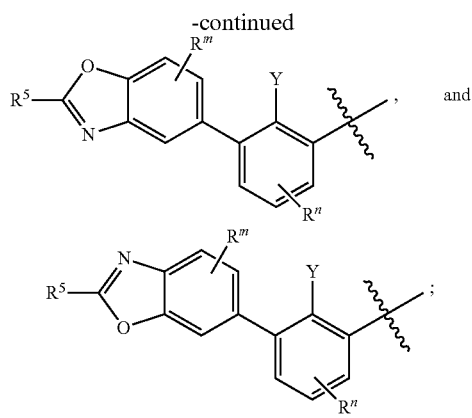

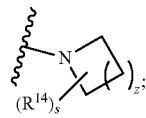

wherein
s is 0, 1, or 2;
z is 1, 2, or 3; and
each $R^{14}$ is independently selected from $C_1$-$C_4$alkoxycarbonyl, $C_1$-$C_6$alkyl, carboxy, halo, hydroxy, and hydroxy$C_1$-$C_4$alkyl.

2. A compound of claim 1, or a pharmaceutically acceptable salt thereof, wherein m is 1 and $R^3$ is halo.

3. A compound of claim 2, or a pharmaceutically acceptable salt thereof, wherein Z is —OCH$_2$Ar wherein Ar is pyridinyl substituted with a cyano group.

4. A compound of claim 3, or a pharmaceutically acceptable salt thereof, wherein A is —CH$_2$O—.

5. A compound of claim 4, or a pharmaceutically acceptable salt thereof, wherein $R^2$ is

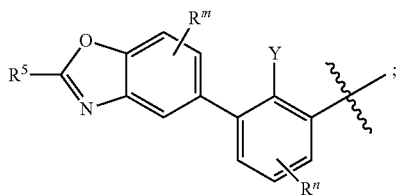

Y is selected from hydrogen and $C_1$alkyl;

$R^n$ is selected from hydrogen and $C_1$alkyl; and $R^5$ is a six- to eight-membered monocyclic or bicyclic ring containing one nitrogen atom and zero double bonds, wherein the ring is optionally substituted with one substituent selected from $C_1$alkyl, di($C_1$-$C_4$)alkylamino, amino, carboxy$C_1$-$C_4$alkyl, and $C_3$-$C_4$cycloalkyl.

6. A compound of claim 5, or a pharmaceutically acceptable salt thereof, wherein $R^4$ is —(CH$_2$)NR$^q$R$^8$; wherein $R^q$ is selected from hydrogen and $C_1$alkyl;

$R^8$ is selected from

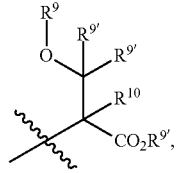 and, 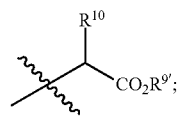

$R^9$ is selected from hydrogen and $C_1$alkyl;

each $R^{9'}$ is independently selected from hydrogen and $C_1$alkyl; and $R^{10}$ is selected from hydrogen and $C_1$-$C_4$alkyl; or $R^8$ and $R^q$, together with the nitrogen atom to which they are attached, form a ring which is wherein $R^m$ and $R^n$ are independently selected from hydrogen, $C_1$-$C_3$alkyl, and halo;

Y is selected from hydrogen, $C_1$-$C_3$alkoxy, $C_1$-$C_3$alkyl, cyano, and halo;

$R^5$ is a three- to ten-membered monocyclic or bicyclic ring optionally containing one or two heteroatoms independently selected from nitrogen and oxygen and containing zero, one, two, or three double bonds, wherein said ring is optionally substituted with one, two, or three groups independently selected from $C_1$-$C_3$alkoxy, $C_1$-$C_3$alkoxy$C_1$-$C_4$alkyl, $C_1$-$C_4$alkoxycarbonyl, $C_1$-$C_4$alkyl, di($C_1$-$C_4$)alkylamino, amino, amino$C_1$-$C_4$alkyl, carboxy, carboxy$C_1$-$C_4$alkyl, $C_3$-$C_4$cycloalkyl, and phenyl;

each $R^3$ is independently selected from $C_1$-$C_4$alkyl, cyano, halo, and halo$C_1$-$C_4$alkyl;

$R^4$ is selected from —CH$_2$OH, —CHO and —(CH$_2$)$_n$NR$^q$R$^8$; wherein n is 1, 2, 3, or 4;

$R^q$ is selected from hydrogen and $C_1$-$C_4$alkyl;

$R^8$ is selected from hydrogen, $C_1$-$C_4$alkyl, —(CH$_2$)$_n$N(CH$_3$)$_2$,

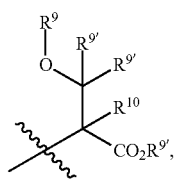 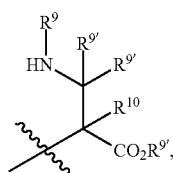

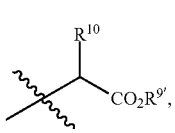 and 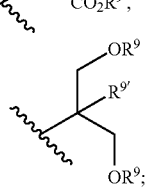

$R^9$ is selected from hydrogen and $C_1$alkyl;

each $R^{9'}$ is independently selected from hydrogen and $C_1$-$C_3$alkyl; and $R^{10}$ is selected from hydrogen and $C_1$-$C_4$alkyl; or $R^8$ and $R^q$, together with the nitrogen atom to which they are attached, form a ring which is

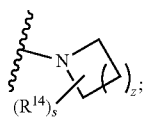

wherein
s is 1;
z is 3; and
$R^{14}$ is carboxy.

7. A compound of claim 1, or a pharmaceutically acceptable salt thereof, wherein
m is 1;
Z is —O(CH$_2$)$_n$Ar;
n is 1;
Ar is pyridinyl substituted with one cyano group;
A is —CH$_2$O;
$R^2$ is selected from

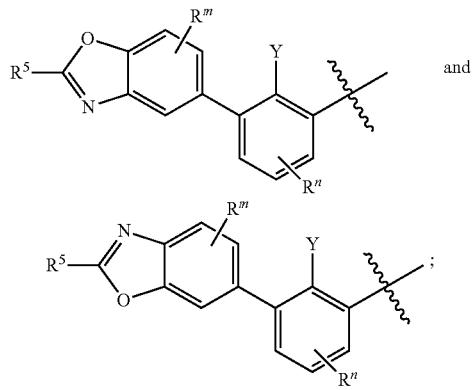

wherein
$R^m$ and $R^n$ are independently selected from hydrogen and $C_1$-$C_3$alkyl;
Y is selected from hydrogen and $C_1$-$C_3$alkyl;
$R^5$ is a five- to eight-membered monocyclic or bicyclic ring optionally containing one or two heteroatoms independently selected from nitrogen and oxygen and containing zero, one, two, or three double bonds, wherein said ring is optionally substituted with one group selected from $C_1$-$C_4$alkyl, di($C_1$-$C_4$)alkylamino, amino, carboxy$C_1$-$C_4$alkyl, and $C_3$-$C_4$cycloalkyl;
$R^3$ is halo;
$R^4$ is selected from —CH$_2$OH, —CHO and —(CH$_2$)$_n$NR$^q$R$^8$; wherein
n is 1;
$R^q$ is selected from hydrogen and $C_1$-$C_4$alkyl;
$R^8$ is selected from

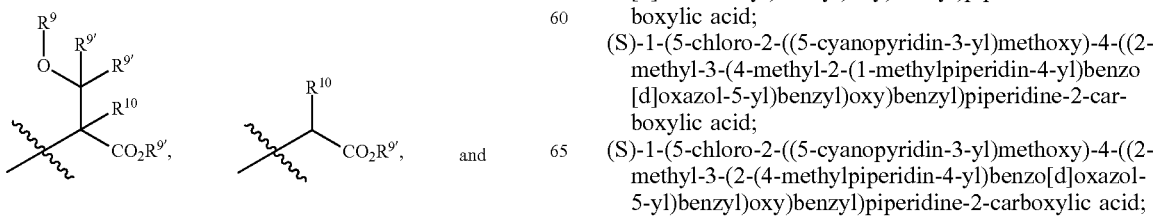

-continued

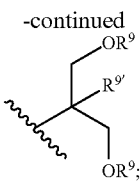

$R^9$ is selected from hydrogen and $C_1$alkyl;
each $R^{9'}$ is independently selected from hydrogen and $C_1$-$C_3$alkyl; and
$R^{19}$ is selected from hydrogen and $C_1$-$C_4$alkyl; or
$R^8$ and $R^q$, together with the nitrogen atom to which they are attached, form a ring which is

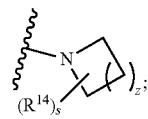

wherein
s is 1;
z is 1 or 3; and
$R^{14}$ is carboxy.

8. A compound selected from
(S)-1-(5-chloro-2-((5-cyanopyridin-3-yl)methoxy)-4-((2-methyl-3-(2-(1-methylpiperidin-4-yl)benzo[d]oxazol-5-yl)benzyl)oxy)benzyl)piperidine-2-carboxylic acid;
(S)-1-(5-chloro-2-((5-cyanopyridin-3-yl)methoxy)-4-((2-methyl-3-(2-(1-methylpiperidin-4-yl)benzo[d]oxazol-6-yl)benzyl)oxy)benzyl)piperidine-2-carboxylic acid;
(2S)-1-(5-chloro-2-((5-cyanopyridin-3-yl)methoxy)-4-((2-methyl-3-(2-(1-methylpiperidin-3-yl)benzo[d]oxazol-5-yl)benzyl)oxy)benzyl)piperidine-2-carboxylic acid;
(S)-1-(5-chloro-2-((5-cyanopyridin-3-yl)methoxy)-4-((2-methyl-3-(2-(piperidin-4-yl)benzo[d]oxazol-5-yl)benzyl)oxy)benzyl)piperidine-2-carboxylic acid;
(S)-1-(5-chloro-2-((5-cyanopyridin-3-yl)methoxy)-4-((3-(2-(1-cyclopropylpiperidin-4-yl)benzo[d]oxazol-5-yl)-2-methylbenzyl)oxy)benzyl)piperidine-2-carboxylic acid;
(2S)-1-(4-((3-(2-(8-azabicyclo[3.2.1]octan-3-yl)benzo[d]oxazol-5-yl)-2-methylbenzyl)oxy)-5-chloro-2-((5-cyanopyridin-3-yl)methoxy)benzyl)piperidine-2-carboxylic acid;
(S)-1-(5-chloro-2-((5-cyanopyridin-3-yl)methoxy)-4-((2-methyl-3-(2-(pyridin-4-yl)benzo[d]oxazol-5-yl)benzyl)oxy)benzyl)piperidine-2-carboxylic acid;
(2S)-1-(5-chloro-2-((5-cyanopyridin-3-yl)methoxy)-4-((2-methyl-3-(2-(1-methylpyrrolidin-3-yl)benzo[d]oxazol-5-yl)benzyl)oxy)benzyl)piperidine-2-carboxylic acid;
(S)-1-(5-chloro-2-((5-cyanopyridin-3-yl)methoxy)-4-((2-methyl-3-(7-methyl-2-(1-methylpiperidin-4-yl)benzo[d]oxazol-5-yl)benzyl)oxy)benzyl)piperidine-2-carboxylic acid;
(S)-1-(5-chloro-2-((5-cyanopyridin-3-yl)methoxy)-4-((2-methyl-3-(4-methyl-2-(1-methylpiperidin-4-yl)benzo[d]oxazol-5-yl)benzyl)oxy)benzyl)piperidine-2-carboxylic acid;
(S)-1-(5-chloro-2-((5-cyanopyridin-3-yl)methoxy)-4-((2-methyl-3-(2-(4-methylpiperidin-4-yl)benzo[d]oxazol-5-yl)benzyl)oxy)benzyl)piperidine-2-carboxylic acid;

(S)-1-(5-chloro-2-((5-cyanopyridin-3-yl)methoxy)-4-((3-(2-(4-(diethylamino)cyclohexyl)benzo[d]oxazol-5-yl)-2-methylbenzyl)oxy)benzyl)piperidine-2-carboxylic acid;

(S)-1-(5-chloro-2-((5-cyanopyridin-3-yl)methoxy)-4-((3-(2-(1-isopropylpiperidin-4-yl)benzo[d]oxazol-5-yl)-2-methylbenzyl)oxy)benzyl)piperidine-2-carboxylic acid;

(2S)-1-(5-chloro-2-((5-cyanopyridin-3-yl)methoxy)-4-((2-methyl-3-(2-(8-methyl-8-azabicyclo[3.2.1]octan-3-yl)benzo[d]oxazol-5-yl)benzyl)oxy)benzyl)piperidine-2-carboxylic acid;

(S)-1-(4-((3-(2-(3-aminobicyclo[1.1.1]pentan-1-yl)benzo[d]oxazol-5-yl)-2-methylbenzyl)oxy)-5-chloro-2-((5-cyanopyridin-3-yl)methoxy)benzyl)piperidine-2-carboxylic acid;

(S)-1-(4-((3-(2-(1-(carboxymethyl)piperidin-4-yl)benzo[d]oxazol-5-yl)-2-methylbenzyl)oxy)-5-chloro-2-((5-cyanopyridin-3-yl)methoxy)benzyl)piperidine-2-carboxylic acid;

(S)-1-(5-chloro-2-((5-cyanopyridin-3-yl)methoxy)-4-((2-methyl-3-(2-(tetrahydro-2H-pyran-4-yl)benzo[d]oxazol-5-yl)benzyl)oxy)benzyl)piperidine-2-carboxylic acid;

(2S)-1-(4-((3-(2-(8-oxabicyclo[3.2.1]octan-3-yl)benzo[d]oxazol-5-yl)-2-methylbenzyl)oxy)-5-chloro-2-((5-cyanopyridin-3-yl)methoxy)benzyl)piperidine-2-carboxylic acid;

5-((4-chloro-2-formyl-5-((2-methyl-3-(2-(1-methylpiperidin-4-yl)benzo[d]oxazol-5-yl)benzyl)oxy)phenoxy)methyl)nicotinonitrile;

(R)-2-((5-chloro-2-((5-cyanopyridin-3-yl)methoxy)-4-((2-methyl-3-(2-(1-methylpiperidin-4-yl)benzo[d]oxazol-5-yl)benzyl)oxy)benzyl)amino)-3-hydroxy-2-methylpropanoic acid;

5-((4-chloro-2-(hydroxymethyl)-5-((2-methyl-3-(2-(1-methylpiperidin-4-yl)benzo[d]oxazol-5-yl)benzyl)oxy)phenoxy)methyl)nicotinonitrile;

5-((4-chloro-2-4(1,3-dihydroxypropan-2-yl)(methyl)amino)methyl)-5-((2-methyl-3-(2-((1S,4S)-5-methyl-2,5-diazabicyclo[2.2.1]heptan-2-yl)benzo[d]oxazol-5-yl)benzyl)oxy)phenoxy)methyl)nicotinonitrile;

(S)-1-(5-chloro-2-((5-cyanopyridin-3-yl)methoxy)-4-((2-methyl-3-(2-((1S,4S)-5-methyl-2,5-diazabicyclo[2.2.1]heptan-2-yl)benzo[d]oxazol-5-yl)benzyl)oxy)benzyl)piperidine-2-carboxylic acid;

5-((5-((3-(2-((1S,4S)-2,5-diazabicyclo[2.2.1]heptan-2-yl)benzo[d]oxazol-5-yl)-2-methylbenzyl)oxy)-4-chloro-2-4(1,3-dihydroxypropan-2-yl)amino)methyl)phenoxy)methyl)nicotinonitrile;

5-((4-chloro-2-4(1,3-dihydroxy-2-methylpropan-2-yl)(methyl)amino)methyl)-5-((2-methyl-3-(2-((1S,4S)-5-methyl-2,5-diazabicyclo[2.2.1]heptan-2-yl)benzo[d]oxazol-5-yl)benzyl)oxy)phenoxy)methyl)nicotinonitrile;

(S)-1-(4-((3-(2-((1S,4S)-2,5-diazabicyclo[2.2.1]heptan-2-yl)benzo[d]oxazol-5-yl)-2-methylbenzyl)oxy)-5-chloro-2-((5-cyanopyridin-3-yl)methoxy)benzyl)piperidine-2-carboxylic acid;

5-((5-((3-(2-((1S,4S)-2,5-diazabicyclo[2.2.1]heptan-2-yl)benzo[d]oxazol-5-yl)-2-methylbenzyl)oxy)-4-chloro-2-4(1,3-dihydroxy-2-methylpropan-2-yl)amino)methyl)phenoxy)methyl)nicotinonitrile;

(S)-1-(5-chloro-2-((5-cyanopyridin-3-yl)methoxy)-4-((2-methyl-3-(2-(4-methylpiperazin-1-yl)benzo[d]oxazol-5-yl)benzyl)oxy)benzyl)piperidine-2-carboxylic acid;

5-((4-chloro-2-4(1,3-dihydroxypropan-2-yl)amino)methyl)-5-((2-methyl-3-(2-(4-methylpiperazin-1-yl)benzo[d]oxazol-5-yl)benzyl)oxy)phenoxy)methyl)nicotinonitrile;

5-((4-chloro-2-4(1,3-dihydroxy-2-methylpropan-2-yl)amino)methyl)-5-((2-methyl-3-(2-(4-methylpiperazin-1-yl)benzo[d]oxazol-5-yl)benzyl)oxy)phenoxy)methyl)nicotinonitrile;

(5-chloro-2-((5-cyanopyridin-3-yl)methoxy)-4-((2-methyl-3-(2-(4-methylpiperazin-1-yl)benzo[d]oxazol-5-yl)benzyl)oxy)benzyl)-L-serine;

(S)-2-((5-chloro-2-((5-cyanopyridin-3-yl)methoxy)-4-((2-methyl-3-(2-(4-methylpiperazin-1-yl)benzo[d]oxazol-5-yl)benzyl)oxy)benzyl)amino)-3-hydroxy-2-methylpropanoic acid;

(S)-2-((5-chloro-2-((5-cyanopyridin-3-yl)methoxy)-4-((2-methyl-3-(2-(4-methylpiperazin-1-yl)benzo[d]oxazol-5-yl)benzyl)oxy)benzyl)amino)pentanoic acid;

(S)-2-((5-chloro-2-((5-cyanopyridin-3-yl)methoxy)-4-((2-methyl-3-(2-(4-methylpiperazin-1-yl)benzo[d]oxazol-5-yl)benzyl)oxy)benzyl)amino)-3-methylbutanoic acid;

5-((4-chloro-2-4(1,3-dihydroxypropan-2-yl)(methyl)amino)methyl)-5-((2-methyl-3-(2-(4-methylpiperazin-1-yl)benzo[d]oxazol-5-yl)benzyl)oxy)phenoxy)methyl)nicotinonitrile;

5-((4-chloro-2-4(1,3-dihydroxy-2-methylpropan-2-yl)(methyl)amino)methyl)-5-((2-methyl-3-(2-(4-methylpiperazin-1-yl)benzo[d]oxazol-5-yl)benzyl)oxy)phenoxy)methyl)nicotinonitrile;

N-(5-chloro-2-((5-cyanopyridin-3-yl)methoxy)-4-((2-methyl-3-(2-(4-methylpiperazin-1-yl)benzo[d]oxazol-5-yl)benzyl)oxy)benzyl)-N-methyl-L-serine;

(S)-2-((5-chloro-2-((5-cyanopyridin-3-yl)methoxy)-4-((2-methyl-3-(2-(4-methylpiperazin-1-yl)benzo[d]oxazol-5-yl)benzyl)oxy)benzyl)(methyl)amino)-3-hydroxy-2-methylpropanoic acid;

(S)-2-((5-chloro-2-((5-cyanopyridin-3-yl)methoxy)-4-((2-methyl-3-(2-(4-methylpiperazin-1-yl)benzo[d]oxazol-5-yl)benzyl)oxy)benzyl)(methyl)amino)pentanoic acid;

(S)-1-(5-chloro-2-((5-cyanopyridin-3-yl)methoxy)-4-((2-methyl-3-(2-(1-phenylpiperidin-4-yl)benzo[d]oxazol-5-yl)benzyl)oxy)benzyl)piperidine-2-carboxylic acid (S)-1-(5-chloro-2-methoxy-4-((2-methyl-3-(2-(1-phenylpiperidin-4-yl)benzo[d]oxazol-5-yl)benzyl)oxy)benzyl)piperidine-2-carboxylic acid;

(S)-1-(5-chloro-2-((5-cyanopyridin-3-yl)methoxy)-4-((3-(2-(4-(methoxycarbonyl)cyclohexyl)benzo[d]oxazol-5-yl)-2-methylbenzyl)oxy)benzyl)piperidine-2-carboxylic acid;

(S)-1-(4-((3-(2-(4-carboxycyclohexyl)benzo[d]oxazol-5-yl)-2-methylbenzyl)oxy)-5-chloro-2-((5-cyanopyridin-3-yl)methoxy)benzyl)piperidine-2-carboxylic acid;

(S)-1-(5-chloro-2-((5-cyanopyridin-3-yl)methoxy)-4-((2-methyl-3-(1,2,5,6-tetra-hydropyridin-3-yl)quinoxalin-6-yl)benzyl)oxy)benzyl)piperidine-2-carboxylic acid;

(2S)-1-(4-((3-(3-(8-(tert-butoxycarbonyl)bicyclo[3.2.1]oct-2-en-3-yl)quinoxalin-6-yl)-2-methylbenzyl)oxy)-5-chloro-2-((5-cyanopyridin-3-yl)methoxy)benzyl)piperidine-2-carboxylic acid;

(2S)-1-(4-((3-(3-(8-azabicyclo[3.2.1]oct-2-en-3-yl)quinoxalin-6-yl)-2-methylbenzyl)-oxy)-5-chloro-2-((5-cyanopyridin-3-yl)methoxy)benzyl)piperidine-2-carboxylic acid;

(S)-1-(5-chloro-2-((5-cyanopyridin-3-yl)methoxy)-4-((2-methyl-3-(3-(1,2,3,6-tetrahydropyridin-4-yl)quinoxalin-6-yl)benzyl)oxy)benzyl)piperidine-2-carboxylic acid; and (S)-1-(5-chloro-2-((5-cyanopyridin-3-yl)methoxy)-4-((2-methyl-3-(3-(4-methylpiperazin-1-yl)quinoxalin-6-yl)benzyl)oxy)benzyl)piperidine-2-carboxylic acid;

or a pharmaceutically acceptable salt thereof.

9. A pharmaceutical composition comprising a compound of claim 1, or a pharmaceutically acceptable salt thereof, and a pharmaceutically acceptable carrier.

10. A method of enhancing, stimulating, and/or increasing the immune response in a subject in need thereof, said method comprising administering to the subject a therapeutically effective amount of a compound of claim 1 or a therapeutically acceptable salt thereof.

11. A method of blocking the interaction of PD-L1 with PD-1 and/or CD80 in a subject, said method comprising administering to the subject a therapeutically effective amount of a compound of claim 1 or a therapeutically acceptable salt thereof.

* * * * *

UNITED STATES PATENT AND TRADEMARK OFFICE
CERTIFICATE OF CORRECTION

PATENT NO. : 10,882,844 B2
APPLICATION NO. : 16/471531
DATED : January 5, 2021
INVENTOR(S) : Kap-Sun Yeung et al.

It is certified that error appears in the above-identified patent and that said Letters Patent is hereby corrected as shown below:

In the Claims

Column 112
Line 13, Claim 7, "$R^{19}$" should read -- $R^{10}$ --.

Column 113
Line 40, Claim 8, "-4(1,3-" should read -- -(((1,3- --;
Line 50, Claim 8, "-4(1,3-" should read -- -(((1,3- --;
Line 52, Claim 8, "-4(1,3-" should read -- -(((1,3- --; and
Line 63, Claim 8, "-4(1,3-" should read -- -(((1,3- --.

Column 114
Line 1, Claim 8, "-4(1,3-" should read -- -(((1,3- --;
Line 5, Claim 8, "-4(1,3-" should read -- -(((1,3- --;
Line 24, Claim 8, "-4(1,3-" should read -- -(((1,3- --; and
Line 28, Claim 8, "-4(1,3-" should read -- -(((1,3- --.

Signed and Sealed this
Thirtieth Day of March, 2021

Drew Hirshfeld
*Performing the Functions and Duties of the*
*Under Secretary of Commerce for Intellectual Property and*
*Director of the United States Patent and Trademark Office*